United States Patent [19]

Jefferson

[11] Patent Number: 5,599,670
[45] Date of Patent: Feb. 4, 1997

[54] β-GLUCURONIDASE AND GLUCURONIDE PERMEASE GENE SYSTEM

[75] Inventor: Richard A. Jefferson, Canberra, Australia

[73] Assignee: Cambia Biosystems. L.L.C., Canberra, Australia

[21] Appl. No.: 329,701

[22] Filed: Feb. 21, 1995

Related U.S. Application Data

[62] Division of Ser. No. 138,546, Oct. 15, 1993, Pat. No. 5,432,081, which is a division of Ser. No. 447,976, Dec. 8, 1989, Pat. No. 5,268,463, which is a continuation-in-part of Ser. No. 264,586, Oct. 31, 1988, abandoned, which is a continuation-in-part of Ser. No. 119,102, Nov. 10, 1987, abandoned.

[30] Foreign Application Priority Data

Nov. 11, 1986 [GB] United Kingdom .................... 8626862
Oct. 29, 1987 [GB] United Kingdom .................... 8725402

[51] Int. Cl.$^6$ .............................. C12Q 1/68; C12N 9/00; C12N 9/24; A61K 48/00
[52] U.S. Cl. ............................. 435/6; 435/172.3; 435/183; 435/200; 435/252.3; 435/252.33; 435/320.1; 435/325; 435/418; 435/419; 536/23.2; 536/23.7; 536/24.1; 514/44
[58] Field of Search ............................... 435/6, 69.1, 183, 435/200, 172.3, 320.1, 252.3, 252.33, 240.1, 240.2, 240.4; 536/23.2, 23.7, 24.1; 514/44

[56] References Cited

U.S. PATENT DOCUMENTS 4,753,876  6/1988  Hemming et al. .................... 435/172.3

FOREIGN PATENT DOCUMENTS

0234075A1  9/1987  European Pat. Off. .
0235410A1  9/1987  European Pat. Off. .

OTHER PUBLICATIONS

Ballantyne et al., 1976, "Comparison of simultaneous and post–incubation coupling techniques using naphthol AS–B1 glucuronide as substrate for the histochemical localication of β–glucuronidase activity in the kidney" Anal. Histochem. 21(3):247–267.
Bieseler et al., 1985, "Topological studies of lactose permease of *Escherichia coli* by protein sequence analysis" N.Y. Acad. Sci. 456:309–325.
Blanco et al., 1982, "Cloning and endonuclease restriction analysis of uidA and uidR genes in *Escherichia coil* K–12: determination of transcription direction for the uidA gene" J. Bact. 149:587–594.
Blanco et al., 1985, "Nucleotide sequence of a regulatory region of the uidA gene in *Escherichia coli* K12" Mol. gen. genet. 199:101–105.
Cohen et al., 1985, "Organization of the MAL loci of Saccharomyces" Mol. Gen. Genet. 200:1–8.
Fire, A., 1986, "Integrative transformation of Caenorhabditis elegans" EMBO J. 5:2673–2680.

Guise et al., 1985, "Isolation and expression in *Escherichia coli* of a cDNA clone encoding human β–glucuronidase" Gene 34:105–110.
Hirsh et al., 1985, "Genes affecting early development in Caenorhabditis elegans" SCHOSOB 50:69–78.
Jefferson, R. A., 1986, "DNA transformaiton of Caenorhabditis elegans: development and application of a new gene fusion system" Ph.D Thesis, Univ. of Colorado at Boulder.
Jefferson et al.,, 1986, "β–glucuronidase from *Escherichia coli* as a gene–fusion marker" Proc. Natl. Acad. Sci. U.S.A. 83:8447–8451.
Jefferson, R. A., 1987, "Assaying chimeric genes in plants: the GUS gene fusion system" Plant Mol. Bio. Rep. 5(4):387–405.
Jefferson et al., 1987, "GUS Fusions: β–glucuronidase as a sensitive and versatile gene fusion marker in higher plants" EMBO J. 6:3901–3907.
Jefferson et al., 1987, "Expression of chimeric genes in Caenorhabditis elegans" Mol. Biol. 193:41–46.
Jefferson et al., 1987, "The use of the *Escherichia coli* β–glucuronidase gene as a gene fusion marker for studies of gene expression in higher plants" Biochem. Soc. Trans. 15:17–18.
Lis et al., 1983, "new heat shock puffs and β–galactosidase activity resulting from transformation of Drosophila with and hsp70–lacZ hybrid gene" Cell 35:403–410.
Lombardo et al., 1984, "Lysosomal glycohydrolase in normal T and non–T peripheral lymphocytes" Clin. Chem. Acta. 137:67–75.
Novel et al., 1974, "Inducibility of β–glucuronidase in wild–type and hexuronate–negative mutants of *Escherichia coli* K–12" J. Bacteriol. 120:89–95.
Novel et al., 1976, "Regulatin of β–glucuronidase synthesis in *Escherichia coli* K–12: constitutive mutants specifically derepressed for uidA expression" J. Bacteriol. 127:406–417.
Palmer et al., 1983, "Genetic conrol of levels of murine kidney glucuronidase mRNA in response to androgen" Proc. Natl. Acad. Sci. U.S.A. 80:7596–7600.
Rose et al., 1981, "Yeast genes fused to β–galactosidase in *Escherichia coli* can be expressed normally in yeast" Proc. Natl. Acad. Sci. U.S.A. 78:2460–2464.

(List continued on next page.)

*Primary Examiner*—John L. LeGuyader
*Attorney, Agent, or Firm*—Seed and Berry LLP

[57] ABSTRACT

The present invention relates to the β-glucuronidase (GUS) gene fusion system, and to the cloning and characterization of the β-glucuronidase and glucuronide permease genes of *Escherichia coli*. It is based on the surprising discovery that gene fusions comprising the β-glucuronidase gene may be effectively expressed in a wide variety of organisms to produce active β-glucuronidase enzyme. Because of the abundance and availability of useful substrates for β-glucuronidase enzyme, GUS gene fusions may serve as a superior reporter gene system as well as an effective means of altering cellular phenotype. In conjunction with recombinant glucuronide permease, which may be used to render host cells permeable to β-glucuronidase substrates, the GUS gene fusion system offers almost unlimited applications in the fields of plant and animal genetic engineering.

87 Claims, 24 Drawing Sheets

OTHER PUBLICATIONS

Sebastiano et al., 1986, "β–Glucuronidase mutants o the nematode Caenorhabditis elegans" Genetics 112:459–468.

Sihavy et al., 1984, "Appendix O—The Maltose Regulon, and Appendix P—The Arabinose Regulon" *Experiments With Gene Fusion,* Cold Spring Harbor Laboratory, pp. 286–298.

Walsh et al., 1984, "Genetic construction of lactose–utilizing Xanthomonas campestris" Appl. and Enviro, Micro. 47:253–257.

Abel et al., 1986, "Delay of disease development in transgenic plants that express the tobacco mosaic virus coat protein gene" Science 232:738–743.

Bevan et al., 1984, "Binary Agrobacterium vectors for plant transformation" Nucl. Acids, Res. 12:8711–8721.

Broglie et al., 1984, "Light–regulated expression of a pea ribulose–1,5–bisphosphate carboxylase small subunit gene in transformed plant cells" Science 224:838–843.

Chapman et al., 1983, "Amplification and hormone–regulated expression of a mouse mammary tumor virus–Eco gpt fusion plasmid in mouse 3T6 cells" Mol. Cell. Biol. 3:1421–1429.

Herrera–Estrlia et al., 1983, "Chimeric genes as dominant selectable markers in plant cells" EMBO J., 2:987–995.

Nakamura et al., 1986,"An improved *Escherichia coli* expression vector for the construction and identification of full–length DNA clones" Gene 44:347–351.

Klass et al., 1984, "Isolation and characterization of a sperm–specific gene family in the nematode Caenorhabditis elegans" Mol. and Cell. Bio. 4:529–537.

Kramer et a., 1985, "Expression of the Caenorhabditis elegans collagen genes col.–1 and col.–2 is developmentally regulated" J. of Bio. Chem. 260:1945–1951.

```
GAATTCCCCCCAAAATATTCACTGTAGCCATATGTCATGAGAGTTTATCGTTCCAATACGCTCGAACGAACGTTCGGTTGCTTATTTTATGGCTTCTGTCAACGCTGTTTAAAGATTA-
1                                                 50                                                100

ATGCGATCTATATCACGCTGTGGGTATTGCAGTTTTTGGTGTTTTTGATCGGGGTGTCAGTTCTTTTTATTCCATTCTCTTCCATGGTTCTCACAGATAACTGTGTGCAACACAGA
                                                 150                                               200
                                                                                  Met Leu Arg Pro Val Glu Thr Pro Thr Arg Glu Ile Lys Lys Leu
ATTGGTTAACTAATCAGATTAAAGGTTGACCAGTATTATCTTAAATGAGGAGTCCCTT ATG TTA CGT CCT GTA GAA ACC CCA ACC CGT GAA ATC AAA AAA CTC
                                                 250                     300

Asp Gly Leu Trp Ala Phe Ser Leu Asp Arg Glu Asn Cys Gly Ile Asp Gln Arg Trp Trp Glu Ser Ala Leu Gln Glu Ser Arg Ala Ile
GAC GGC CTG TGG GCA TTC AGT CTG GAT CGC GAA AAC TGT GGA ATT GAT CAG CGT TGG TGG GAA AGC GCG TTA CAA GAA AGC CGG GCA ATT
                                                 350                                               400

Ala Val Pro Gly Ser Phe Asn Asp Gln Phe Ala Asp Ala Asp Ile Arg Asn Tyr Ala Gly Asn Val Trp Tyr Gln Arg Glu Val Phe Ile
GCT GTG CCA GGC AGT TTT AAC GAT CAG TTC GCC GAT GCA GAT ATT CGT AAT TAT GCG GGC AAC GTC TGG TAT CAG CGC GAA GTC TTT ATA
                                                 450                                               500

Pro Lys Gly Trp Ala Gly Gln Arg Ile Val Leu Arg Phe Asp Ala Val Thr His Tyr Gly Lys Val Trp Val Asn Asn Gln Glu Val Met
CCG AAA GGT TGG GCA GGC CAG CGT ATC GTG CTG CGT TTC GAT GCG GTC ACT CAT TAC GGC AAA GTG TGG GTC AAT AAT CAG GAA GTG ATG
                                                 550                                               600
```

FIG.2A

```
Glu His Gln Gly Gly Tyr Thr Pro Phe Glu Ala Asp Val Thr Pro Tyr Val Ile Ala Gly Lys Ser Val Arg Ile Thr Val Cys Val Asn
GAG CAT CAG GGC GGC TAT ACG CCA TTT GAA GCC GAT GTC ACG CCG TAT GTT ATT GCC GGG AAA AGT GTA CGT ATC ACC GTT TGT GTG AAC
                        650                                                                                          700

Asn Glu Leu Asn Trp Gln Thr Ile Pro Pro Gly Met Val Ile Thr Asp Glu Asn Gly Lys Lys Lys Gln Ser Tyr Phe His Asp Phe Phe
AAC GAA CTG AAC TGG CAG ACT ATC ATC CCG CCG GGA ATG GTG ATT ACC GAC GAA AAC GGC AAG AAA AAG CAG TCT TAC TTC CAT GAT TTC TTT
                                                    750

Asn Tyr Ala Gly Ile His Arg Ser Val Met Leu Tyr Thr Thr Pro Asn Thr Trp Val Asp Asp Ile Thr His Val Thr His Val Ala Gln
AAC TAT GCC GGG ATC CAT CGC AGC GTA ATG CTC TAC ACC ACC CCG AAC ACC TGG GTG GAC GAT ATC ACC GTG GTG ACG CAT GTC GCG CAA
                    800                                                         850

Asp Cys Asn His Ala Ser Val Asp Trp Gln Val Val Val Ala Asn Gly Asp Val Ser Val Glu Leu Arg Asp Ala Asp Gln Gln Val Ala
GAC TGT AAC CAC GCG TCT GTT GAC TGG CAG GTG GTG GCC AAT GGT GAT GTT AGC GTT GAA CTG CGT GAT GCG GAT CAA CAG GTG GCA
                                        900                                             950

Thr Gly Gln Gly Thr Ser Gly Thr Leu Gln Val Val Asn Pro His Leu Trp Gln Pro Gly Gly Tyr Leu Tyr Glu Leu Cys Val Thr
ACT GGA CAA GGC ACT AGC GGG ACT TTG CAA GTG GTG AAT CCG CAC CTC TGG CAA CCG GGT GAA GGT TAT CTC TAT GAA CTG TGC GTC ACA
                                                    1000                                            1050

Ala Lys Ser Gln Thr Glu Cys Asp Ile Tyr Pro Leu Arg Val Gly Ile Arg Ser Val Ala Val Lys Gly Gln Phe Leu Ile Asn His
GCC AAA AGC CAG ACA GAG TGT GAT ATC TAC CCG CTT CGC GGC ATC CGG TCA GTG GCA GTG AAG GGC CAG TTC CTG ATT AAC CAC
                                                        1100                                           1150
```

FIG. 2B

```
Lys Pro Phe Tyr Phe Thr Gly Phe Gly Arg His Glu Asp Asp Ala Asp Leu Arg Gly Lys Gly Phe Asp Asn Val Leu Met Val His Asp His
AAA CCG TTC TAC TTT ACT GGC TTT GGT CGT CAT GAA GAT GCG GAT CTT CGT GGC AAA GGA TTC GAT AAC GTG CTG ATG GTG CAC GAC CAC
                                                       1200

Ala Leu Met Asp Trp Ile Gly Ala Asn Ser Tyr Arg Thr Ser His Tyr Pro Tyr Ala Glu Glu Met Leu Asp Trp Ala Asp Glu His Gly
GCA TTA ATG GAC TGG ATT GGG GCC AAC TCC TAC CGT ACC TCG CAT TAC CCT TAC GCT GAA GAG ATG CTC GAC TGG GCA GAT GAA CAT GGC
                  1250                                         1300

Ile Val Val Ile Asp Glu Thr Ala Ala Val Gly Phe Asn Leu Ser Leu Gly Ile Gly Phe Glu Ala Gly Asn Lys Pro Lys Glu Leu Tyr
ATC GTG GTG ATT GAT GAA ACT GCT GCT GTC GGC TTT AAC CTC TCT TTA GGC ATT GGT TTC GAA GCG GGC AAC AAG CCG AAA GAA CTG TAC
                     1350                                          1400

Ser Glu Ala Val Asn Gly Glu Thr Gln Gln Ala Ile His Leu Gln Ala Ile Lys Glu Leu Ile Ala Arg Asp Lys Asn Ile Ser Pro Leu Ala Thr Arg Lys Leu Asp
AGC GAA GAG GCA GTC AAC GGG GAA ACT CAG CAA GCG ATT CAT TTA CAG GCG ATT AAA GAG CTG ATA GCG CGT GAC AAA AAC ATT TCG CCA CTG GCG GAA GCA ACG CGT AAA CTC GAC
                                                    1450                                       1500

Val Met Trp Ser Ile Ala Asn Glu Pro Asp Thr Arg Pro Gln Val His Gly Asn Ile Ser Pro Leu Ala Glu Ala Thr Arg Lys Leu Asp
GTG ATG TGG AGT ATT GCC AAC GAA CCG GAT ACC CGT CCG CAA GTG CAC GGG AAT ATT TCG CCA CTG GCG GAA GCA ACG CGT AAA CTC GAC
                                                         1550                                        1600

Pro Thr Arg Pro Ile Thr Cys Val Asn Val Met Phe Cys Asp Ala His Thr Asp Leu Phe Asp Val Leu Cys Leu Asn
CCG ACG CGT CCG ATC ACC TGC GTC AAT GTA ATG TTC TGC GAC GCT CAC ACC ATC AGC GAT ACC ATC TTT GAT GTG CTG TGC CTG AAC
                                                     1650
```

FIG.2C

```
Arg Tyr Tyr Gly Trp Tyr Val Gln Ser Gly Asp Leu Glu Thr Ala Glu Lys Val Leu Glu Lys Glu Leu Ala Trp Gln Glu Lys Leu
CGT TAT TAC GGA TGG TAT GTC CAA AGC GGT GAT TTG GAA ACG GCA GAG AAG GTA CTG GAA AAA GAA CTT CTG GCC TGG CAG GAG AAA CTG
                                                  1750

His Gln Pro Ile Ile Thr Glu Tyr Gly Val Asp Thr Leu Ala Gly Leu His Ser Met Tyr Thr Asp Met Trp Ser Glu Glu Tyr Gln
CAT CAG CCG ATT ATC ATC ACC GAA TAC GGC GTG GAT ACG TTA GCC GGG CTG CAC TCA ATG TAC ACC GAC ATG TGG AGT GAA GAG TAT CAG
                            1800                                                  1850

Cys Ala Trp Leu Asp Met Tyr His Arg Val Phe Asp Arg Val Ser Ala Val Val Gly Glu Gln Val Trp Asn Phe Ala Asp Phe Ala Thr
TGT GCA TGG CTG GAT ATG TAT CAC CGC GTC TTT GAT CGC GTC AGC GCC GTC GTC GGT GAA CAG GTA TGG AAT TTC GCC GAT TTT GCG ACC
                                        1900                                                  1950

Ser Gln Gly Ile Leu Arg Val Gly Gly Asn Lys Lys Gly Ile Phe Thr Arg Asp Arg Lys Pro Lys Ser Ala Ala Phe Leu Leu Gln Lys
TCG CAA GGC ATA TTG CGC GTT GGC GGT AAC AAG AAA GGG ATC TTC ACT CGC GAC CGC AAA CCG AAG TCG GCG GCT TTT CTG CTG CAA AAA
                    2000                                                  2050
```

FIG.2D

Arg Trp Thr Gly Met Asn Phe Gly Glu Lys Pro Gln Gln Gly Gly Lys Gln OP
CGC TGG ACT GGC ATG AAC TTC GGT GAA AAA CCG CAG CAG GGA GGC AAA CAA TGA ATCAACAACTCTCCTGGCGCACCATGTCGGCTACAGCCTCGGTGACGT
                                                              2100                                              2150
                                                                   →
                                                                  ORF

CGCCAATAACTTCGCCTTCGCAATGGGGCGCTCTTCCTGTTGAGTTACTACACCGAGCTCGCTGGCGTCGGTGCCGCGCGGGCACATGCTGTTACTGGTGCCGGGTATTCGATGCCTT
                                  2200                                                    2250

CGCCGAGCGTCTTTGCCGGACGAGTGTGGACAGTGTGAATACCGCTGGGAAAATTCCGCCCGTTTTACTCTTCGGTACTGCGCCGTTAATGATCTTCAGCGTGCTGGTATTCTGGGTGC
                                  2300                                                    2350

TGACCGACTGGAGCCATGGTAGCAAAGTGGTGTATGCATG
2400                  2439

FIG.2E (●) DH408/pRAJ321 (in-frame col-1: uidA):
(▲) DH408/pRAJ323 (out-of-frame col-1: uidA):
(△) DH408 (untransformed):
(■) DH408/pRAJ321 treated with pre-immune serum:
(□) DH408/pRAJ321 treated with anti-β-glucuronidase antibody.

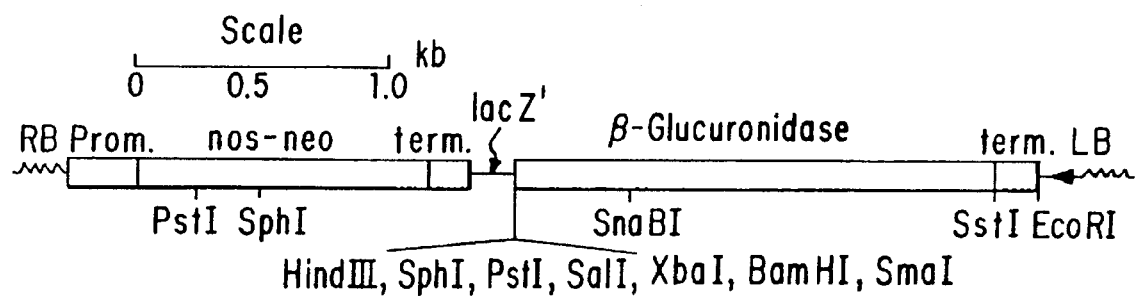
FIG. 9a
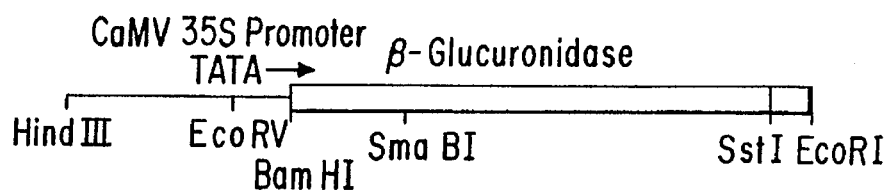
FIG. 9b
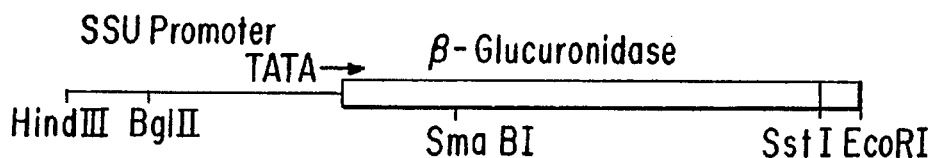
FIG. 9c
```
            Bam
pTAK1    GGATCCCC   G   GGT  GGT  CAG  TCC  CTT  ATG
                 SmaI
pTAK2    GGATCCCC  GG   GTA  GGT  CAG  TCC  CTT  ATG
                 SmaI
pTAK3    GGATCCCC  GGG  TAC  GGT  CAG  TCC  CTT  ATG
                 SmaI
```
FIG. 9d

β-glucuronidase reaction

ASSAYS histochemical      R = napthol
                   napthol ASBI fluorogenic        R = 4-methylumbelliferone R = fluorescein
                       3-O-methylfluorescein R = resorufin colorimetric       R = p-nitrophenol R = phenolphthalein

```
                10                      30                    50
     TCGCGACCGCAAACCGAAGTCGGCGGCTTTTCTGCTGCAAAAACGCTGGACTGGCATGAA 70                      90                    110
     CTTCGGTGAAAAACCGCAGCAGGGAGGCAAACAATGAATCAACAACTCTCCTGGCGCACC
                                          MetAsnGlnGlnLeuSerTrpArgThr 130                     150                    170
     ATCGTCGGCTACAGCCTCGGTGACGTCGCCAATAACTTCGCCTTCGCAATGGGGGCGCTC
     IleValGlyTyrSerLeuGlyAspValAlaAsnAsnPheAlaPheAlaMetGlyAlaLeu 190                     210                    230
     TTCCTGTTGAGTTACTACACCGACGTCGCTGGCGTCGGTGCCGCTGCGCGGGCACATGCT
     PheLeuLeuSerTyrTyrThrAspValAlaGlyValGlyAlaAlaAlaArgAlaHisAla 250                     270                    290
     GTTACTGGTGCGGGTATTCGATGCCTTCGCCGACGTCTTTGCCGGACGAGTGGTGGACAG
     ValThrGlyAlaGlyIleArgCysLeuArgArgArgLeuCysArgThrSerGlyGlyGln 310                     330                    350
     TGTGAATACCGCTGGGGAAAATTCCGCCCGTTTTTACTCTTCGGTACTGCGCCGTTAATG
     CysGluTyrArgTrpGlyLysPheArgProPheLeuLeuPheGlyThrAlaProLeuMet 370                     390                    410
     ATCTTCAGCGTGCTGGTATTCTGGGTGCTGACCGACTGGAGCCATGGTAGCAAAGTGGTG
     IlePheSerValLeuValPheTrpValLeuThrAspTrpSerHisGlySerLysValVal

Nsl I 430                     450                    470
     TATGCATATTTGACCTACATGGGCCTCGGGCTTTGCTACAGCCTGGTGAATATTCCTTAT
     TyrAlaTyrLeuThrTyrMetGlyLeuGlyLeuCysTyrSerLeuValAsnIleProTyr 490                     510                    530
     GGTTCACTTGCTACCGCGATGACCCAACAACCACAATCCCGCGCCCGTCTGGGCGCGGCT
     GlySerLeuAlaThrAlaMetThrGlnGlnProGlnSerArgAlaArgLeuGlyAlaAla 550                     570                    590
     CGTGGGATTGCCGCTTCATTGACCTTTGTCTGCCTGGCATTTCTGATAGGACCGAGCATT
     ArgGlyIleAlaAlaSerLeuThrPheValCysLeuAlaPheLeuIleGlyProSerIle
```

FIG.15A

```
          610                  630 Acc I              650
AAGAACTCCAGCCCGGAAGAGATGGTGTCGGTATACCATTTCTGGACAATTGTGCTGGCG
LysAsnSerSerProGluGluMetValSerValTyrHisPheTrpThrIleValLeuAla 670                  690                   710
ATTGCCGGAATGGTGCTTTACTTCATCTGCTTCAAATCGACGCGTGAGAATGTGGTACGT
IleAlaGlyMetValLeuTyrPheIleCysPheLysSerThrArgGluAsnValValArg 730                  750                   770
ATCGTTGCGCAGCCGTCATTGAATATCAGTCTGCAAACCCTGAAACGGAATCGCCCGCTG
IleValAlaGlnProSerLeuAsnIleSerLeuGlnThrLeuLysArgAsnArgProLeu 790                  810                   830
TTTATGTTGTGCATCGGTGCGCTGTGTGTGCTGATTTCGACCTTTGCGGTCAGCGCCTCG
PheMetLeuCysIleGlyAlaLeuCysValLeuIleSerThrPheAlaValSerAlaSer 850                  870                   890
SerLeuPheTyrValArgTyrValLeuAsnAspThrGlyLeuPheThrValLeuValLeu 910                  930                   950
GTGCAAAACCCTGGTTGGTACTGTGGCATCGGCACCGCTGGTGCXXGGATGGTCGCGAGG
ValGlnAsnProGlyTrpTyrCysGlyIleGlyThrAlaGlyAlaXxxMetValAlaArg 970                  990                   1010
ATCGGTAAAAAGAATACCTTCCTGATCGGCGCTTTGCTGGGAACCTGCGGTTATCTGCTG
IleGlyLysLysAsnThrPheLeuIleGlyAlaLeuLeuGlyThrCysGlyTyrLeuLeu 1030                 1050                  1070
TTCTTCTGGGTTTCCGTCTGGTCACTGCCGGTGGCGTTGGTTGCGTTGGCCATCGCTTCA
PhePheTrpValSerValTrpSerLeuProValAlaLeuValAlaLeuAlaIleAlaSer 1090                 1110                  1130
ATTGGTCAGGGCGTTACCATGACCGTGATGTGGGCGCTGGAAGCTGATACCGTAGAATAC
IleGlyGlnGlyValThrMetThrValMetTrpAlaLeuGluAlaAspThrValGluTyr 1150                 1170 Ban II            1190
GGTGAATACCTGACCGGCGTGCGAATTGAAGGGCTCACCTATTCACTATTCTCATTTACC
GlyGluTyrLeuThrGlyValArgIleGluGlyLeuThrTyrSerLeuPheSerPheThr
```

FIG.15B

```
        1210                    1230                    1250
CGTAAATGCGGTCAGGCAATCGGAGGTTCAATTCCTGCCTTTATTTTGGGGTTAAGCGGA
ArgLysCysGlyGlnAlaIleGlyGlySerIleProAlaPheIleLeuGlyLeuSerGly 1270                    1290                    1310
TATATCGCCAATCAGGTGCAAACGCCGGAAGTTATTATGGGCATCCGCACATCAATTGCC
TyrIleAlaAsnGlnValGlnThrProGluValIleMetGlyIleArgThrSerIleAla 1330                    1350                    1370
TTAGTACCTTGCGGATTTATGCTACTGGCATTCGTTATTATCTGGTTTTATCCGCTCACG
LeuValProCysGlyPheMetLeuLeuAlaPheValIleIleTrpPheTyrProLeuThr 1390                    1410                    1430
GATAAAAAATTCAAAGAAATCGTGGTTGAAATTGATAATCGTAAAAAAGTGCAGCAGCAA
AspLysLysPheLysGluIleValValGluIleAspAsnArgLysLysValGlnGlnGln 1450                    1470                    1490
TTAATCAGCGATATCACTAATTAATATTCAATAAAAATAATCAGAACATCAAAGGTGCAA.
LeuIleSerAspIleThrAsnEnd
```

FIG.15C

```
  9  TIVGYSLGDVANNFAFAMGALFLLSYYTDVAGVGAAARAHAVTGAGI.RC   57
     | | |    ||   || ||||| |  |||||| |             | |
  3  TKLSYGFGAFGKDFAIGIVYMYLMYYYTDVVGLSVGLVGTLFLVARIWDA   52

58  LRRRLCRTSGGQCEYRVGKFRPFLLFGTAPLMIFSVLVFWVLTDWSHGSK  107
     ||||||  |   |||||||  |    |   |||              ||
 53  INDPIMGWIVNATRSRWGKFKPWILIGTLANSVILFLLF.SAHLFEGTTQ  101

108  VVYAYLTYMGLGLCYSLVNIPYGSLATAMTQQPQSRARLGAARGIAASLT  157
     |  ||    |   |  ||  ||  ||   |          |      |||
102  IVFVCVTYILWGMTYTIMDIPFWSLVPTITLDKREREQLVPYPRFFASLA  151

158  FVCLAFLIGPSIKNSSPEEMVSVYHFVTIVLAIAGMVLYFICFKSTRENV  207
       |    |   |          |   | || ||   |  |        |
152  GFVTAGVTLPFVNYVGGGDRGFGFQMFTLYL.IAFFIVSTIITLRNVHEV  200

208  VRIVAQPSLNISLQTLKRNRPLFMLCIGALCVLISTFA.........VSA  248
     |||  |  |||   |      || | |   ||  |  |          |
201  FSSDNQPSAEGSHLTLKAIVALIYKNDQLSCLLGMALAYNVASNIITGFA  250

249  SSLFYVRYVLNDTGLFTVLVLVQNPGWYCGIGTAGAXMVARIGKKNTFLI  298
       | |  |  |   |       |    |  |       |    |   ||
251  IYYFSYVIGDADLFPYYLSYAGAANLVTLVFFPRLVKSLSRRILWAGASI  300

299  GALLGTCGYLLFFWVSVWSLPVALVALAIASIGQGVTMTVMWALEADTVE  348
     |  |  | |  ||    ||   |  |    |      ||         |||
301  LPVLSCGVLLLMALMSYHNVVLIVIAGILLNVGTALFWVLQVIMVADIVD  350

349  YGEYLTGVRIEGLTYSLFSFTRKCGQAIGGSIPAFILGLSGYIANQVQ.T  397
     ||||  || | || |  ||   |    |  ||     ||  || || | |
     ||||  ||| ||  ||   | |   || || |    |||  || || | |
351  YGEYKLHVRCESIAYSVQTMVVKGGSAFAAFFIAVVLGMIGYVPNVEQST  400

398  PEVIMGIRTSIALYPCGFMLLAFVIIWFYPLTDKKFKEI  436
      |||   |||    ||      ||    |||     |
401  QALLGMQFIMIALPTLFFMVTLILYFRFYRLNGDTLRRI  439
```

FIG. 16

β-GLUCURONIDASE AND GLUCURONIDE PERMEASE GENE SYSTEM

This application is a division of application Ser. No. 08/138,546 filed Oct. 15, 1993, now U.S. Pat. No. 5,432,081, granted Jul. 11, 1995 which is a division of application Ser. No. 07/447,976 filed Dec. 8, 1989, now U.S. Pat. No. 5,268,463 granted Dec. 7, 1993; which is a continuation-in-part of application Ser. No. 07/264,586 filed Oct. 31, 1988 (abandoned); which is a continuation-in-part of application Ser. No. 07/119,102 filed Nov. 10, 1987 (abandoned).

TABLE OF CONTENTS

1. Introduction
2. Background Of The Invention
2.1. Beta-Glucuronides
2.2. Beta-Glucuronidase
2.3. The Utility Of Gene Fusion Systems
   2.3.1. A Review of Existing Gene Fusion Systems
3. Summary Of The Invention
3.1. Abbreviations and Definitions
4. Description Of The Figures
5. Detailed Description Of The Invention
5.1. Cloning And Characterization of Beta-Glucuronidase Genes
5.2. Cloning And Characterization Of Glucuronide Permease Genes
5.3. Promoters That May Be Useful In The Beta-Glucuronidase Gene Fusion System
   5.3.1. Introduction of Beta-Glucuronide Permease And/Or Permease Into A Host Cell Or Organism
5.4. Utility Of Beta-Glucuronidase Gene Fusions As Reporter Genes
5.5. Utility of Beta-Glucuronidase Gene Fusions In The Manipulation Of Cellular Phenotype
5.6. Utility Of Glucuronide Permease
5.7. Additional Uses Of The GUS System
5.8. Useful Substrates For The Beta-Glucuronidase Gene Fusion System
5.9. Methods of Analysis of GUS Expression
   5.9.1. Lysis And Extraction
   5.9.2. Composition Of Extraction Buffers
   5.9.3. Protease Action On Gus
   5.9.4. Storage Of Extracts
   5.9.5. Treatment Of Extracts To Reduce Endogenous Fluorescence Or Absorption
   5.9.6. β-Glucuronidase Assays
      5.9.6.1. Fluorogenic Assays
      5.9.6.2. Spectrophotometric Assay
   5.9.7. Histochemical Assays Of GUS
6. Example: Cloning Of The *Escherichia Coli* Gene For Beta-Glucuronidase
6.1. Materials And Methods
   6.1.1. DNA Manipulation
   6.1.2. Protein Sequencing And Amino Acid Analysis
   6.1.3. Protein Analysis
   6.1.4. Beta-Glucuronidase Assays
   6.1.5. Purification Of Beta-Glucuronidase
6.2 Results
   6.2.1. Subcloning And Sequencing Of The uidA Gene
   6.2.2. Manipulation Of The uidA Gene For Vector Construction
   6.2.3 Purification And Properties Of Beta-Glucuronidase
6.3. Discussion
   6.3.1. Molecular Analysis Of The uid Locus
   6.3.2. The uidA Gene As Gene Fusion Marker
7. Example: Expression Of Beta-Glucuronidase Gene Fusions In *Caenorabditis Elegans*
7.1. Materials
   7.1.1. DNA Constructs
   7.1.2. Transformation With Plasmid DNA
   7.1.3. Fluorometric Assays
7.2. Results And Discussion
8. Example: Expression Of Beta-Glucuronidase Gene In Higher Plants
8.1. Materials And Methods
   8.1.1. Nucleic Acid Manipulation
   8.1.2. Plant Transformation And Regeneration
   8.1.3. Southern Blot Analysis
   8.1.4. Substrates
   8.1.5. Lysis Conditions
   8.1.6. Spectrophotometric Assay
   8.1.7. Fluorometric Assay
   8.1.8. In Situ Localization Of GUS Activity In SDS Polyacrylamide Gels
   8.1.9. Histochemical Assay
   8.1.10. Purification Of Beta-Glucuronidase
8.2. Results
   8.2.1. Higher Plants Contain No Detectable Beta-Glucuronidase Activity
   8.2.2. Construction Of Plasmids For Transformation Of Plants With GUS Fusions
   8.2.3. Chimeric GUS Genes Are Expressed In Transformed Plants
   8.2.4. Visualization Of GUS Activity On SDS-Polyacrylamide Gels
   8.2.5. GUS Activity In Plants Can Be Visualized Using Histochemical Methods
8.3. Discussion
9. Example: Cloning And Expression Of The *Escherichia Coli* Glucuronide Permease Gene
9.1. Materials and Methods
   9.1.1. Plasmids And DNA
9.2. Results And Discussion
   9.2.1. Locating The Glucuronide Permease Coding Region
   9.2.2. Analysis Of Amino Acid Sequence And The Glucuronide Permease Protein
   9.2.3. Molecular Genetic Demonstration Of Glucuronidase Permease
10. Example: Transgenic Plants Expressing A Beta-Glucuronidase Gene Fusion And Alteration Of Growth Patterns By Auxin-Glucuronide
10.1. Materials And Methods
10.2. Results And Discussion
11. Example: The Use Of GUS Fusions In Transgenic Plants: Regulation Of Chimeric Patatin Genes In Transgenic Potato Plants
11.1. Materials And Methods
11.2. Results And Discussion
   11.2.1. In Vitro Induction Experiments
   11.2.2. Patatin-GUS Expression In Planta
   11.2.3. Design Of The Field Trial
      11.2.3.1. GUS I
      11.2.3.2. GUS II
      11.2.3.3. GUS III 11.2.3.4. Containment Consideration
11.2.3.5. Planting, Growth And Harvest Procedure
11.2.3.6. Sampling And Assay Of GUS Activity
11.2.3.7. Results From The Field Analysis
12. Example: The Enzymatic Activity Assay Of The β-Glucuronidse Induced By Various Glucuronides
13. Deposit of Microorganisms

1. INTRODUCTION

The present invention relates to the β-glucuronidase (GUS) gene fusion system, and to the cloning and characterization of the β-glucuronidase and glucuronide permease genes of *Escherichia coli*. It is based on the surprising discovery that gene fusions comprising the β-glucuronidase gene may be effectively expressed in a wide variety of organisms to produce active β-glucuronidase enzyme. Because of the abundance and availability of useful substrates for β-glucuronidase enzyme, GUS gene fusions may serve as a superior reporter gene system as well as an effective means of altering cellular phenotype. In conjunction with recombinant glucuronide permease, which may be used to render host cells permeable to β-glucuronidase substrates, the GUS gene fusion system offers almost unlimited applications in the fields of plant, microbial and animal genetic engineering.

2. BACKGROUND OF THE INVENTION

In mammals, glucuronidation is a principle means of detoxifying or inactivating compounds which utilizes the UDP glucuronyl transferase system. In humans, a number of hormones, including cortisol and aldosterone testosterone and androsteindione, certain antibiotics such as chloramphenicol, toxins such as dinitrophenol, and bilirubin are among the compounds which are conjugated to form glucuronides by the glucuronyl transferase system and then excreted in urine or into the lower intestine in bile. The bacterium *Escherichia coli* has evolved to survive in the mammalian intestine, and can utilize the excreted β-glucuronides as its sole carbon source. To do so, *E. coli* has evolved mechanisms for the uptake and degradation of a wide variety of glucuronides, processes which are tightly linked genetically.

2.1. Beta-Glucoronides

Most aromatic and aliphatic glucuronides are remarkably stable relative to other types of glycoside conjugates. It is speculated that this is due to the inductive effect of the carbonyl group at C-6 on the hemiacetal linkage at C-1. Many β-glucuronides can be prepared free of other contaminating glycosides by vigorous acid hydrolysis, which cleaves glucosides, galactosides and other glycosides, but leaves most glucuronides intact. For example, complex carbohydrate polymers such as gum arabic can be reduced to a collection of monosaccharide components, and the single β-glucuronyl disaccharide aldobiuronic acid, simply by boiling gum arabic in sulfuric acid overnight. Colorigenic and fluorogenic glucorogenic substrates such as p-nitrophenyl β-D-glucuronide and 4-methylumbelliferyl β-D-glucuronide are much more stable in aqueous solution than the corresponding β-D-galactosides or β-D-glucosides.

β-Glucuronides in polysaccharide form are common in nature, most abundantly in vertebrates, where in polymeric form with other sugars such as N-acetylglucosamine they are major constituents of connective and lubricative tissues (e.g. chondroitin sulfate of cartilage, and hyaluronic acid, the principle constituent of synovial fluid and mucus). β-glucuronides are relatively uncommon in plants. However, some plant gums and mucilages produced by wounded trees, notably gum arabic from *Acacia senegal*, do contain significant fractions of β-glucuronides in polymeric form, although rarely if ever as terminal residues. Glucuronides and galacturonides found in plant cell wall components (such as pectin) are generally in the alpha configuration, and are frequently substituted as the 4-O-methyl ether; hence these are not substrates for β-glucuronidase.

As simple glycosides, β-glucuronides are extremely important as the principle form in which xenobiotics and endogenous phenols and aliphatic alcohols are excreted in the urine and bile of vertebrates (reviewed by Dutton, G. J., 1966, ed., Glucuronic Acid, Free and Combined, NY; Dutton, G. J., 1980, Glucuronidation of Drugs and Other Compounds, Florida). Detoxification of xenobiotics by glucuronidation is the most important mechanism for elimination of inappropriate compounds from the metabolism of vertebrates. Glucuronidation occurs in many tissues in vertebrates, most notably in the liver. The reaction is carried out by a set of membrane-bound enzymes catalyzing the transfer of a glucuronate residue from uridine diphosphate 1-alpha-D-glucuronate to the aglycone (xenobiotic). There are several isozymes of UDP-glucuronyl transferase that have been characterized (for a thorough review, see Dutton, 1980, supra). These enzymes are frequently part of a suite of detoxifying enzymes, including hydroxylases and mixed-function oxidases that work in concert to metabolize lipophilic, relatively insoluble compounds into the highly water-soluble glucuronide conjugates (as well as sulfates and other derivatives). These conjugates are then excreted into the bile (for the larger glucuronide conjugates) or the urine. Several thousand β-glucuronides have been characterized in urine and bile as detoxification products, many following administration of the free aglycone or a related compound (a compendium of many glucuronides can be found in Dutton, 1966, supra). In addition, many endogenous steroid hormones and bioactive substances, or bio-degradation products such as bilirubin, are conjugated and excreted as β-glucuronide conjugates. This extremely important and voluminous pathway and the fact that, among enteric bacteria, the β-glucuronidase gene appears almost exclusvely limited to *E. coli* may account in part for the success of *E. coli* as a principle and ubiquitous colonizer of the vertebrate intestine and urinary tract.

Interestingly, β-glucuronidase activity is reliably reported almost exclusively from those organisms that have, or are associated with organisms that have glucuoridation as a detoxification pathway. Thus vertebrates, which all use glucuronidation as the principle conjugation mechanism, together with some of their endogenous microbe populations (usually *E. coli*) have GUS activity. By contrast, insects and plants conjugate xenobiotics with glucose, rather than glucuronic acid, as their detoxification and derivatization mechamism, and β-glucuronidase is rarely if ever reported in these organisms or their attendant microbial populations.

2.2. Beta-Glucuronidase

Beta (β)-glucuronidase (GUS) catalyzes the hydrolysis of a very wide variety of β-glucuronides, and, with much lower efficiency, hydrolyzes some β-galacturonides; the reaction and a small selection of the available substrates for routine assay of the enzyme are diagrammed in FIG. 13. Almost any aglycone conjugated in a hemiacetal linkage to the C1 hydroxyl of a free D-glucuronic acid in the B configuration serves as a GUS substrate. Glucuronides are generally very water soluble, due to the ionizable carboxylic acid group at the 6-carbon position in the glycone.

*E. coli* β-glucuronidase (GUS) has a monomer molecular weight of about 68,200 daltons, although under certain conditions of SDS-polyacrylamide gel electrophoresis it migrates a bit slower than would be predicted (around 72–74 kDa). The behaviour of the native enzyme on gel filtration columns indicates that the active form is probably a tetramer. It is not processed at the amino terminus in *E. coli*, and is found exclusively in the cytoplasm. GUS is an exo-hydrolase; it will not cleave glucuronides in internal positions within polymers. GUS is specific for β-D-glucuronides, with some tolerance for β-galacturonides. It is inactive against β-glucosides, β-galactosides, β-mannosides, or glycosides in the alpha configuration.

β-Glucuronidase is very stable, and will tolerate many detergents and widely varying ionic conditions. It is most active in the presence of thiol reducing agents such as β-mercaptoethanol or dithiothreitol (DTT). GUS has no cofactors, nor any ionic requirements. GUS is inhibited by some divalent metal ions: 70% inhibition by $Mn^{2+}$ and $Ca^{2+}$ at 10 mM, and completely by $Cu^{2+}$ and $Zn^{2+}$ at comparable concentrations (Stoeber, 1961, Etudes des propietes et de la biosynthesase de la glucuronidase et de la glucuronidepermease chez *E. coli*. These de Docteur es Sciences, Paris). β-Glucuronidase can be assayed at any physiological pH, with an optimum between 5.0 and 7.8. The enzyme is about 50% as active at pH 4.3 and at pH 8.4. GUS from *E. coli* K12 is reasonably resistant to thermal inactivation with a half-life at 55° C. of about two hours and at 60° C., about 15 minutes. The specific inhibitor, glucaric acid 1,4 lactone (saccharic acid lactone, saccharolactone) is a very useful reversible competitor inhibitor of GUS.

β-Glucuronidase activity is extremely common in almost all tissues of all vertebrates and many molluscs (Levvy, G. A. and Conchie, J., 1966, β-Glucuronidase and the hydrolysis of glucuronides, in *Glucuronic Acid, Free and Combined*, NY. p. 301). The enzyme has been purified from many mammalian sources (e.g. Tomino et al., 1975, J. Biol. Chem. 250:8503) and shows a homotetrameric structure, with a subunit molecular weight of approximately 70 kDa. The enzyme from these sources is synthesized with a signal sequence at the amino terminus, and is then transported to and glycosylated within the endoplasmic reticulum and ultimately localized within vacuoles intracellularly. Unlike the bacterial enzyme, mammalian and molluscan GUS can cleave thioglucuronides. In general, however, the *E. coli* GUS is much more active than the mammalian enzyme against most biosynthetically derived β-glucuronides (Tomasic, J. and Keglevic, D., 1973, Biochem. J. 133:789–795; and Levvy and Conchie, supra). The genetics of GUS in mammals have been extensively characterized (reviewed in Paigen, K., 1979, Ann. Rev. Genet. 13:417–466).

GUS activity is largely if not completely absent from higher plants (Jefferson et al., 1987, EMBO J. 6:3901–3907) mosses, algae and ferns. There are a few reports of endogenous activity in plants but they rarely include quantitative tests with more than one substrate, to ensure that the activity is a true β-glucuronidase, not an activity specific for the aglycone of the test substrate (e.g., Schultz, M. and Weissenbock, G., 1987, Phytochemistry 26:933–938), nor do they often make use of specific inhibitors of GUS such as saccharolactone (see below). Such reports should also be interpreted cautiously because only rarely do plants exist without numerous exo- and endophytic organisms, many not yet classified, which could be contributing GUS activity. Specific glucuronidase that recognize endogenous substrates such as glycyrrhizin conjugates have been described, but are not capable of cleaving GUS assay substrates.

The free-living soil nematode, *Caenorhabditis elegans*, has an endogenous β-glucuronidase activity which occurs at low levels in the intestine of the worm. Enzyme activities in the other nematodes have apparently not been investigated.

Very few insects have been investigated for intrinsic GUS activity. Studies on *Drosophila melanogaster* embryos, pupae and larvae showed no detectable activity under conditions that gave very high levels of β-galactosidase (Jefferson, 1985, (published 1986) DNA Transformation of *Caenorhabditis elegans*: Development and Application of a New Gene Fusion System. PhD. Dissertation, University of Colorado, Boulder). Extracts from white flies and black flies from glasshouse populations also revealed very little if any GUS activity. Locust crop fluid liquor is a source of GUS but it is not clear whether this is an intrinsic activity, or due to microorganisms in the crop fluid.

GUS activity has not yet been found in any fungi, including *Saccharomyces*, (Jefferson, 1985, DNA Transformation of *Caenorhabditis elegans*: Development and Application of a New Gene Fusion System. PhD. Dissertation, University of Colorado, Boulder; and Schmitz et al., 1989, Gene, in press) *Schizosaccharomyces, Aspergillus, Neurospora, Cladosporium, Leptosphaeria* and other *Ascomycetes* such as barley powdery mildew or Oomycetes such as *Bremia lactuca*. There is also no detectable activity in the slime mould, *Dictyostelium discoidium* (Datta et al., 1986, Molec. Cell. Biol. 6:811–820; and Jefferson, 1985, DNA Transformation of *Caenorhabditis elegans*: Development and Application of a New Gene Fusion System. PhD. Dissertation, University of Colorado, Boulder).

GUS is not present in most bacterial genera examined, including *Bacillus, Klebsiella, Proteus, Erwinia, Rhizobium, Bradyrhizobium, Agrobacterium, Pseudomonas, Xanthomonas, Anabaena* and *Actinomycetes* although it must be remembered that induction of genes for GUS is required before activity can be found even in definitively GUS+ bacteria. The intestinal commensal Enterobacteriaceal species *E. coli* is one of the only species of bacteria that has been found reliably to have a β-glucuronidase activity; in fact, the presence of β-glucuronidase is a widely accepted diagnostic test for *E. coli* in natural populations of bacteria isolated from sources such as urine, feces, contaminated water or food (e.g. Godsey, et al., 1981, J. Clin. Microbiol. 13:483–490; Feng, P. C. S. and Hartman, P. A., 1982, Appl. Environ. Microbiol. 43:1320–1329; Trepeta, R. W. and Edberg, S. C., 1984, J. Clin. Microbiol. 19:172–174; and Moberg, L. F., 1985, Appl. Environ. Microbiol. 50:1383–1387). The GUS activity of *E. coli* populations in the intestine plays a very significant role in the physiology of most vertebrates, being partially or wholly responsible for enterohepatic recirculation of conjugated drugs, hormones and xenobiotics. Recent work indicates that there is at least one other genus of bacterium (*Alcaligenes sp.*) found in soil and water samples, and in urine and feces, that appears to produce GUS upon induction. Regions of the *E. coli* chromosome, containing portions of the GUS operon have been subcloned into *E. coli* plasmids (Blanco et al., 1982, J. Bacteriol. 149:587–594); however, prior to the present invention, the gene encoding GUS had not been isolated and characterized, nor had the coding system been expressed in a heterologous system.

In addition to β-glucuronidase enzyme, the GUS operon of *E. coli* also encodes glucuronide permease, first described biochemically by F. Stoeber (1961, These de Docteur des. Sciences, Paris). Glucuronide permease provides a mechanism for transport of β-glucuronidase through the cell membrane, and permits the entrance of a surprisingly wide variety of substrates, ranging from simple aliphatic compounds to large, complex heterocyclic conjugates (FIG. 13), into the cytoplasm. β-galactoside permease, in contrast, will only admit very simple molecules but not compounds of any appreciable complexity (e.g. complex phenolic compounds or heterocyclic compounds such as x-gal.

The combination of GUS and glucuronide permease enables *E. coli* to utilize a vast repertoire of glucuronides as sources of energy. Numerous compounds (including hormones, cholesterol, and antibiotics) are conjugated to glucuronic acid in the human liver, and thereby nourish the bacteria that constitute the intestinal flora. In turn, by metabolizing these compounds, *E. coli* significantly impacts on the bioavailability of a multitude of biologically relevant molecules.

2.3. The Utility of Gene Fusion Systems

"Reporter" genes are used in molecular biology as indicators of gene activity. A reporter gene will typically encode an enzyme activity that is lacking in the host cell or organism which is to be transformed. This allows the measurement or detection of the enzyme activity which may be used as an indicator or "reporter" of the presence of expression of the newly introduced gene.

A reporter gene may be put under the influence of a "controller" sequence, such as a promoter element. Successful expression of reporter gene product serves as an indicator of controller element activity. Additionally, a reporter gene may be used as a DNA transformation marker. Cells may be transformed with DNA comprising a gene of interest which encodes a product that is difficult or impossible to detect as well as DNA comprising the reporter gene under the control of a suitable transcriptional promoter; expression of reporter gene activity in a cell is suggestive of successful transformation with the gene of interest, the presence of which may be corroborated by standard molecular techniques. Measurement of reporter enzyme activity is frequently used to infer characteristics of the transcription of a gene encoding the reporter enzyme. These inferences depend on several assumptions that should be examined, and, when possible, controlled experimentally. Firstly, we should be aware that the ultimate regulated level of a gene product is determined by a large number of factors, only one of which is the initiation of transcription. While transcription does appear to be the principle site of regulation of gene action, there are numerous other components in the regulatory pathway that must be considered, and in some situations they will prove to be more important than transcriptional control. For instance, it is clear that DNA modifications such as methylation, chromatin configuration and possibly three dimensional structure and location of the gene can influence its expression. It is also obvious that control of precursor RNA processing and transport—including the correct excision of introns, polyadenylation of the transcript, extranuclear transport to a site of translation, and degradation of the mRNA or its precursors can have profound effects on the eventual levels of a protein product. The frequency of translational initiation, the rate of extension, the processing, modification and/or targeting or the primary protein product as well as its degradation and turnover will also inevitably affect final product levels.

The use of precise gene fusions can simplify analysis of this complex process. For example, it is possible to delineate the contribution of transcriptional control of gene expression by eliminating all the specific signals for post-transcriptional controls and replacing them with sequences from a readily assayed responder gene. Further careful gene fusion constructions can then be performed to assay the effects of inclusion of additional controller sequences, for instance the "untranslated leader sequences" or the sequences surrounding the site of translational initiation. Gene fusions need not be confined to promoter analysis, since factors affecting mRNA processing and stability, (such as polyadenylation signals or introns), or translational efficiency (such as the context of the initiator codon or mRNA secondary structure), will inevitably affect reporter enzyme levels. With the appropriate controls, many of these regulatory steps can also be analyzed with gene fusion technology. It is important to be aware of the potential contributions of these "downstream" points in the regulatory pathway of gene expression so they can be considered in the design and interpretation of gene fusion experiments.

In addition, many genes in plants and other higher organisms exist in multi-gene families whose products are very similar but can be regulated differentially during development; in fact many times members of multi-gene families are apparently inactive. By using gene fusions to individual members of such families and introducing these fusions into the genome, one can study the expression of individual genes separate and distinct from the background of the other members of the gene family.

Analysis of mutationally altered genes in plants accessible to transformation techniques is greatly facilitated by the use of sensitive and versatile reporter enzymes. Many of the regulatory parameters responsible for spatial and temporal restriction of gene activity require specialized analytic methods. Moreover, the logistics of analyzing gene function in large numbers of transgenic plants can be overwhelming, unless routine, high resolution techniques are available. Although many of the plant genes that have been characterized to date produce abundant products that are measurable by existing means, many more will certainly be described whose products are of moderate or low abundance; these will doubtlessly prove important and interesting to study, requiring increasingly sensitive methods. By using a reporter gene that encodes an enzyme activity not found in the organism being studied, the sensitivity with which chimeric gene activity can be measured is limited only by the properties of the reporter enzyme and the quality of the available assays for the enzyme.

2.3.1. A Review of Existing Gene Fusion Systems

An ideal gene fusion system should provide a reporter enzyme that is stable, tolerates amino terminal fusions, has numerous, simple and versatile assays, and that has no intrinsic background activity in the organism being studied. Furthermore, the enzyme should not interfere with normal physiological functioning of the organism, nor affect the biochemistry adversely. The assays should be sensitive enough to measure gene expression of moderate to low abundance in single cells, and should allow spatial discrimination of enzyme activity within the complex cellular patterns of tissues and organs. In addition, the assays should be quantitative, inexpensive and uncomplicated. The enzyme should be active under widely varying conditions of pH, ionic environment and temperature, and should be tolerant of general laboratory manipulations. There should also be the possibility of using the system as a true responder, providing both reporting and effecting functions, thereby allowing genetic selections to be applied. There should be methods available to use the system in live organisms quantitatively. Progress in agricultural molecular biology, and especially the use of gene fusions in transgenic plants, fungi and bacteria of agricultural and industrial importance will be greatly enhanced by the availability of suitable responder genes encoding enzymes with this set of properties.

At least seven reporter genes have been used in studies of gene expression in higher plants. These include the *E. coli* β-galactosidase (lacZ, LAC), chloramphenicol acetyl transferase (CAT), neomycin phosphotransferase (APH3'II, NPTII), nopaline synthetase (NOS), octopine synthase (OCS), firefly luciferase (luc) and bacterial luciferase (luxA and luxB). Each of these systems has properties that make them less than optimal for gene fusion analysis.

The lacZ gene from *E. coli* is part of an operon of three genes—the lac operon—and encodes a stable β-galactosidase with a wide substrate specificity. This gene was the first used in gene fusion experiments in the construction of the trp-lac fusion in the *E. coli* chromosome, well before the advent of recombinant DNA manipulations in vitro (Beckwith et al., 1967, Transposition of the lac region of *E. coli*, Cold Spring Harbor Symp. Quant. Biol. 31:393.; Miller et al., 1970, J. Bacteriol. 104:1273) and has been very widely used in studies in *E. coli* and other bacteria, and somewhat in fungi and animals. LAC fusions have been a very powerful tool due to the detailed genetic, biochemical and molecular understanding of the operon and its encoded proteins and to the availability of selective substrates such as lactose as well as substrates for spectrophotometric, fluorometric and histochemical assays. In addition, the wide availability of *E. coli* strains deficient in the components of the lac operon has enhanced its implementation in *E. coli*.

In spite of the remarkable success of lacZ fusions in the development of *E. coli* molecular genetics, β-galactosidase fusions (Helmer et al., 1984, Bio/technology 2:520–527) are difficult if not impossible to use effectively in plants because of very high endogenous β-galactosidase activity. β-Galactosidases are present in virtually all plants, and in most, if not all tissues. They are also present in many bacteria and fungi of agricultural and biotechnological importance. Additionally, intrinsic β-galactoside compounds exist in all these organisms that could be degraded by the introduction of a β-galactosidase activity, hence altering the physiology of the organism. It is possible in at least one plant system to selectively reduce or eliminate endogenous β-galactosidase background activity under conditions for histochemical analysis leaving some bacterial β-galactosidase activity. However, this treatment is not general, must be calibrated for each plant system, offers no quantitative methods, and hence is unlikely to open significant new prospects.

The *Agrobacterium tumefaciens* Ti-plasmid-encoded genes nopaline synthase (Depicker et al., 1983, J. Molec. Applied Genetics 1:561–575; Bevan et al., 1983a, Nature 304:184–187) and octopine synthase (De Greve et al., 1982, J. Mol. Applied Genetics, 1:499–513) have been used as reporter genes in the past because the opines produced by these enzymes are not normally found in plant cells. Moreover the genes were readily available, and are routinely transferred to plants upon *Agrobacterium* infection. However, these reporter genes are no longer widely used because the assays are cumbersome, of limited specificity, difficult to quantitate (Otten et al., 1978, Biochem. Biophys. Res. Commun. 527:497–500) and give no spatial information. In addition, octopine synthase cannot tolerate amino-terminal fusions (Jones et al., 1985, EMBO J. 4:2411–2418).

Until recently, the two most widely used reporter genes have been the bacterial genes chloramphenicol acetyl transferase (CAT) and neomycin phophotransferase (NPTII) which encode enzymes with specificities not normally found in plant tissues (Hererra-Estrella et al., 1983a, Nature 303:209–213; Fraley et al., 1983, J. Histochem, Cytochem. 13:441–447).

CAT catalyzes the transfer of an acetate group from acetyl-coenzyme A to one or both of the free hydroxyl groups of the antibiotic chloramphenicol, thus rendering it pharmacologically inactive. The gene and its encoded enzyme have been well characterized and the enzyme is quite stable. The most common assays involve incubation of an extract with limiting concentrations of radioactively labelled chloramphenicol and excess acetyl CoA, followed by organic extraction of the reaction products, which are more hydrophobic than the substrate, separation of the products on thin layer chromatograms and resolution of the incorporated radioactivity by autoradiography. Quantitation of the radioactivity is then done by excision of the spots from the TLC and liquid scintillation counting. This is a relatively expensive and cumbersome assay (Gorman et al., 1982, Mol. Cell. Biol. 2:1044). Alternative assays have been developed using radiolabelled acetyl CoA that avoid thin layer chromatography (Tomizawa, 1985, Cell 40:527–535; and Sleigh, 1986, Anal. Biochem, 156:251–256) but these are also expensive and prone to difficulties in extrapolating from quantitation of incorporated acetate to enzyme concentrations. Recent developments using HPLC, or fluorescently labeled chloramphenicol have streamlined this process somewhat.

NPTII, also called APH 3'II, catalyses the transfer of the terminal phosphate group from ATP to the antibiotic neomycin and its analogs, including geneticin (G418), and kanamycin. Chromatographic or electrophoretic assays have been developed to detect the activity by monitoring $^{32}P$ incorporation into the antibiotic after incubating extracts with terminally $^{32}P$ labelled ATP and substrate (e.g., Reiss et al., 1984, Gene 30:217–223). NPTII can tolerate amino-terminal fusions and remain enzymatically active, making it useful for studying transport into organelles in plants.

Both CAT and NPTII are relatively difficult, tedious and expensive to assay and suffer from variable endogenous activities in plant and animal cells (generally caused by enzymes with broader substrate specificity), which limits their sensitivity. Competing reactions catalyzed by endogenous esterases, phosphatases, transferases and other enzymes also make quantitation of CAT or NPTII by enzyme kinetics very difficult, and quantitation without enzyme kinetics to be very suspect. In addition, there are no reasonable methods for identifying cell or tissue localization with these enzymes. Because NPT II is a very versatile antibiotic selection marker (an effector) for transformation of plants, it will probably continue to be used in this capacity for some time. However, its use as a reporter gene may be ephemeral.

Attention has recently focussed on methods for light production in genetically engineered organisms using either of two luciferase genes. The firefly luciferase gene has been used as a marker in transgenic plants (Ow et al., 1986, Science 234:856–859), but the enzyme is labile, and is difficult and expensive to assay with accuracy (for a good review of the difficulties see DeLuca, M. and McElroy, W. D., 1978, Methods in Enzymology 57:3–15), the reaction is complex and there may be little potential for routine, affordable and meaningful histochemical analysis or fusion genetics. The genes luxA and luxB from *Vibrio harveyi* have also been used in several studies to monitor gene action in transgenic plants (Koncz et al., 1987, Proc. Natl. Acad. Sci., USA 84:131–135; and Langridge et al., 1989, Proc. Natl. Acad. Sci. USA 86:3219–323). However, detection of light production in situ by the expression of gene fusions of luxA and luxB, or a fused luxAB requires rather sophisticated single-photon capture and imaging systems may not unlikely to be affordable in the foreseeable future to most laboratories. In addition, there are currently no available methods to alter the spectral output to overcome absorption by the sample.

Although there is the assertion, frequently made, that the firefly and bacterial luciferases offer the possibility of true in vivo analysis, these claims should be examined carefully. First both systems require the uptake of exogenous substrates into living cells—in the case of the firefly luciferase, a complex charged molecule—in the case of the bacterial lux gene products, a relatively simple volatile aldehyde. To produce light, however, these compounds must then interact with the enzyme (modified and targeted to glyoxysomes in the case of the firefly enzyme, a heterodimer of two gene products in the case of the bacterial luciferase) and with cofactors and other substrates: for firefly luciferase $Mg^{2+}$, $O_2$, ATP; for bacterial lux FMNH. The production of light will therefore depend on high concentrations of not only the exogenously applied substrate (a difficult task to attain or measure reliably and reproducibly in all cell types) but also non-limiting levels of the other co-factors and substrates. In fact, the assay for firefly luciferase is so sensitive to ATP concentrations that it is widely used to measure ATP levels in cells and extracts. While this is an interesting and important use of luciferase, it has only confounding effects on the use of luciferase as a gene fusion marker. Because of the complexity and expense of these systems and the increasingly apparent need to quantitate gene action in situ, it is unlikely that the light production methods will receive wide acceptance in the near future. It must always be recalled that the ultimate aim of quantitation, as regards gene fusion experiments, is not to quantitate photons or dye deposition but rather gene activity.

3. SUMMARY OF THE INVENTION

The present invention relates to the β-glucuronidase (GUS) gene fusion system, and to the cloning and characterization of the β-glucuronidase and glucuronide permease genes of *Escherichia coli*. It provides for recombinant nucleic acid molecules which comprise β-glucuronidase and glucuronide permease encoding sequences, as well as functional portions thereof.

In various embodiments of the invention, nucleic acid sequences encoding GUS may be combined with a second non-GUS encoding sequence to create a GUS gene fusion. For example, GUS encoding nucleic acid may be joined to a promoter/enhancer element so that the expression of GUS is controlled by the activity of the promoter/enhancer element. In specific embodiments of the invention, expression of GUS may be placed under the control of an inducible, tissue-specific, or developmentally regulated promoter/enhancer element, including but not limited to the lacZ promoter of *E. coli*, the major sperm protein (msp-1) and col-1 promoter of *Caenorhabditis elegans*, or the ribulose bisphosphate carboxylase, cauliflower mosaic virus 35s, or patatin promoters, which are active in plants. According to various embodiments of the invention, GUS gene fusion may be used to introduce GUS activity into a wide variety of bacterial, microbial, plant, and animal host organisms. In further embodiments of the invention, GUS gene fusions may be used to provide an index of gene activity in a host cell or organism, and thereby function as a reporter gene system. In addition to its ability to withstand amino terminal fusions, GUS offers the advantage over other reporter genes, in that there is an almost complete absence of GUS activity in most organisms other than vertebrates and their attendant microflora. Surprisingly, lower and higher plants, bacteria, fungi, and many insects produce little or no GUS activity. A further advantage of the GUS gene fusion system is the wide variety of available substrates, the ease and economy of GUS assay systems, and the fact that GUS activity may be detected and accurately measured in single cells.

In further embodiments of the invention, GUS gene fusions may be used as an effective means of altering the cellular phenotype. For example, and not by way of limitation, GUS gene fusions may be used to deliver a biologically active molecule to a specific target-cell or tissue. In a particular embodiment, a biologically active molecule, such as a cytotoxic substance (e.g. cycloheximide) may be coupled to D-glucuronic acid to form a nontoxic compound which will only be toxic to cells that express GUS. If an organism that comprises a GUS gene fusion in which GUS expression is controlled by a tissue-specific promoter is exposed to this compound, tissues expressing GUS may be selectively ablated. In various embodiments of the invention, biologically active molecules including growth hormones, sex hormones, cholesterol and antibiotics, to name but a few, may be targeted to GUS-expressing cells or tissues. In another specific embodiment of the invention, transgenic plants comprising a GUS gene fusion are able to selectively benefit from the effects of an auxin supplied in the form of a glucuronide.

In still further embodiments of the invention, nucleic acid sequences encoding glucuronide permease may be used to introduce glucuronide permease activity into a host cell or tissue, thereby rendering the host permeable to GUS substrates. The utilization of glucuronide permease in conjunction with the GUS gene fusion system broadens the potential uses to apply to virtually any organism and enables the detection of GUS activity in vivo. Furthermore, by manipulating various characteristics of permease activity, host cells may be engineered to be selectively permeable to certain GUS substrates but not others. The potential uses of the GUS gene fusion system in basic research, medicine, and agriculture are seemingly unlimited.

3.1. Abbreviations and Definitions

Chimeric gene: a sequence of DNA in which nucleotide sequences not naturally occuring together are linked.

Gene fusion: A DNA construction (performed in vitro or in vivo) that results in the coding sequences from one gene (the "responder") being transcribed and/or translated under the direction of the controlling sequences of another gene (the "controller"). Responder genes can be divided into two classes, reporters and effectors, with analytical or manipulative roles, respectively.

Translational fusions: gene fusions which encode a polypeptide comprising coding information of the controller and responder genes.

Transcriptional fusions: gene fusions in which all coding sequences are derived from the responder gene.

4. DESCRIPTION OF THE FIGURES

FIG. 2 illustrates the DNA sequence of the 2439 bp insert of pRAJ220, containing the beta-glucuronidase gene.

Figure 4:
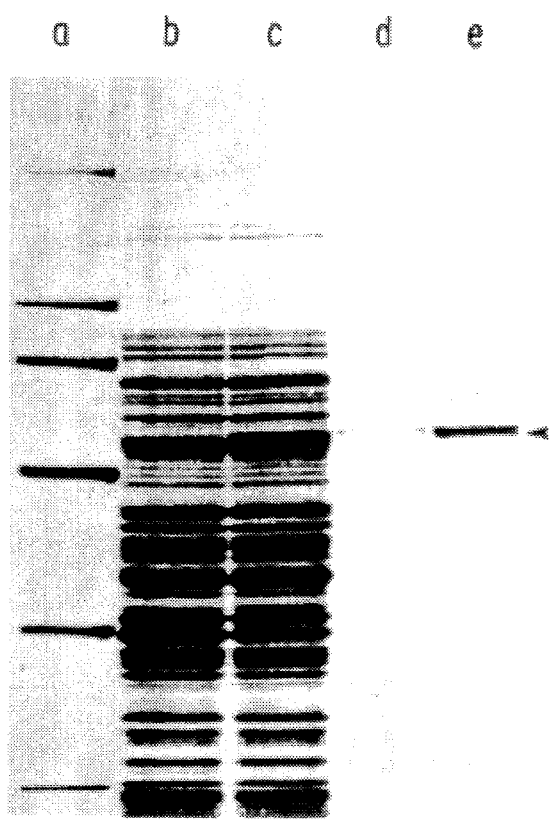

FIG. 4 illustrates the results of 7.5% SDS-PAGE analysis of beta-glucuronidase. Aliquots of supernatants from induced and uninduced cultures of *E. coli* C600 were compared with aliquots of purified β-glucuronidase. Lane (a) is molecular weight standards; lane (b) is extract from induced C600; lane (c) is extract from C600 induced for β-glucuronidase with MeGlcU'; lane (d) is 0.3 μg of purified β-glucuronidase; lane (e) is 3.0 μg aliquot of purified β-glucuronidase.

Figure 5:
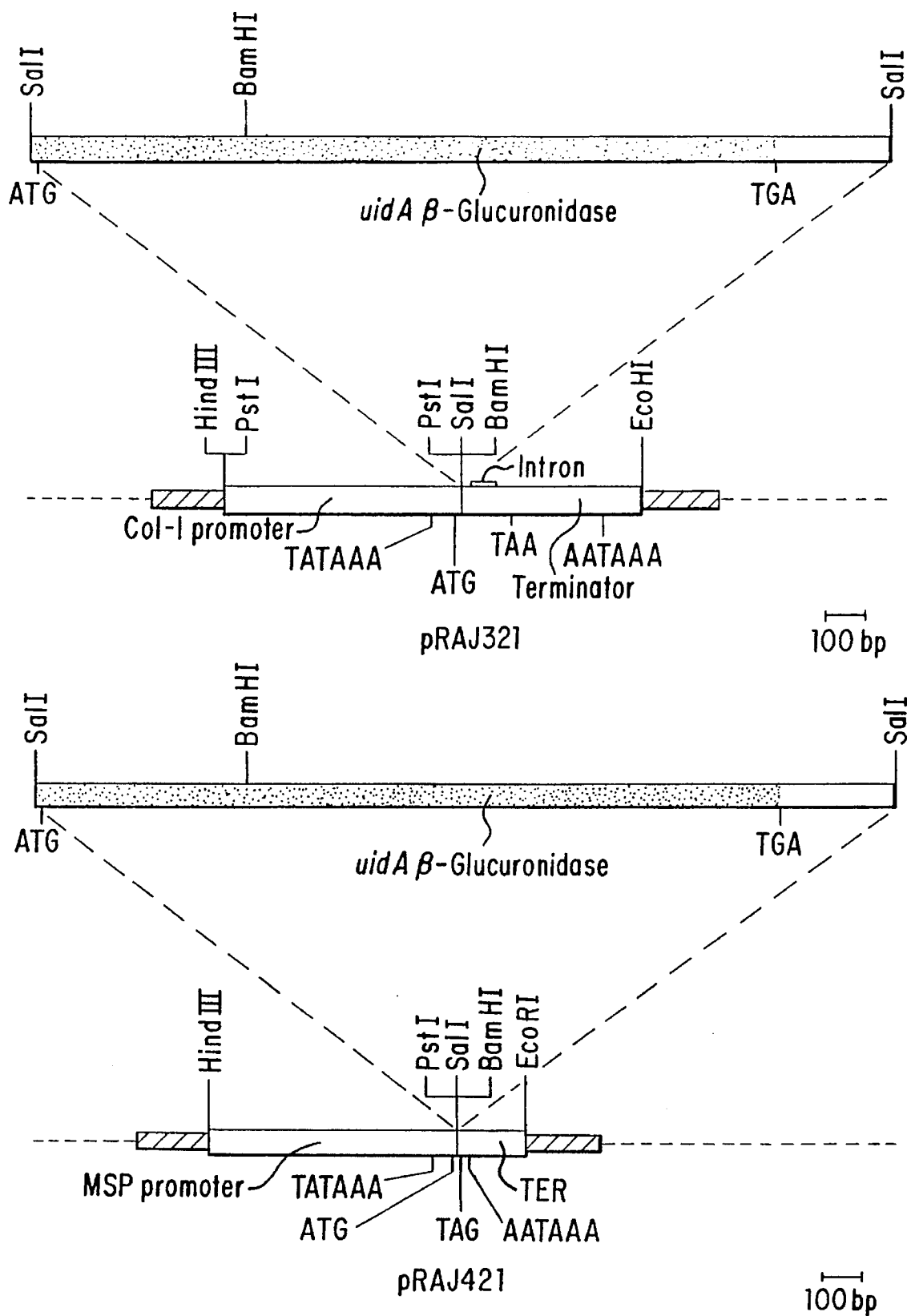

FIG. 5 illustrates structures of the col-1:GUS fusion (pRAJ321) and the MSP:GUS fusion (pRAJ421).

Figure 6:
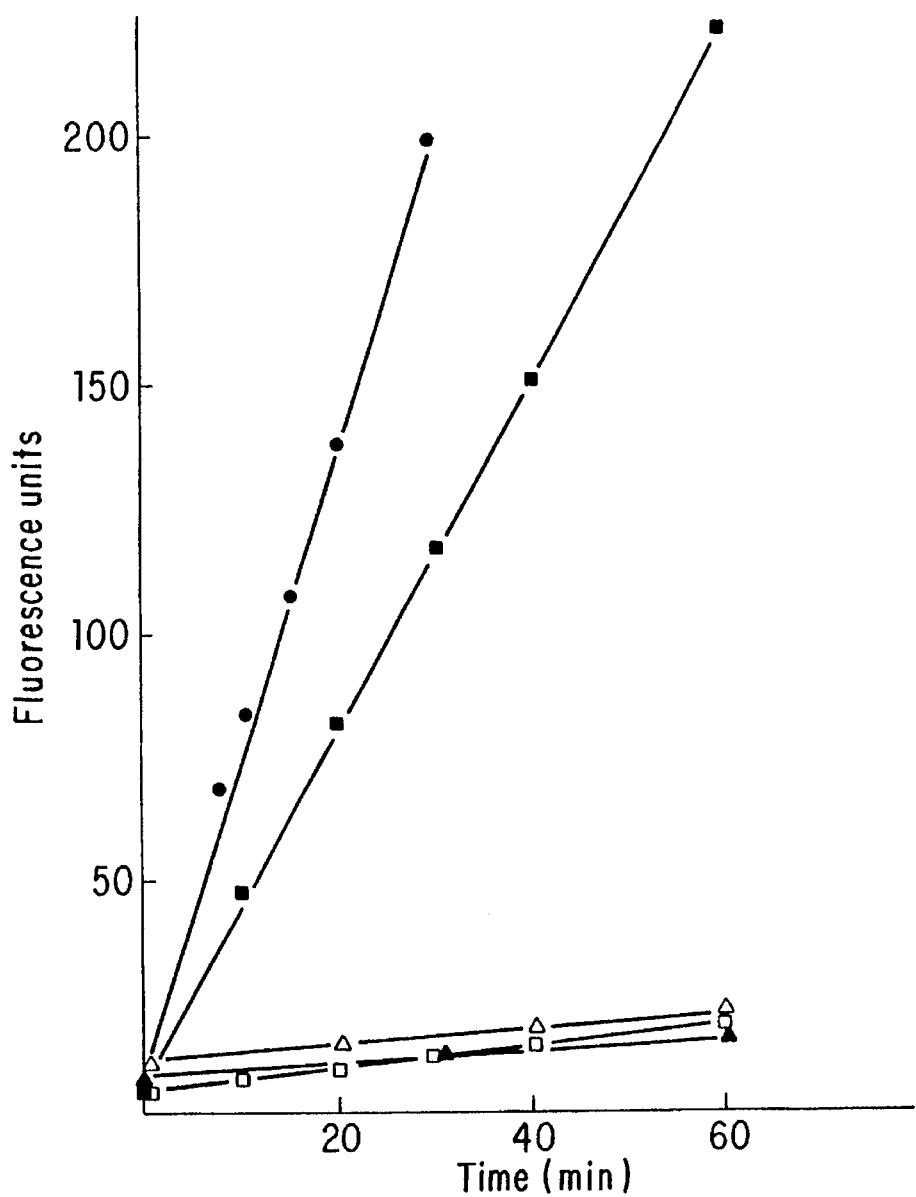

FIG. 6 shows the results of assaying beta-glucuronidase activity in transformed worms.

Figure 7A:
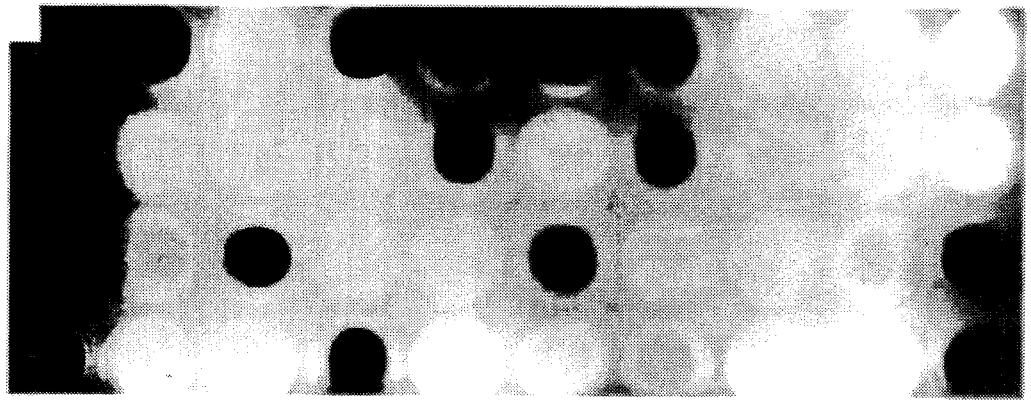
Figure 7B:
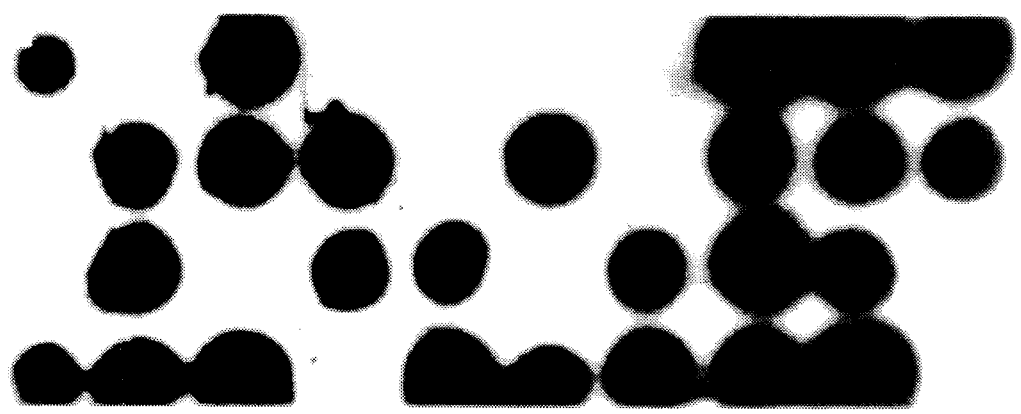

FIG. 7 illustrates the results of co-segregation analysis of beta-glucuronidase activity and transforming DNA; 40 F2 worms derived from a transformant carrying the col-1:GUS fusion were cloned onto individual petri plates, grown to saturation, harvested and washed, and the culture was split into two parts. Extracts were prepared for (a) fluorogenic beta-glucuronidase assays or (b) DNA dot blots—in the wells of a Gilson tube rack.

Figure 8A:
Figure 8B:
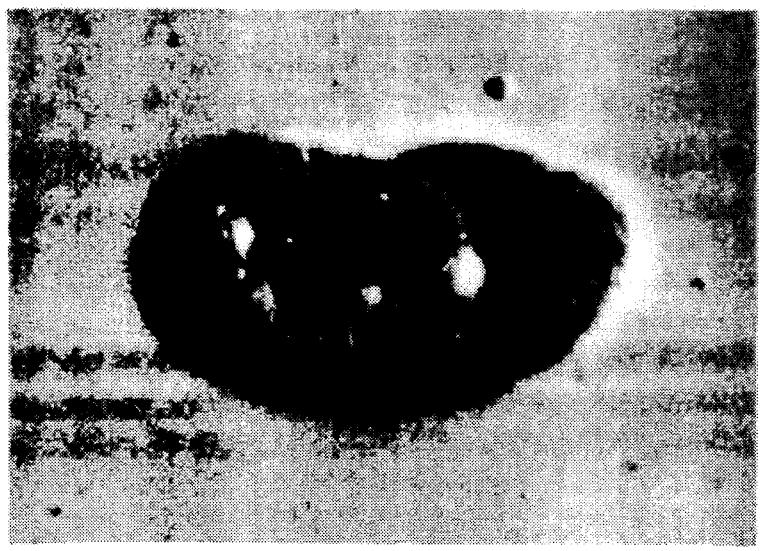

FIG. 8 illustrates histochemical visualization of beta-glucuronidase activity in worms transformed with the col-1:GUS fusion (pRAJ321);

FIG. 9 illustrates the structure of expression vectors.

Figure 10:
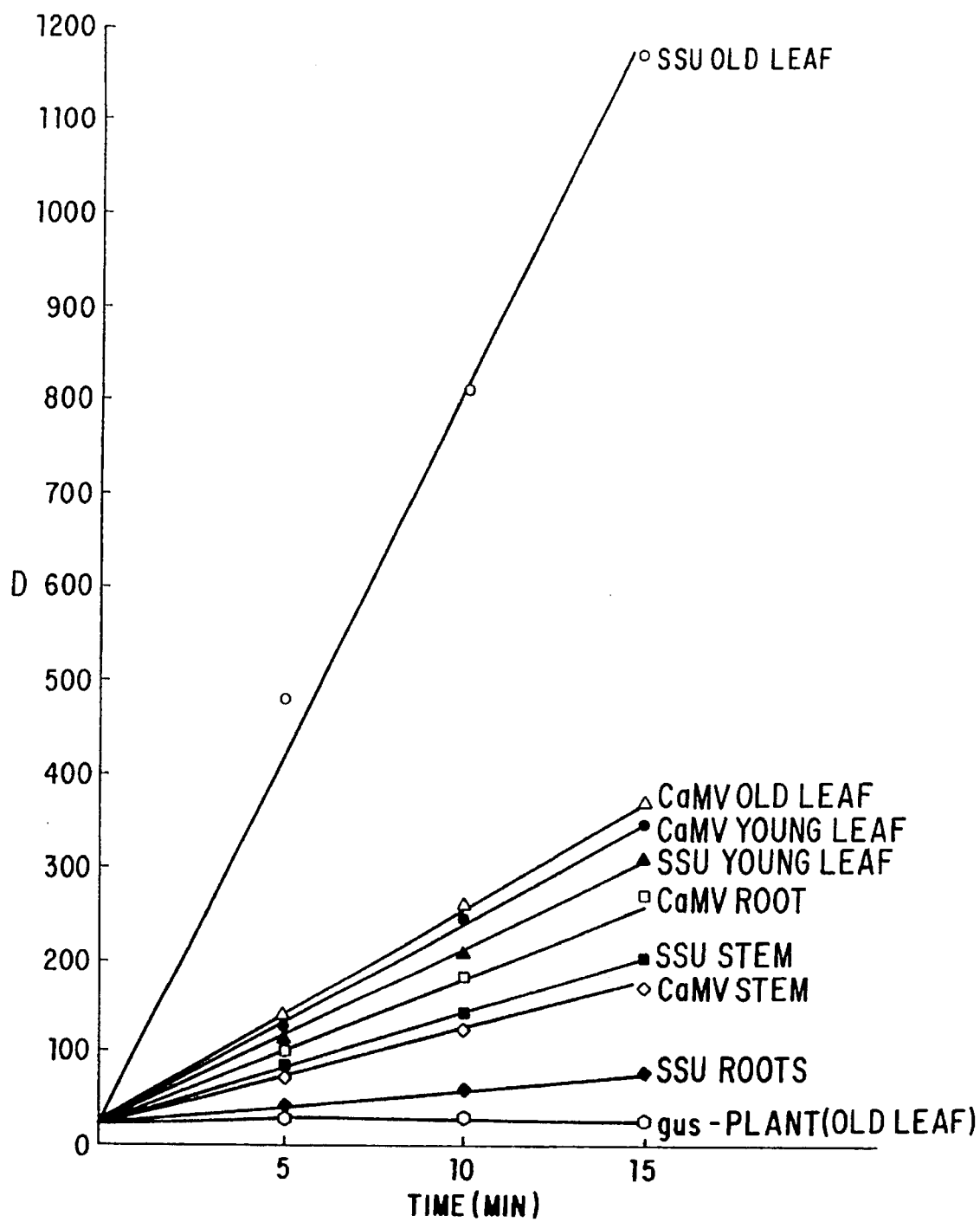

FIG. 10 is a graph illustrating beta-glucuronidase activity in extracts of different organs of transformed and non-transformed tobacco plants; extracts were prepared from old and young leaf, root, and stem from rbcS-GUS (pBI131) and CaMV-GUS (pBI121) transformants of *Nicotiana tabacum*, and then assayed for GUS activity by fluorometric assay, using 4-methyl-umbelliferyl (4-mu) glucuronide as substrate, and measuring the fluorescence with excitation at 365 nm, emission at 455 nm to determine the nanomolar (NM) concentration of fluorescent product.

Figure 11:
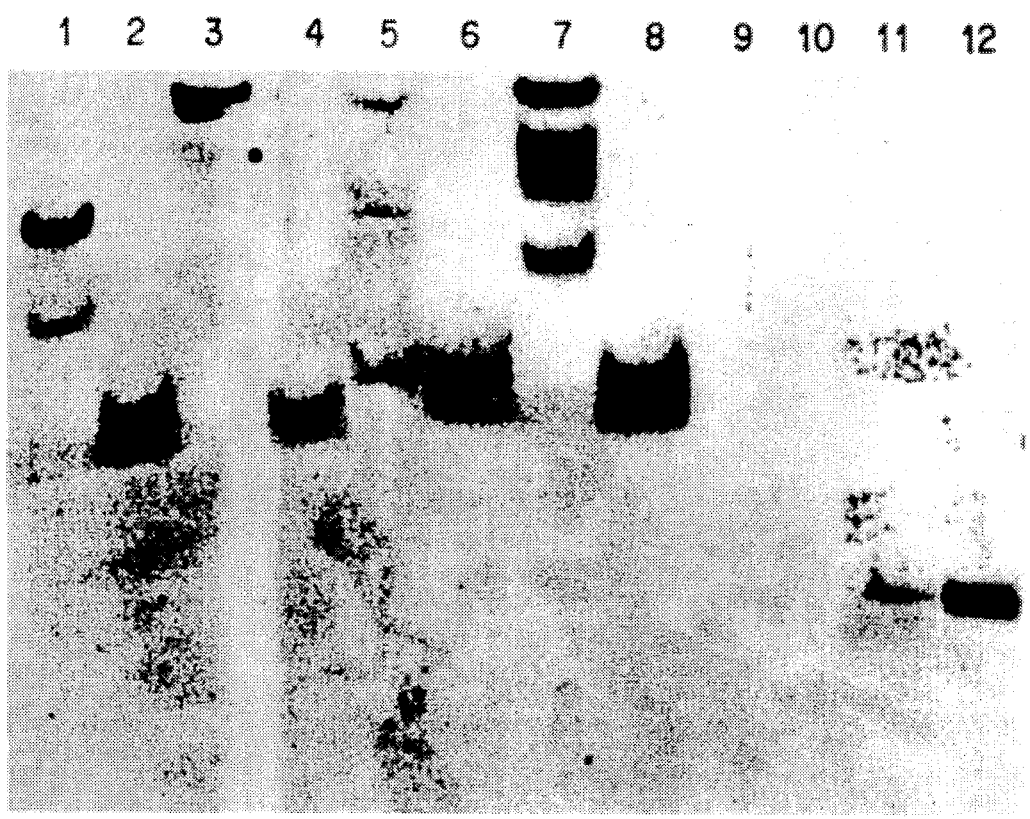
Figure 12:
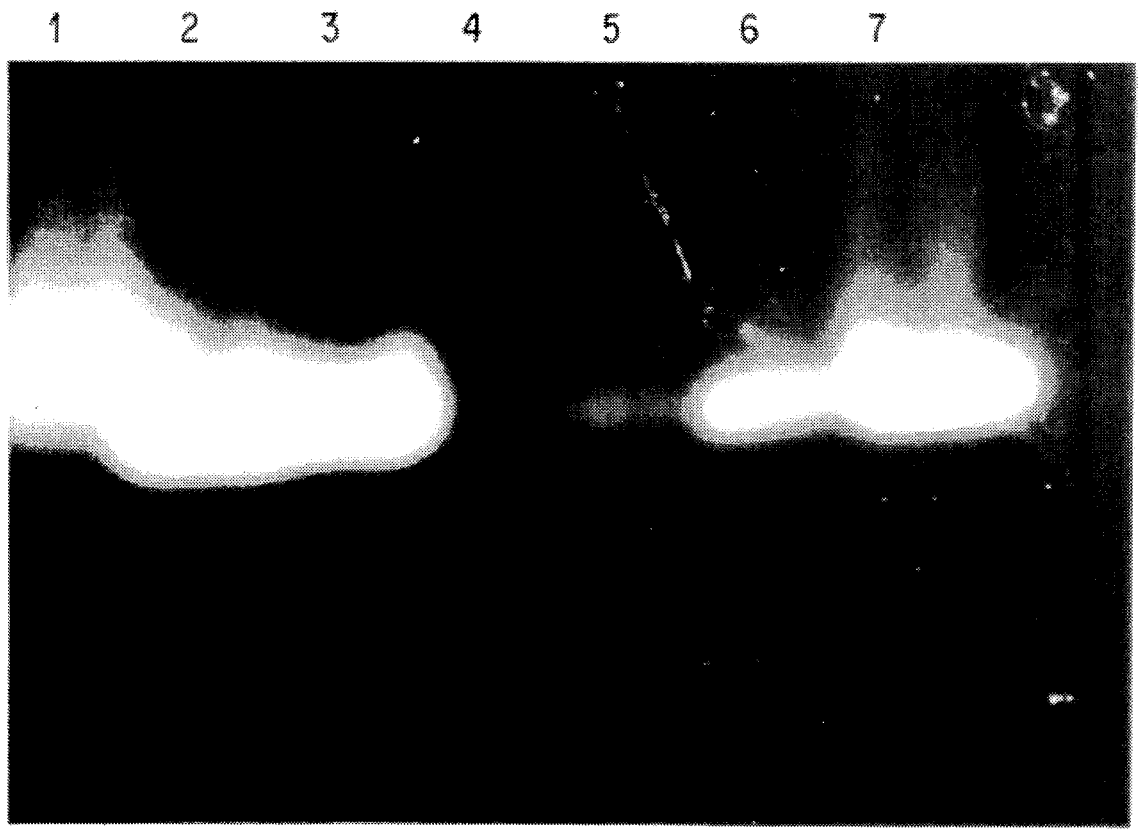

FIG. 11 is an autoradiograph of a Southern blot of DNA extracted from transformed plants and digested with restriction endonucleases;

FIG. 12 illustrates 7.5% SDS-polyacrylamide gel stained for beta-glucuronidase activity.

Lane 1. Transformed plant extract—CAB-GUS fusion.

Lane 2. Transformed plant extract—SSU-GUS 2.

Lane 3. Transformed plant extract—CaMV-GUS 21.

Lane 4. Non-transformed plant extract.

Lane 5. Non-transformed plant extract plus 1 ng GUS.

Lane 6. Non-transformed plant extract plus 10 ng GUS.

Lane 7. Non-transformed plant extract plus 50 ng GUS.

Figure 13:
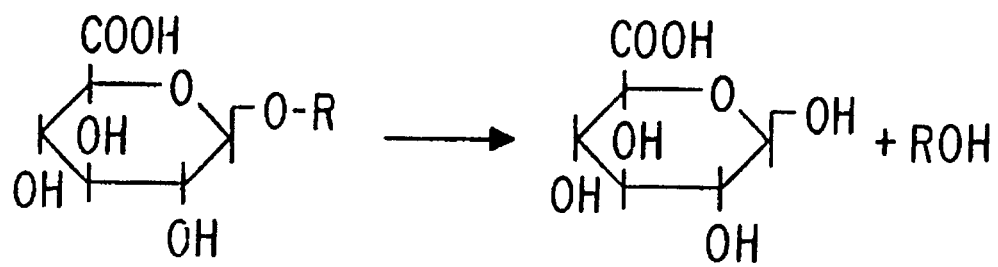
Figure 14:
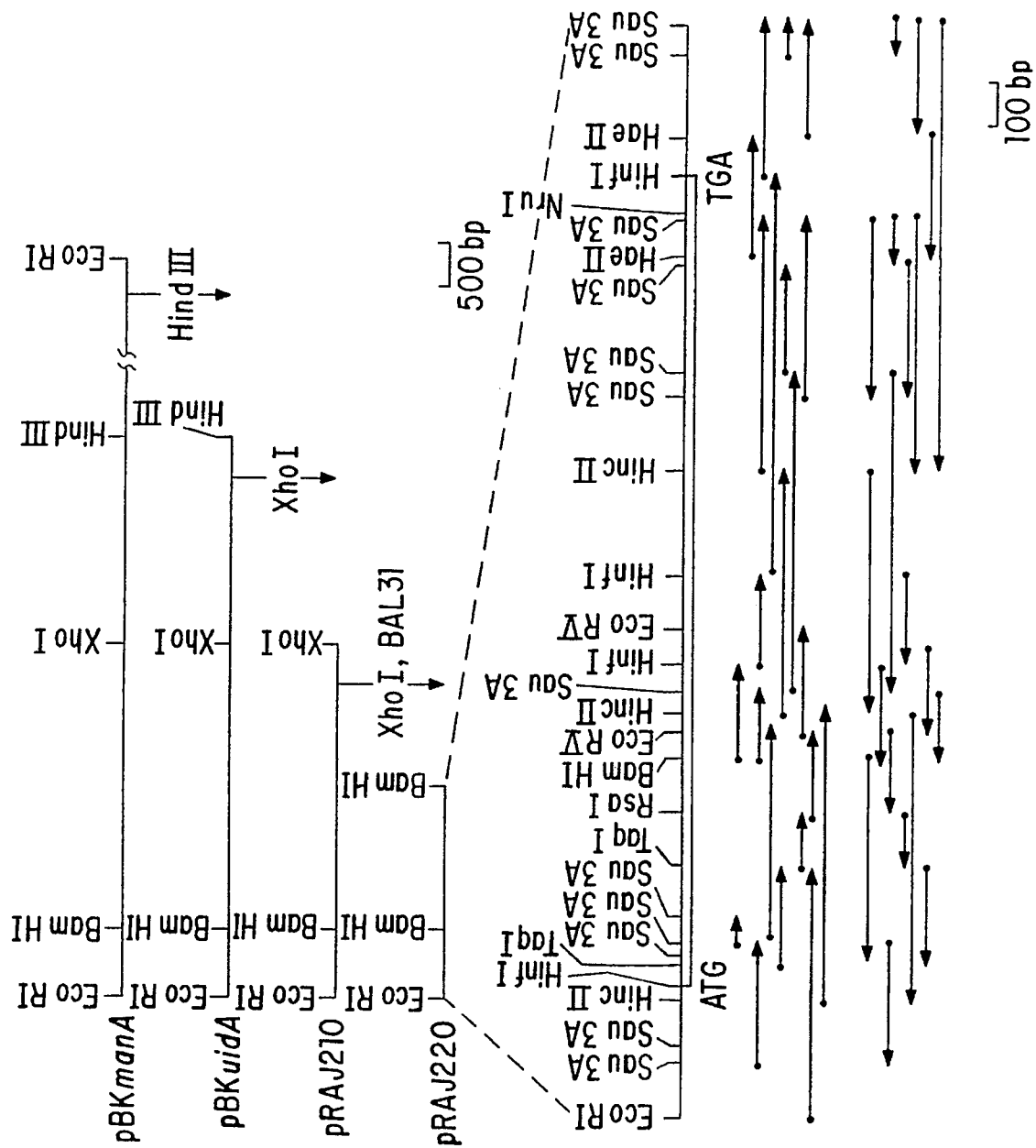
Figure 17:
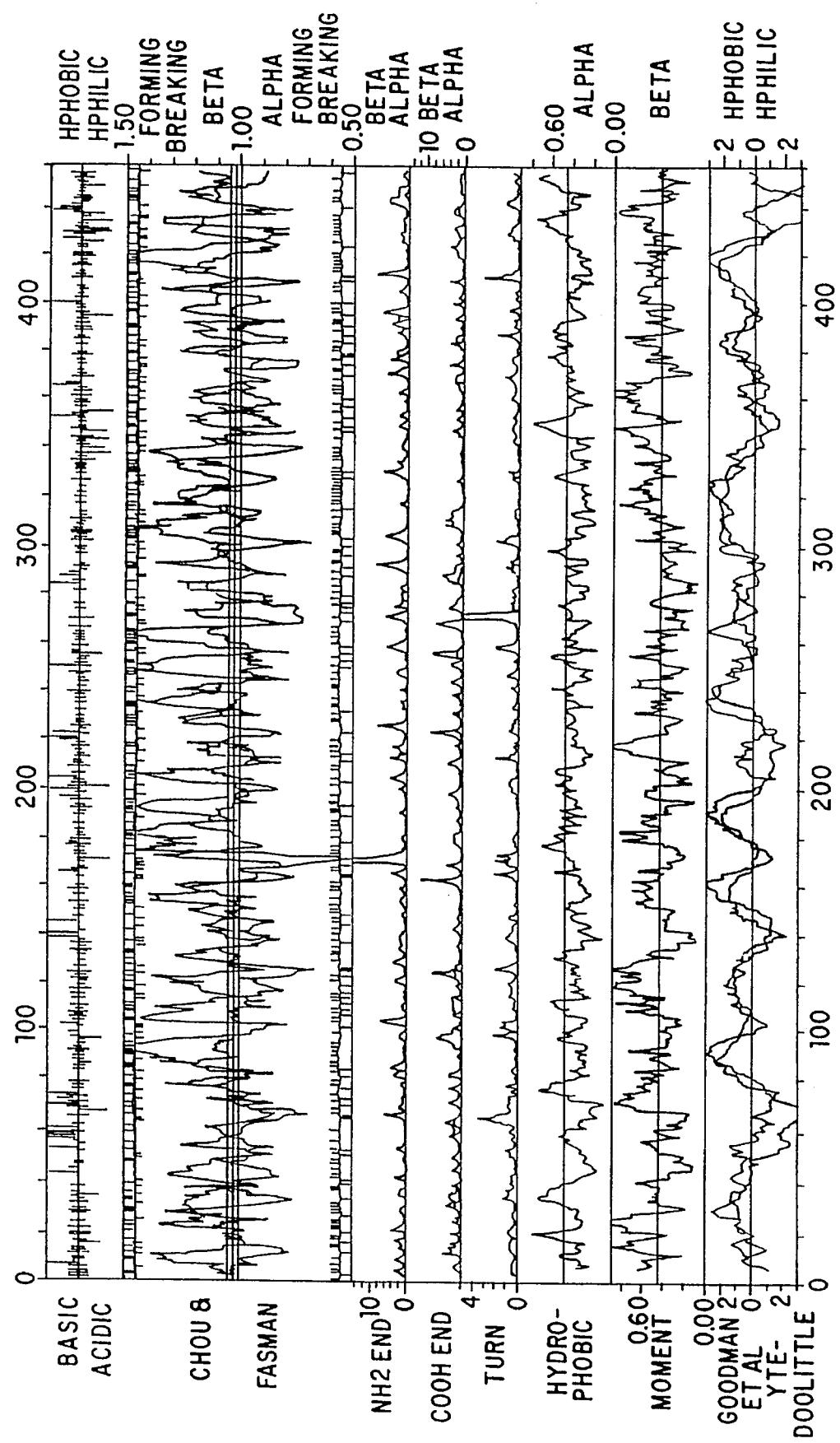

FIG. 13 illustrates the reaction catalyzed by β-glucuronidase, and the structure of substrates transported by glucuronide permease;

FIG. 14 illustrates the structure of various plasmids. The subcloning of the 3' end of pRAJ210, encoding the glucuronide permease, was done by cleaving pRAJ210 with Pst I (cleaving in the polylinker site of pUC9, proximal to the Xho I site of pRAJ210 and Nsi I which cleaves just 5' of the BamHI site of pRAJ220. The sequence of this region was determined by the method of Maxam and Gilbert;

FIG. 15 illustrates the DNA sequence of the glucuronide permease gene on pRAJ285. The sequence was determined as described in the legend to FIG. 2. The sequence shown extends from the Nru I site within GUS (sequenced by dideoxy method) through the Nsi I site into the previously unsequenced region of pRAJ210. The sequence shown extends only just past the terminator codon of the permease. This is represented on the plasmid pRAJ285. The rest of pRAJ210 has been sequenced, and is present on pRAJ280–pRAJ-284;

FIG. 16 is a comparison of the amino acid sequences of glucuronide permease (top) and the melibiose permease (bottom) using the University of Wisconsin Genetics Computer Group Best-Fit programs. The lines between sequences indicate exact matches between the two sequences. Small gaps were introduced to maximize homology. Program parameters included: Gap Weight: 5.0; Average Match: 1.00; Length Weight: 0.30; Average Mismatch: −0.10; Quality: 41.8; Length: 9; Ratio: 0.098; Gaps: 5; and FIG. 17 is an analysis of the structure of the glucuronide permease using the University of Wisconsin Genetics Computer Group PepPlot program. The bottom panel shows the hydropathy plot generated using either the Goldman or the Kyte and Doolittle criteria. The many hydrophobic domains indicate potential alpha helical trans-membrane segments. This plot is very similar to a plot obtained analyzing the melibiose permease sequence.

Figure 18:
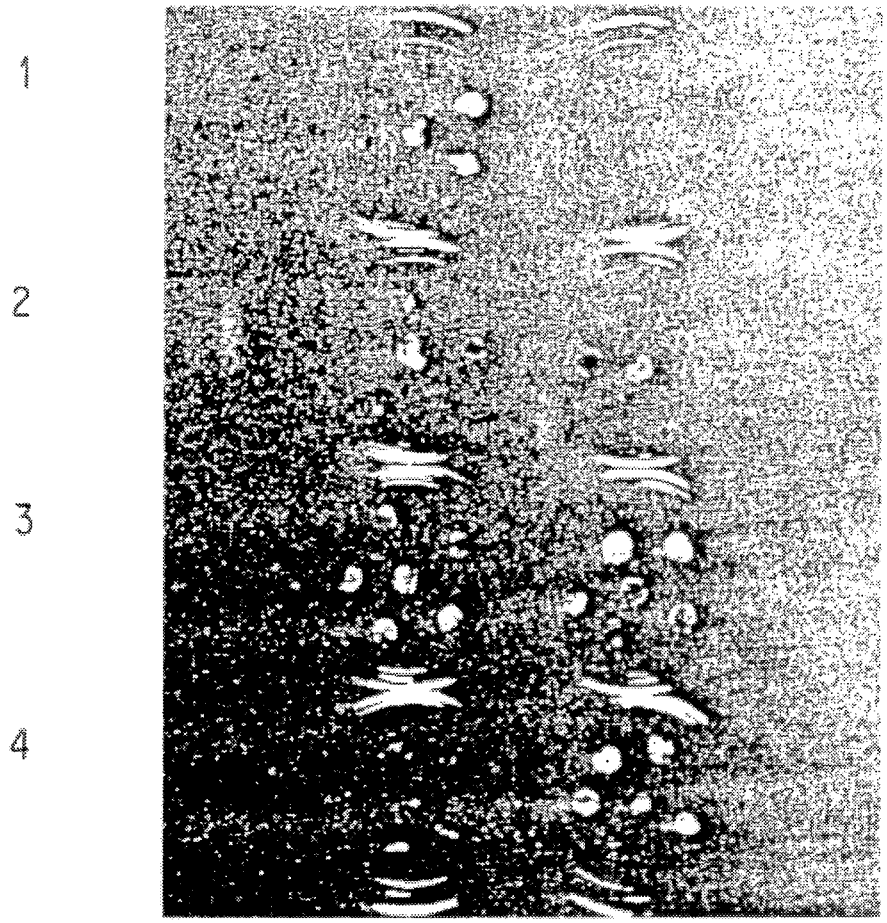

FIG. 18. Effect of trypophyl glucuronide on GUS-expressing (column A) and control (column B) leaf discs on media containing 1) no auxin; 2) 1 μM indole-3-acetic acid, 3) 1 μM tryptophyl-glucuronide, or 4) 10 μM tryptophyl glucuronide.

5. DETAILED DESCRIPTION OF THE INVENTION

The present invention relates to the β-glucuronidase gene fusion system, and to the cloning and characterization of the β-glucuronidase and glucuronide permease genes of *E. coli*. The invention provides for gene fusions which comprise β-glucuronidase and/or glucuronide permease, for organisms including plants, yeast and bacteria which comprise these gene fusions, and for methods in which the GUS gene fusion system may be used as a reporter gene or, alternatively, as a means of altering cellular phenotype.

For purposes of clarity of disclosure, and not by way of limitation, the description of the invention is divided into the following subsections:

(i) cloning and characterization of β-glucuronidase;

(ii) cloning and characterization of glucuronide permease;

(iii) Promoters that may be useful in the β-glucuronidase gene fusion system;

(iv) utility of β-glucuronidase gene fusions as reporter genes;

(v) Utility of β-glucuronidase gene fusions in the manipulation of cellular phenotype;

(vi) utility of glucuronide permease;

(vii) useful substrates for the β-glucuronidase gene fusion system; and (viii) methods of analysis of β-glucuronidase expression.

5.1. Cloning and Characterization of Beta-Glucuronidase Genes

The present invention provides for recombinant DNA molecules which encode biochemically active β-glucuronidase enzyme. In a specific embodiment of the invention, the recombinant DNA is derived from the *Esherichia coli* β-glucuronidase gene. In alternate embodiments of the invention, the β-glucuronidase encoding nucleic acid is homolgous to the *E. coli* β-glucuronidase (GUS) gene, and/or may be derived from another organism or species.

GUS-encoding nucleic acid clones may be identified using any method known in the art, including, but not limited to, the methods set forth in Section 6, infra. In particular, genomic DNA or cDNA libraries may be screened for GUS-encoding sequences using techniques such as the method set forth in Benton and Davis (1977, Science 196:180) for bacteriophage libraries and Grunstein and Hogness (1975, Proc. Natl. Acad. Sci. U.S.A. 72:396–3965) for plasmid libraries. Nucleic acid sequences known to encode GUS, such as, but not limited to, pRAJ210, described in Section 6, infra, may be used as probes in these screening experiments. Alternately, oligonucleotide probes may be synthesized which correspond to nucleic acid sequences deduced from amino acid sequence of purified GUS enzyme.

The clones identified as containing sequences homologous to the GUS gene may then be tested for the ability to encode functional GUS enzyme. For this purpose, the clones may be subjected to sequence analysis, in order to identify a suitable reading frame, initiation and termination signals. Alternatively, the cloned DNA sequence may be inserted into an appropriate expression vector, i.e., a vector which contains the necessary elements for the transcription and translation of the inserted protein-coding sequence. A variety of host/vector systems may be used, including, but not limited to, bacterial systems (plasmid, bacteriophage, or cosmid expression vectors); mammalian cells infected with virus (e.g. vaccinia virus, adenovirus, etc.); insect cell systems infected with virus (e.g. baculovirus); yeast containing yeast vectors, etc. Appropriate promoter elements are listed in section 5.3, infra. It is preferable to use an expression system in a host which exhibits low intrinsic levels of GUS activity.

Expression systems transformed with GUS-encoding sequences may then be analyzed for GUS activity using methods set forth in section 5.8, infra. GUS protein may be identified using anti-GUS antibodies, and would appear as a tetrameric protein with a monomer molecular weight of approximately 68–70 kDa.

The present invention provides for nucleic acid molecules which encode GUS active enzyme, including, but not limited to, the nucleotide sequence substantially as depicted in FIG. 2, or portions thereof. The invention also provides for molecules homologous to the nucleic acid sequence depicted in FIG. 2, or a portion thereof, as defined by hybridization or sequence analysis. The invention also provides for genetically altered forms of the GUS gene which may encode novel forms of GUS enzyme having a new or modified spectrum of substrate specificity and/or activity, as well as for GUS genes which would encode modified GUS protein, including, but not limited to, GUS linked to a signal or transit peptide.

The functional equivalents of the nucleic acid sequences depicted in FIG. 2 are also provided for by the present invention. For example, the sequences depicted in FIG. 2 can be altered by substitutions, additions or deletions that provide for functionally equivalent molecules. For example, due to the degeneracy of nucleotide coding sequences, other DNA sequences which encode substantially the same amino acid sequence as depicted in FIG. 2 may be used in the practice of the present invention. These include but are not limited to nucleotide sequences comprising all or portions of the β-glucuronidase sequence depicted in FIG. 2 which are altered by the substitution of different codons that encode the same or a functionally equivalent amino acid residue within the sequence, thus producing a silent change. For example, one or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine.. The positively charged (basic) amino acids include arginine, lysine, and histidine. The negatively charged (acidic) amino acids include aspartic and glutamic acid.

5.2. Cloning and Characterization of Glucuronide Permease Genes

The present invention provides for recombinant DNA molecules which encode glucuronide permease protein. In a specific embodiment of the invention, the recombinant DNA is derived from the E. coli glucuronide permease gene. In alternate embodiments of the invention, the glucuronide permease may be derived from another organism or species.

Glucuronide permease encoding nucleic acid clones may be identified using any method known in the art, including, but not limited to, the methods set forth in Section 9, infra. In particular, genomic DNA or cDNA libraries may be screened for glucuronide permease encoding sequences using methods such as that described by Benton and Davis (1977, Science 196:180) for bacteriophage libraries and Grunstein and Hogness (1975, Proc. Natl. Acad. Sci. U.S.A. 72:3961–3965) for plasmid libraries. Nucleic acid sequences known to enclode glucuronide permease, such as, but not limited to pRAJ285, described in Section 9 infra, may be used as probes in these screening experiments. Alternatively, oligonucleotide probes may be synthesized which correspond to nucleic acid sequences deduced from amino acid sequence of purified glucuronide permease protein.

The clones identified as containing sequences homologous to the glucuronide permease gene may then be tested for the ability to encode functional permease protein. Functional expression vectors may be constructed as described for GUS in Section 5.1, supra. It may be preferable to use the DNA containing permease sequence to transform cells which contain active GUS enzyme but which lack glucuronide permease expression. For example, and not by way of limitation, bacterial cells which express, but do not secrete GUS, but lack a functional glucuronide permease gene, when grown in the presence of a colorigenic GUS substrate, will not produce indicator color. If these bacteria are transformed with DNA encoding glucuronide permease, and functional glucuronide permease is expressed, the colorigenic substrate will enter the cells, be cleaved by GUS, and release a colored indicator substance. Any similar method of measuring glucuronide permease activity may be used in which entrance of substrate into a cell is detectable, for example, the uptake of radiolabelled substrates, a method well established in the art.

The present invention provides for nucleic acid molecules which encode glucuronide permease, including, but not limited to, the nucleotide sequence substantially as depicted in FIG. 15, or portions thereof. The invention also provides for molecules homologous to the nucleic acid sequence depicted in FIG. 15 or a portion thereof as defined by hybridization or sequence analysis. The sequence similarity to the melibiose permease, which has a substrate specificity which differs from glucuronide permease, would indicate that a variety of permease molecules homologous to the glucuronide permease are likely to exist. The invention also provides for genetically altered forms of glucuronide permease which may be more or less selective in the choice of molecules which may be transported into the cell, or otherwise altered in its activity. Further, the invention provides for functional equivalents of the nucleic acid sequences depicted in FIG. 15, as discussed in Section 5.1 relative to β-glucuronidase.

5.3. Promoters That May be Useful in the Beta-Glucuronidase Gene Fusion System According to the invention, expression of GUS or glucuronide permease may be controlled by any known promoter/enhancer element known in the art. Promoters which may be used to control CNTF expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et. al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 215:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 2:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). Furthermore, promoter/enhancer elements which are active in plants may also be utilized, including, but not limited to, light-responsive promoter sequences such as ribulose bisphosphate carboxylase (Coruzzi et al., 1984, EMBO J. 3: 1671–1680; Herrera-Estrella et al., 1984, Nature 310:115–120), the chlorophyll a/b binding protein (Cab) of the light-harvesting chlorophyll-protein complex (Apel et al., 1978, Eur. J. Biochem. 85: 581–588; Stiekema et al., 1983, Plant Physiol. 72:717–724; Thompson et al., 1983, Plants 158: 487–500; Jones et al , 1985, EMBO J 4: 2411–2418) and the ST-LS1 gene of potato (Stockhaus et al., 1989, Plant Cell 1: 805–814). Additional plant promoter sequences which may be used include but are not limited to the soybean heat shock protein hsp17.5-E or hsp17.3-B promoters (Gurley et all, 1986, Mol. Cell Biol. 6: 559–565); the *Parasponia andersoni* hemoglobin promoter (Landsmann et al., 1988, Mol. Gen. Genet. 214:68–73); the phenylalanine ammonia-lyase promoter, which appears to be active in specific cell types which accumulate phenyl-propanoid derivatives in response to wounding and also during normal development of the xylem and flower (Bevan et al., 1989, EMBO J. 8:1899–1906); and the petunia 5-enolpyruvylshikimate-3-phosphate synthase gene promoter (Benfey and Chua, 1989, Science 244:174–181) including the *Rhizobium meliloti* FIXD gene promoter described in U.S. Pat. No. 4,782,022, issued Nov. 1, 1988, by Puhler et al.; the nopaline synthase promoter (Ha and An, 1989, Nucleic Acids Res. 17:215–224; An et al., 1988, Plant Physiol. 88:547–552); rol A, B and C promoters of *Agrobacterium rhizogenes* (Schmulling et al., 1989, Plant Cell 1:665–670; Sugaya et al., 1989, Plant Cell Physiol. 30:649–654); the patatin promoter (Rocha-Sosa et al., 1989, EMBO J. 8:23–29) and the cauliflower mosaic virus (CaMV) 35S promoter (Odell et all, 1985, Nature 313:810–812; Jensen et al., 1986, Nature 321:669–674; Jefferson et al., 1987, EMBO J. 6:3901–3907; Kay et al., 1987, Science 236:1299–1302; and Sanders et al., 1987, Natl. Acids Res. 14:1543–1558).

5.3.1. Introduction of Beta-Glucuronidase and/or Permease into a Host Cell or Organism Recombinant DNA comprising nucleic acid sequence encoding GUS or glucuronide permease, together with an appropriate controller sequence, may be introduced into a host cell or organism using any method known in the art, including, but not limited to, transfection, transformation, infection, or microinjection, utilizing methods including, but not limited to, calcium phosphate or DEAE-dextran transformation, electroporation, or cell gun.

In preferred embodiments of the invention, the *Agrobacterium tumefaciens* gene transfer system may be used to introduce the recombinant constructs of the invention into plants; generally, this system may be utilized to transfer DNA into dicotyledonous plants (Bevan et al., 1982, Ann. Rev. Genet. 16:357–384; Rogers et al., 1986, Methods Enzymol. 118:627–641; Fraley et al., 1986, CRC Crit. Rev. Plant Sci. 4:1–46; Hooykaas et al., 1984, Adv. Genet. 22:210–283; Nester et al., 1984, Ann. Rev. Plant Physiol. 35:387–413). To this purpose, vectors such as, but not limited to, binary *Agrobacterium* vectors for plant transformation may be utilized, such as, for example, the vector described by Bevan (1984, Nucl. Acids. Res. 12:8711–8721). Xanthi may be transformed by a leaf inoculation procedure such as that described by Horsch et al. (1985, Science 227:1229–1231).

Additional methods for introducing DNA into plants may also be utilized, particularly if the recombinant construct is to be used to create a transgenic monocotyledonous plant. Such methods would include, but are not limited to poly-(ethylene glycol) and calcium-mediated uptake of naked DNA (Hain et al., 1985, Mol. Gen. Genet. 199:161–168; Paszkowski et al., 1984, EMBO J. 3:2717–2722; Potrykus et al., 1985, Mol. Gen. Genet. 199:169–177), electroporation (Fromm et al., 1985, Proc. Natl. Acad. Sci. U.S.A. 82:5824–5828), microinjection, macroinjection and particle bombardment.

5.4. Utility of Beta-Glucuridase Gene Fusions as Reporter Genes

According to the invention, GUS gene fusions may be utilized as a reporter gene system. Advantages of using the GUS gene fusion system include the persistent activity of GUS despite amino-terminal fusions, the abundant substrates for GUS available, and the ease and economy of many GUS assays. Furthermore, GUS activity may be detected in samples as small as a single cell.

In various embodiments of the invention, GUS gene fusions may be used as transcriptional gene fusions or translational gene fusions.

According to particular embodiments of the invention, GUS gene fusions can be used to measure the activity of a controller element. For example, and not by way of limitation, a gene fusion comprising a GUS encoding nucleic acid under the control of a promoter/enhancer element, X, could be used to generate a transgenic plant. Tissue-specific activity of promoter X would be detectable by the observation that GUS activity was expressed in some plant tissues, but not others. Similarly, a GUS gene fusion comprising controller sequences such as a ribosome binding site or another translation-related sequence, a signal peptide, or a chloroplast or nucleus-target peptide, to name but a few, could be used to test the activities and explore the properties of the controller element.

According to further embodiments of the invention, GUS gene fusions could be used to report on the expression of a second gene of interest. In this context, gene of interest is construed to mean any gene which encodes a product (e.g. RNA or protein) that is of interest, i.e., that is the subject of study or design. For example, and not by way of limitation, a particular gene of interest, Y, improves tobacco crop yield. GUS gene fusions may be used in various ways to report on whether or not gene Y is expressed, including, but not limited to, the following. First, a recombinant construct which contains a promoter element which will result in expression appropriate for gene Y (with regard to developmental timing, tissue specificity, etc.) may be placed on the same construct as the GUS gene; expression of GUS activity should be controlled by the same promoter sequence which controls expression of Y, but may or may not be transcribed on the same RNA molecule. Downstream of Y, and separated from Y by a translational stop signal, is the GUS gene. This construct is used to create a transgenic tobacco plant. It would be impractical and overly time consuming to produce a crop of plants in order to determine whether Y were expressed or not. Instead, it would be straightforward to identify transgenic plants which may express Y by testing for GUS activity. As part of a single transcription unit with Y, GUS may only be transcribed if Y has been transcribed. Second, two constructs, one comprising Y and its appropriate promoter element, the second comprising GUS and the same promoter, may be inserted into a transgenic tobacco plant simultaneously. To identify plants which express Y, one may identify plants that express GUS, as the expression of both genes is under the control of the same promoter.

According to related embodiments, GUS gene fusions may be used to assay mutagenic potential. For example, GUS encoding sequence or a controller sequence could be engineered such that GUS would not be expressed in cells that contain the engineered gene fusion. If these cells were subjected to a mutagen, reversion of the mutation could restore GUS activity. Similar experiments could be used to study cis and trans relationships between controller elements. Likewise, inactivation of GUS expression could also be used to assay mutagenic activity. According to a further embodiment, GUS expression may be inactivated by transposon insertion; upon excision, GUS gene expression would be activated resulting in cells that would be "marked" by GUS activity. Conversely, GUS-encoding sequences could be incorporated into a transposable element; relocation of this element in the genome may be observed to effect activation of GUS expression.

The virtual lack of GUS activity in many bacteria, plants and insects renders GUS a particularly useful reporter enzyme. Furthermore, it appears that GUS itself does not significantly alter the physiology of host cell transformants, rendering it suitable for in vivo use. In the Example sections that follow, the successful use of GUS gene fusions is exemplified by expression of active GUS enzyme directed by distinct promoter elements in organisms as diverse as bacteria, nematodes, and higher plants.

In further embodiments of the invention, GUS gene fusions may be used to confer a selectable phenotype on cells. According to the current state of the art, when a collection of cells is subjected to routine DNA transfer methods, it is important to be able to select for further study those cells which have successfully incorporated the exogenous DNA. Standard methods frequently involve the co-transfer of genes for antibiotic resistance, or resistance to another compound which ordinarily would be toxic to cells. Exposure to antibiotic or toxin should kill cells that have not been successfully transformed, whereas cells containing and expressing transferred DNA sequences should survive. It has been considered, however, whether the selection agent has in fact resulted in the survival of a subpopulation of cells which not only contain express transferred DNA but which also exhibit additional phenotypic differences from the original host cell. In order to preclude this possibility, a method of selection which identifies transformants solely on the basis of expressed transferred DNA sequences may be utilized. For example, potential transformants, comprising a GUS gene fusion, may be tested for expression of GUS activity; of note, GUS may be identified within single cells. In a specific embodiment of the invention, a gene fusion may be constructed in which a GUS gene, under the control of a suitable promoter, is linked to a signal peptide; this gene fusion is used to transform cells. If expressed, GUS may be secreted from the cell via the signal peptide, and may be detected in supernatants or cloned transformants.

5.5. Utility of Beta-Glucuronidase Gene Fusions in the Manipulation of Cellular Phenotype According to the invention, GUS gene fusions may be used to manipulate cellular or organismal phenotype. In various embodiments of the invention, a β-glucuronide comprising a bioactive compound enters a cell which comprises a GUS gene fusion and is cleaved by GUS enzyme such that the bioactive compound is released and is capable of acting on the cell. The term "bioactive compound" is construed to refer to any compound which has any effect, including inductive as well as inhibitory effects, on a cell or organism, and refers to compounds including, but not limited to, growth factors, differentiation factors, hormones, antibiotics, steroid compounds, toxins, lymphokines, etc. In preferred embodiments of the invention, the bioactive compound is inactive when comprised in the glucuronide.

In various embodiments, GUS gene fusions may be used to manipulate cellular, or organism, phenotype through the action of exogenously supplied glucuronides. For example, it may be desirable to make a particular cell population, tissue, or organism selectively susceptible to a particular bioactive compound. Susceptibility may be conferred (i) by the presence of GUS enzyme, where, in nature, no GUS activity is found; (ii) by increased levels of GUS enzyme; (iii) by the presence of an altered form of GUS which is particularly active toward glucuronides comprising the bioactive compound of interest; or (iv) by increased uptake of substrate.

As an example, and not by way of limitation, it may be desirable to promote the growth of crop plants, but not the growth of weeds. Transgenic crop plants may be created which comprise a GUS gene fusion in which GUS expression is controlled by a powerful promoter. Preferably, these plants are also rendered permeable to glucuronides by expression of a transgene which encodes glucuronide permease. If these plants are sprayed with a glucuronide which comprises an auxin, the conjugated auxin will be freed by GUS activity within the plant cells, where it might subsequently act to promote plant growth. Because weeds lack endogenous GUS activity, they would be unaffected by conjugated auxin. According to a specific embodiment of the invention, exemplified in Section 10, infra transgenic plants comprising a CaMV 35 S/GUS gene fusion are selectively able to metabolize auxin supplied in the form of a glucuronide derivative.

As another example, the invention may be utilized to ablate a specific tissue or population of cells. According to particular embodiments of the invention, gene fusions may comprise GUS under the control of Z, a tissue specific promoter element. Accordingly, recombinant GUS should only be expressed in tissues in which promoter Z is active. If a transgenic organism comprising the Z-GUS gene fusion is exposed to glucuronide comprising a toxin, the toxin would only be activated by tissues expressing Z-GUS. In specific embodiments of the invention, this technique may be used to create male-sterile plants, for instance, by ensuring that Z-GUS expressed GUS activity only in anthers and pollens, or, alternatively, animal models for organ degeneration, to name only two of the numerous applications.

In related embodiments, GUS gene fusions may be constructed such that GUS is only expressed after a particular event has occurred. For example, a gene fusion may be constructed in which GUS is expressed under the control of a promoter which responds to a trans-activating factor. In specific embodiments, this trans-activating factor may be a viral transactivating factor, such that the only cells that would express recombinant GUS would be virus-infected cells. Accordingly, virus-infected cells would be particularly sensitive to glucuronide comprising an antiviral or cytotoxic agent.

Importantly, this technology may not only be applied to the treatment of viral infections in organisms which lack endogenous GUS activity, such as plants, but also organisms which do possess GUS activity, because GUS levels can be elevated to levels which exceed normal levels (thereby conferring a selective sensitivity to GUS substrates) or, alternatively, because recombinant GUS may be engineered to possess a higher or more selective activity. Selectivity may also be conferred by recombinant glucuronide permease, as discussed infra.

In further embodiments of the invention, GUS gene fusions may be used to manipulate cellular, or organism phenotype through the action of endogenously generated glucuronides. For example, in organisms, such as vertebrates, which metabolize a number of compounds including hormones, non-hormonal steroids (including cholesterol) and antibiotics to inactive glucuronides, GUS gene fusions may be used to alter the bioavailability of these compounds. By either augmenting endogenous levels of GUS or providing altered selectivity of the GUS enzyme or glucuronide permease, the gene fusions of the invention may increase or decrease the half-life of a number of biologically significant molecules.

For example, contraception may be a desirable result of increased levels of estrogen and/or progesterone, both of which are excreted via conjugation to form glucuronides. A transgenic animal comprising a GUS gene fusion transgene may express either (i) higher levels of GUS than would normally be expressed in the animal; (ii) an altered form of GUS which would be particularly effective at hydrolizing the estrogen/progesterone-glucuronide linkage; (iii) a form of glucuronide permease exceptionally adept at bringing estrogen/progesterone glucuronides into the cell; or (iv) a compartmentalized form of GUS. Endogenously produced estrogen/progesterone would thus have a longer half-life in these animals and contraception could be achieved without any exogenously administered hormone. This technology may be applied to domestic animals, such as dogs and cats. Because increased levels of estrogen or progesterone may have deleterious effects on non-reproductive organs, GUS gene fusions may desirably be expressed only in reproductive tissues, thus increasing GUS activity in estrogen/progesteone target organs at the cellular level without altering serum levels in the organism. In this embodiment of the invention, contraception could be permanent (unless, for example, GUS expression were controlled by an inducible promoter). Alternatively, hormonal levels could be manipulated to increase fecundity, as in domestic livestock. Importantly, the GUS gene fusion system may be used to temporarily alter the bioavailability of compounds endogenously incorporated into glucuronides.

Temporary alteration of glucuronide metabolism may be achieved by exploiting the symbiotic relationship between vertebrates and their intestinal flora. Typically, bioactive compounds are inactivated in the liver by glucuronidation. The resulting glucuronides are secreted into the bile ducts and then into the intestine. Intestinal bacteria use endogenous GUS to utilize glucuronides as a carbon source, and thereby release significant amount of deconjugated bioactive substance which recycles into the bloodstream. In various embodiments of the invention, the levels, activity, and specificity of GUS or alternatively of glucuronide permease in the intestinal bacteria may be altered in order to change the rate of recycling of bioactive compound. For example, and not by way of limitation, bacteria may be produced which comprise a GUS gene fusion which results in extremely high levels of GUS activity in the bacteria or GUS activity with high specific activity. If a vertebrate's intestine is populated with bacteria which express high levels of GUS, bioactive compounds will be reclycled at a higher rate and the half-life of bioactive compounds excreted via the glucuronide pathway will be extended. In this way, the half-life of antibiotics may be extended, thereby increasing the period between doses, or temporary contraception may be achieved via increased estrogen or progesterone levels to list but two of numerous examples. Alternatively, bacteria may be engineered which have lower GUS or glucuronide permease activity, thereby decreasing recycling of substances which are desirably excreted for example, ingested toxins, mutagens, etc. For example, patients with high cholesterol levels may benefit from an intestinal population of bacteria which have low levels of GUS activity and which permit the excretion of cholesterol as a glucuronide.

As discussed above, by using GUS enzyme or permease which is substrate selective, in particular embodiments of the invention the recycling of some compounds, but not others, may be altered. In preferred embodiments of the invention, bacteria comprising a GUS gene fusion further comprise a gene for resistance to a particular antibiotic; in this manner, the antibiotic may be used to eliminate the vertebrate's natural bacteria flora, and permit population by recombinant bacteria. Recombinant bacteria, in turn, may be eliminated by the use of a second antibiotic to which they carry no resistance.

It should be understood that the abovementioned examples are not limiting to the invention, but are intended only to illustrate a few of the numerous embodiments of the invention. The invention further provides for variations of these embodiments which may become apparent to one skilled in the art after reading the examples contained herein.

5.6. Utility of Glucuronide Permease

According to the invention, glucuronide permease encoding nucleic acids, under the control of a suitable promoter element, may be inserted into cells to render the cells permeable to glucuronide substrates of GUS enzyme.

The glucuronide permease gene may be used in many different organisms to transport substrates for β-glucuronidase (GUS) into cells. Because this permease activity is encoded by a single polypeptide, and because there is no subsequent modification of the permease required for its insertion into membranes or its function (by analogy with the melibiose and lactose permeases) it is reasonable to expect that expression of the permease under the control of virtually any promoter in a transgenic organism will result in the transport of β-glucuronides into cells of that organism.

In one embodiment of the present invention, the glucuronide permease gene can be transfected together with GUS as part of the same construct, or incorporated into another vector (i.e. cotransfector), such as a plasmid or a eukaryotic vector such as SV-40 (Mulligan and Berg, 1980, Science 209:1422–1427). This in turn will allow for β-glucuronidase, including fluorogenic and colorimetric β-glucuronidase substrates, to be incorporated into live, undisrupted cells, thus allowing detection of β-glucuronidase reporter gene activity in vivo, eliminating the constraints of tissue extracts and histologic procedures, and thereby providing for more general applicability of the GUS system.

In another embodiment of the present invention, the glucuronide permease gene can be introduced into cells which have endogenous β-glucuronidase activity. By altering the number of glucuronide permease molecules present at the cell membrane, permeability of the membrane to β-glucuronidase can be effected, and thus, glucuronide permease itself can function as a reporter gene and allow the metabolism of inactive glucuronides to active aglycones using endogenous β-glucuronidase. This could be applied not only to cells, but to whole organisms, to produce, for example, glucuronide permease plants (see infra).

Glucuronide permease can be produced in large amounts by inserting the gene into an active expression vector and allowing the gene to be expressed, for example, in bacteria. In one embodiment of the present invention, the glucuronide permease could be chemically or genetically linked to a ligand, which could deliver the permease for insertion into cell membranes bearing the ligand receptor. By analogy to lactose and melibiose permease, the glucuronide permease should be able to integrate spontaneously into the cell membrane. For example, glucuronide permease could be coupled to the Fc region of an immunoglobulin specific for a discrete population of mammalian cells. Upon binding to these cells, the antibody would deliver glucuronide permease for insertion into the cell membrane, thereby making a discrete population of mammalian cells increasingly permeable to β-glucuronides. In this example, selected β-glucuronides could then be used to various purposes (see infra), utilizing endogenous β-glucuronidase expressed by mammalian cells.

In another, related embodiment of the present invention, glucuronide permease could be incorporated into membrane vesicles, and thereby become inserted into the cell membrane. The membrane vesicles could contain various substances, including, but not limited to, β-glucuronide conjugated compounds.

The present invention provides for the use of glucuronide permease in altering membrane permeability to various compounds, utilizing β-glucuronide conjugates and endogenous or exogenously-supplied β-glucuronidase activity. These compounds include, but are not limited to, the following substances which may be conjugated to β-glucuronic acid to form β-glucuronides, which may be transported by glucuronide permease.

(a) Indicator substances such as histochemical indicators including napthol and napthol ASB1 and X-gluc (supra); fluorogenic substances such as 4-methyl umbelliferone and fluoroscein 3-O-methylfluoroscein, or 4-trifluromethyl umbelliferon and colormetric indicators such as resorufin, and p-nitrophenol.

(b) Catabolic substances such as cellobiuronic acid, a disaccharide which, when transported into the cell, is metabolized to, glucose by β-glucuronidase.

(c) Growth factors, such as the various peptide growth hormones, and in plants, cytokinins or auxins, gibberellins or abscisic acid.

(d) Toxic substances, such as snake venom toxins, including, according to their mode of action, cardiotoxins which cause irreversible depolarization of the cell membranes of heart muscles or nerve cells, neurotoxins which prevent neuormuscular transmission by blocking neurotransmitter receptors, and protease inhibitors which inhibit acetylcholine esterase and similar enzymes invovled in nerve transmission. Also included are phytotoxins such as ricin and abrin and bacterial toxins, fungal toxins, herbicides such as dinitrophenol derivatives, or sulfonyl ureas, etc. and chemotherapeutic agents.

(e) Various steriod hormones are excreted as conjugated β-glucuronides. Usong glucuronide permease, these hormones could be recycled, and their mechanism of action potentiated in select cells. In another embodiment of the present invention, exogenous steroid-β-glucuronides could be targeted to glucuronide permease expressing cells.

5.7. Additional Uses of the GUS System

In addition to the embodiments described above, the present invention also envisions the utilization of further aspects of glucuronide metabolism in molecular engineering of organisms. For example, the repressor encoded by the GUS operon may be utilized as a means of turning on or turning off of GUS activity in recombinant organisms, and may also be useful in conferring selectively to GUS activity toward particular substrates. Furthermore, because plants appear to lack an endogenous GUS/glucuronidation system, it is envisioned that transgenic plants may be created which express glucuronidyl transferases which may be capable of conjugating compounds including, but not limited to, herbicides, to form inactive glucuronides; such plants may be constitutively resistant to toxins such as herbicides.

Therefore, according to the invention, the repressor of β-glucuronidase expression, which has been mapped upstream of the structural gene for GUS, may be cloned by using standard techniques to "walk" upstream of the GUS structural genes and should be identifiable as an open reading frame. The repressor may be cloned and sequenced using standard techniques, expressed in an expression vector using techniques discussed in Sections 5.2 and 5.3, supra, and then tested for the ability to repress expression of GUS, for example, in bacteria which constitutively express GUS. Alternatively, the binding site for the repressor may be identified (for example, by footprinting analysis), and may thereby be used to repress GUS expression.

5.8. Useful Substrates for the Beta-Glucuronidase Gene Fusion System

Virtually any β-D-glucuronide may be used as a substrate according to the invention. A variety of glucuronides may be used in GUS assay systems, including, but not limited to, fluorescent glucuronides such as 4-trifluoromethyl umbelliferyl β-D-glucuronide, 3-cyanoumbelliferyl β-D-glucuronide, and fluoroscein β-D-glucuronide; and chromogenic substrates such as 5-bromo-4-chloro-3-indoyl glucuronide, and naphthol ASBI-glucuronide, cleaved to liberate free naphthol ASBI, then coupled to a diazo dye. As discussed supra, glucuronides comprising bioactive molecules can also be used as GUS substrates according to the invention; useful bioactive compounds include, but are not limited to, steroid hormones non-steroid hormones and factors, lymphokines, auxins, cytokinins, giberellins, toxins, vitamins, cofactors and antibiotics to name but a few.

5.9. Methods of Analysis of GUS Expression 5.9.1. Lysis and Extraction

Cells, tissues, cultures or whole organisms can be homogenized for assays in a variety of different buffers, using any method known in the art. The method of lysis and extraction may depend on the nature of the sample. Useful methods include but are not limited to the French press or sonicator for bacterial and yeast samples, and grinding with sand using a mortar and pestle for plant tissues. However, almost any other method of homogenization can be seriously considered. Small disposable pestles that fit into Eppendorf tubes (Kontes Glass) are suitable for homogenizing small pieces of tissue (e.g. leaf tissue), but are inadequate for fibrous tissue such as root and stem, or fungal and bacterial cultures. Repeated freeze-thaw cycles can be very effective at breaking open many tissues and cells, but must be approached cautiously for use in reproducibly extracting maximal enzyme activity.

5.9.2. Composition of Extraction Buffers

Any number of different extraction buffers may be utilized; preferably, a buffer system should be devised to address some of the characteristics of the GUS enzyme and the properties of extracts from the host organism. One extraction buffer that has been found to work well for plant, fungal and bacterial studies is described in Table I. The rationale for this particular extraction buffer is set out below.

TABLE I

| GUS Extraction Buffer (11) | Stock Solutions | Volumes |
| --- | --- | --- |
| 50 mM NaHPO$_4$, pH 7.0 | 1M NaHPO$_4$, pH 7.0 | 50 ml |
| 5 mM dithiothreitol (DTT) | 1M DTT in H$_2$O | 5 ml |
| 1 mM Na$_2$EDTA | 0.5M Na$_2$EDTA, pH 8.0 | 2 ml |
| 0.1% Sodium Lauryl Sarcosine | 10% Sarcosyl | 10 ml |
| 0.1% Triton X-100 | 10% Triton | 10 ml |
| H$_2$O | | 923 ml |

The phosphate is present to maintain the pH at or around neutrality, where GUS is fully active and stable, and as an ionic contribution. Other buffers are likely to function at least as well, with the advantage of not precipitating $Ca^{2+}$ from added media. Tris and HEPES do not appear to affect GUS activity adversely, although Tris has a very poor buffering capacity in the pH range of maximal GUS activity (5.5–7.5).

Dithiotreitol may be added to help maintain the sulfhydryl groups of GUS in a reduced state. This may be important to achieve and maintain maximum GUS activity. Higher concentrations also function very well, as does β-mercaptoethanol at 10–100 mM concentrations. β-mercaptoethanol is not as strong a reducing reagent as DTT, and because of its volatility may not be preferred. Some plant extracts are highly oxidizing, and so incubation with excessive β-mercaptoethanol or DTT on ice after extraction may help to reactivate any GUS that has become reversibly oxidized. It has occasionally been observed that assays of freshly prepared extracts may give a somewhat lower GUS activity that does not always show linear kinetics. This may be due to the time-dependence of sulfhydryl reactivation by reducing agents. This lag is longer with low concentrations of β-mercaptoethanol and progressively shorter with higher concentrations, or with stronger reducing agents, such as DTT. Inclusion of DTT at 5 mM or higher usually results in full activity almost instantaneously upon extraction.

GUS does not appear to require any ionic cofactors, but it is inhibited to various degrees by certain divalent metal cations. Accordingly, it may be preferable to include EDTA as a prophylactic measure to chelate these ions. Additionally, various oxidation reactions in plant extracts, which may cause browning and accumulation of other colored and inhibitory substances, require divalent cations, and may be inhibited by EDTA. Higher concentrations are not found to be inhibitory to GUS. For subsequent analysis of DNA concentration in the extract by fluorogenic methods (Labarca, C. and Paigen, K., 1980, Anal. Biochem. 102:344–352; Jefferson et al., 1987, supra), it is preferable to maintain an adequate concentration of EDTA to chelate $Mg^{2+}$ ions required for DNAse action, so that the integrity of the DNA may be preserved.

The detergents Triton X-100 and Sarcosyl may be included to increase the efficiency of extraction by helping to lyse cells and subcellular organelles, and to prevent aggregation of the enzyme. Triton effectively lyses organelles such as chlorplasts (e.g. Kavanagh et al., 1988, Molec. Gen. Genet. 215:38–45). Nuclei are efficiently lysed by Sarcosyl but not by Triton, so if a DNA measurement is planned, inclusion of Sarcosyl is recommended. GUS does not appear to be adversely affected by these detergents in modest concentrations. SDS at low concentrations also appears to be tolerated. Triton X-100 has been reported to have an adverse effect on the subsequent assay of GUS using resorufin β-glucuronide by contributing an endogenous fluorescence at long wave lengths.

5.9.3. Protease Action on GUS

GUS is remarkably resistant to protease action, with a very long half-life in living cells and in most extracts, but if proteases are a potential problem, due te unusual circumstances such as proteolytically sensitive gene fusions, PMSF (phenylmethyl sulfonyl fluoride—a potent inhibitor of serine proteases) at a final concentration of at least 2 mM may be included in the extraction buffer. Other proteinase inhibitors such as leupeptin (1 mM) and aprotinin (100 μg/ml) have also been used successfully (Kavanagh et al., 1988, supra). Substantially more proteinase K appears to be required to destroy GUS activity in vitro than seems to be necessary for many other proteins.

5.9.4. Storage of Extracts

Extracts may be quickly frozen in liquid nitrogen and stored at −70° C., with no loss of activity for a long time (a year at least), and at 4° C. with very little loss. Slow freezing to −70° C. may be adequate for storage, but evidence suggests caution in this mode of freezing. It is preferable that initial experiments on test samples be carried out before committing to a particular method of storage. Avoid storage at −20° which appears to cause a rapid decrease in enzyme activity. However, tissues stored at −20° C. for a few days do not seem to lose significant GUS activity.

5.9.5. Treatment of Extracts to Reduce Endogenous Fluorescence or Absorption

Tissues or cells that are high in endogenous light-absorbing or fluorescent compounds or that produce high levels of polyphenolics that might inhibit subsequent analysis can be extracted in GUS extraction buffer with polyclar AT (insoluble polyvinyl pyrollidone) which adsorbs polypphenols and ligines, followed by a brief spin-column of Sepharose CL6B, Sephadex G-25, or a comparable resin to eliminate almost all polyphenolics and low-molecular weight fluorescent contaminants from the extract. The routine use of spin-columns may be extended to microtiter plate spin columns as well, to process large numbers of extracts.

5.9.6 β-Glucuronidase Assays

Detection of β-glucuronidase activity, like all enzyme measurements, depends on the availability of substrates for the enzyme which, when acted on by the enzyme, liberate a product that is distinguishable from the substrate. A substrate that is designed to maximize sensitivity of detection of the enzyme should, preferably, have several characteristic properties. Optimally, there should be a method of detecting the product very specifically; the substrate should be cleaved only by the enzyme under study, with minimal spontaneous cleavage, and the signal to noise ratio of the method of detection should be as high as possible. In addition, one should consider whether quantitation of the signal will be important, and whether a direct relationship between product formation and enzyme activity will exist under the conditions of assay.

Quantitative enzyme assays may preferably be done in extracts, where the conditions of assay can be carefully controlled, and optimized to give reliable and accurate results. However, in working with multicellular organisms, where it is becoming increasingly apparent that differences in gene action between neighboring cells must be resolved, it is also essential to have qualitative enzyme assay methods in which the product is localized to the site of activity. This will therefore indicate the cells/tissues/colonies in which GUS—and presumably the GUS gene fusion—is active, and allow discrimination between neighboring sites that differ in their activity. Ideally, spatial localization and restriction of product should also be quantitative.

Quantitative measurements of GUS activity performed in extracts may use absorption or fluorescence methods. Although the possibility exists for fluorescent methods for GUS that will localize the fluorescent product at the site of enzyme activity, all the currently available methods for GUS histochemistry employ light absorption methods (color deposition).

5.9.6.1. Fluorogenic Assays

Detection of fluorescent molecules offers a very high signal-to-noise ratio because the incident excitation light does not impinge on the detection apparatus, and has a spectrum distinct and separable from that of the emission. The use of fluorescence measurements to detect enzyme activity usually gives two to four orders of magnitude (100–10,000X) greater sensitivity than methods that rely on spectrophotometric determination of product concentration by absorption. Absorption techniques measure a small difference between two large values, whereas fluorescence techniques measure a small difference between two large values, whereas fluorescence techniques measure an absolute value over an arbitrarily small background. Whether the detection apparatus is a quantitating optical device such as a spectrophotometer, or the human eye, the signal to noise ratio is the limiting factor in determining the levels of product detectable. For a reference that covers the basics of fluorescence measurements see Guilbault, G., 1973, Practical Fluorescence: Theory, Methods and Techniques, Dekker, New York.

This extreme selectivity and sensitivity of fluorescence techniques may manifest itself in several ways in GUS assays. First, the assays are remarkably fast. Because 100–1000 times less enzyme product than is required for a color production assay may be detected, results may be available 100–1000 times faster. Also, the quantity of material needed for accurate and reliable assays is substantially reduced.

Whereas absorption methods produce a value which is absolute for a given cuvette cell size, and that can be used with a knowledge of the extinction coefficient of the compound to establish a concentration of a substance according to the Beer-Lambert law, fluorescence output is proportional to excitation intensity and wavelength, and hence may not be comparable between different machines, or even on different days for the same machine without internal and reliable calibration of the machine with standard solutions. Calibration and expression of enzyme activity in terms of absolute quantities of fluorochrome produced may be very important for attaining reliable and reproducible results. It is often true that fluorescence output is proportional to the concentration of the fluorochrome, but this will depend on internal parameters, and may only apply over a particular range of concentrations. In practical terms however, these concentration ranges usually extend for at least six orders of magnitude.

Because fluorescence emission is dependent on the intensity and wavelength of the excitation light, any factors in an assay mixture which affect the available excitation intensity or wavelength will correspondingly affect the apparent fluorescence output. For instance, methylumbelliferone (MU—the product of MUG cleavage by GUS) absorbs light very effectively in the near ultraviolet range (UV) at 365 nm, and emits with a high quantum efficiency at 455 nm—in the blue range of the visual spectrum. In concentration extracts made from plant leaves, there is a significant level of chlorophyll, which has absorption maxima around 400 nm, but with a broad spectral distribution; there appears to be significant absorption at both 365 nm and at 455 nm. Because chlorophyll absorbs some fraction of the excitation light, that light is not available to excite the fluorochrome product of the GUS reaction, MU. Hence the intensity of the excitation light that is available to excite the MU may be reduced, and the fluorescence of the MU in the sample lowered. In addition, the chlorophyll can absorb some of the emitted fluorescent light from the MU (at 455 nm), thereby reducing further the apparent fluorescence of the MU. This phenomenon is called quenching. Quenching of fluorescence in extracts may be a problem if one is unaware of it. However, it is a simple matter to control and eliminate quenching, either by reducing the concentration of extract, eliminating the absorbing and quenching molecules from the extract prior to assaying (e.g. by a spin-column) or by performing internal calibrations with known quantities of MU in the same extract conditions as the assay.

If background activity occurs, it may be tracable to one of several potential sources. Often the background is intrinsic fluorescence that has nothing to do with GUS, but simply shows the levels of endogenous fluorescent compounds. For example, occasionally callus, wounded plant cells (such as protoplasts that have been treated with polyethylene glycol or electroporated) and tissues such as root, accumulate fluorogenic compounds (presumably secondary products, intermediates in lignin biosynthesis, and other phenylpropanoid pathway compounds). Some of these compounds are not fluorescent until after cell lysis which may release enzymes that cleave off the glycoside or other conjugate to release the free fluorochrome. This may be dealt with by the spin-column method, or by following the kinetics of fluoroescence increase.

Background may also occur when using protoplasts to study transient gene expression. Some enzyme mixtures used to prepare protoplasts have a sizeable amount of a β-glucuronidase activity. The usual flotation and KCl washes work well to eliminate all residual activity from tobacco protoplasts, but other types of cells may be more or less difficult to clean up. There are also reports that some cell types, especially upon lengthy incubation with protoplasting enzymes, endocytose material from the medium. If this occurs, only the appropriate controls may minimize the background, as washing may not help.

Another source of background may be the mutability of chemicals. When one performs extremely lengthy assays (overnight or longer) with very concentrated extracts, there is a likelihood that substrate may be converted into another compound, and then cleaved or metabolized to produce a fluorescent signal. This possibility may arise for any chemical reaction, but is best dealt with by using enzyme kinetics.

An additional potential problem is that bacterial GUS encoding genes may be inducible by incubation with MUG. Hence, long assays of material that is "contaminated" with bacteria may cause a bona fide GUS activity to develop. Contamination of this kind may be unavoidable, even with very clean tissues, as there may be endogenous bacterial and fungal populations in almost any plant. It may therefore be prudent to incorporate 0.02% $NaN_3$ in all lengthy assays to avoid this potential problem.

An additional and sometimes very useful technique is to use the specific β-glucuronidase inhibitor saccharolactone (Levvy, G. A., 1952, Biochem. J. 52:464)(Sigma S-0375, saccharic acid 1-4 latone, glucaric acid 1-4 lactone; glucarolactone) to corroborate the GUS-dependence of the fluorescence increase. This inhibitor will eliminate glucuronidase activity at concentrations less than one millimolar, but the compound is unstable at neutral pH, so that care should be exercised during prolonged assays. Because of this instability, it is preferable to use saccharolactone at up to 5 mM for assays up to half an hour. Alternatively, the reaction and the inhibited reaction may preferably be performed at pH 6.0 or below. GUS activity should not be affected by these conditions and saccharolactone is more stable at acid pH.

If the intrinsic fluorescence of the extract is a serious problem limiting sensitivity, one may either extract the fluorescent compounds prior to analysis (see above) or use another fluorogenic substrate.

Resorufin glucuronide, when hydrolyzed by GUS, yields resorufin, a phenoxazine derivative which has an extraordinarily high extinction coefficient and quantum efficiency, and excitation (570 nm) and emission (590) maxima conveniently in a range where plant tissue does not heavily absorb or fluoresce. These wavelengths are well separated by filter sets designed to optimize detection of the common fluorochrome rhodamine, making resorufin a useful fluorochrome for microscopic analysis, or analysis using fluorimeters without monochromators. It fluoresces maximally at neutral pH, with a $pK_a$ of about 5.8, making it unnecessary to stop the reaction. Because of the tendency of resorufin to be reduced to a non-fluorescent form, it may be preferable to omit DTT or β-mercaptoethanol from the reaction mix. This tendency to be affected by redox potential, and the price of the substrate are the principle disadvantages to the use of resorufin glucuronide.

4-Trifluoromethylumbelliferyl β-D-glucuronide is a very sensitive substrate for GUS. The fluorescence maximum is close to 500 nm—bluish green, where very few plant compounds fluoresce or absorb. TFMUG also fluoresces much more strongly near neutral pH, allowing continuous assays to be performed more readily than with MUG. Importantly, TFMUG may be used as a fluorescent indicator in vivo.

Substitution of the umbelliferone ring system in the 3-position generally results in fluorochromes with a reduced $pK_a$, hence better fluorescence at neutral pH. In addition, many of these substitutions, such as 3-cyanoumbelliferyl β-D-glucuronide also have a higher extinction coefficient—in this case 3–4 times higher than MUG (Sherman, W. R. and Robins, E., 1986, Anal. Chem. 40:803–805).

Fluorescein is perhaps the most widely used fluorochrome in biology. It fluoresces very well in living cells (Rotman, B. and Papermaster, B. W., 1966, Proc. Natl. Acad. Sci. USA 55:134–141), and is excited and emits at wavelengths that are spectrally neutral in plants. The mono and di-glucuronides of fluorescein may be used as reagents for in vivo GUS analysis.

5.9.6.2. Spectrophotometric Assay

The currently preferred substrate for spectrophotometric measurement is p-nitrophenyl β-D-glucuronide, which when cleaved by GUS releases the chromophore p-nitrophenol. At a pH greater than its $pK_a$, (around 7.15) the ionized chromophore absorbs light at 400–420 nm, giving a yellow color. Good color development can occur at the pH of the GUS reaction (7.0) but is enhanced and saturated by alkalinization of the reaction mixture. Perhaps the greatest advantage of using p-nitrophenol for spectrophotometric assays is the ability to monitor the progress of the reaction continuously, and then to terminate the reaction by alkalinization when it has proceeded sufficiently.

Unfortunately, much plant tissue is rich with compounds that absorb at the maximum wavelength of p-nitrophenol. Pigmented extracts can often be clarified and effectively decolorized prior to assay by passage through a spin-column of Sepharose CL6B. This treatment may be used to remove low or medium molecular weight chromophores that are not tightly bound to large macromolecules. Alternatively, other chromogenic substrates may be used.

The chromogenic substrate phenophthalein β-D-glucuronide is widely used; phenolphthalein is a deep red chromophore under alkaline conditions. This substrate is not in wide use now, due in part to its expense and to he very low relative $V_{max}$ for E. coli GUS (about 30 times lower than that for p-nitrophenyl-β-D-glucuronide) (Tomasic and Keglevic, 1973, supra), but it can still be a useful compound under conditions where the yellow of p-nitrophenol is inappropriate or difficult to detect. Phenolphthalein β-glucuronide does not induce the GUS operon of E. coli, whereas p-nitrophenyl-β-glucuronide induces the operon very well. Hence use of p-nitrophenyl β-glucuronide in bacterial cultures will both induce GUS and permease, and assay their function in vivo. This should be remembered when performing assays using p-nitrophenyl glucuronide (or methylumbelliferyl glucuronide or 5-bromo-4-chloro-3-indolyl glucuronide) on extracts or tissues that may have *E. coli* or other GUS+ bacteria as contaminants.

The spectrophotometric assay is very straightforward and moderately sensitive (Jefferson et al., 1986, Proc. Natl. Acad. Sci. USA 86:8447–8451). Because of the remarkable stability of GUS, one can enhance the sensitivity quite significantly by using very long assays (overnight assays may preferably be used to provide linear, reproducible results). The assay is also inexpensive, easy to automate and easy to quantitate without sophisticated instrumentation. Its limitations are the intrinsic lack of sensitivity of methods based on absorption of light (which measure a small difference in two large numbers), and the problems caused by light absorption by pigments in extracts. This assay may be automated using commercially available ELISA plate readers and microtiter equipment.

For very long assays (a few hours or longer), it is preferable to add 0.02% $NaN_3$ to prevent microbial growth or induction of microbial GUS, and 100–200 μg.ml BSA (bovine serum albumin) to stabilize the enzyme and with endogenous proteases and oxidizing agents.

5.9.7. Histochemical Assays of GUS

Detailed description of laboratory methods for histological and microscopic manipulation of plants, including preparation fo materials, sectioning tissues by hand, and microscopic analysis is given by O'Brien, T. P. and McCully, M. E., 1981, The Study of Plant Structure: Principles and Selected Methods. Termarcarphi Pty. Ltd., Melbourne, Australia. Microscopic analysis of plant tissues generaly involves the preparation of thin sections of material that can transmit a certain degree of light, and hence information about the specimen. When a live organism is killed and tissue sections are generated for microscopic analysis, many changes occur within the specimen that do not generally reflect the state of the living system. Cell contents leak out and mix with each other, ultrastructure is altered, degradative enzymes begin to destroy the macromolecular components, and chemical changes occur. Fixation is the compromise that must be reached to minimize this perturbation. If it were possible to maintain the cellular contents within the cell, that is, fix them, but not lose their biological activity, and if the cellular and subcellular architecture of the living specimen could be effectively maintained, we would be able to examine the biological activity in situ, and make useful inferences about the structure and function of the live organism. However, in treating a tissue or tissue section with a chemical compound designed to cross-link or coagulate proteins and other macromolecules, there is clearly a large potential for distortion of the natural specimen. Whereas a heavily-fixed specimen may retain excellent morphology, it may have little, if any remaining biological or enzymatic activity. Therefore, achieving a suitable balance between the preservation of morphology and the preservation of enzyme activity should be the ultimate aim of a fixation protocol. Clearly this will have to be determined empirically. However, a sound understanding of both the chemistry of fixation, and the properties of the specimen and enzyme (i.e., GUS) is invaluable.

Fixation conditions will vary with the fixative, the sample, the tissue, the cell-type, its permeability to the fixative and other variables of each experiment.

Glutaraldehyde effectively cross-links proteins and other macromolecules, but does not easily penetrate leaf cuticle although it is immediately taken up through cross-sections. GUS seems to be relatively sensitive to inactivation by gluaraldehyde treatment. Formaldehyde is a more gentle fixative than glutaraldehyde for preservation of GUS activity; it penetrates most plant tissues very well, and can be used for longer periods. Although glutaraldehyde is very effective at preserving structures in specimens, it is, for the same reasons, a very potent agent for inactivating enzymes, including GUS.

For treatment of protoplasts, which present very little permeability barrier to fixatives, 1% formaldehyde in 0.3–0.6M mannitol, 10 mMMES, pH 5.6 for 30–60 minutes at 0°–4° C. may be used. This should be followed by several washes for 10–15 minutes each, usually in phosphate buffer and/or osmoticum, to remove fixative. Almost all starting GUS activity should be maintained under these conditions, although this may be measured with suitable controls for each new situation.

For fixation of other plant tissues, 1–2% formaldehyde (prepared by dilution of reagent grade 37T formalin solution) in a 50 mM $NaHPO_4$ buffer at ph 7.0, containing 0.05% Triton X-100 may be used. The Triton X-100 serves to help wet the surface of the specimen, aiding in uptake of the fixative.

The best substrate currently available for histochemical localization of β-glucuronidase activity in tissues and cells is 5-bromo-4-chloro-3-indolyl glucuronide (X-Gluc) (Holt, S. J. and Withers, R. F. J., 1958, Proc. Roy. Soc. B. 148:520–534; Anderson, F. B. and Leaback, D. H., 1961, Tetrahedron, 12:236–239; Pearson, et al., 1963, Lab. Invest. 12:1249–1259; Pearson, et al., 1967, Lab. Invest. 17:217–224; Yoshida et al., 1975, Chem. Pharm. Bull. 23:1759; Jefferson et al., 1986, Proc. Natl. Acad. Sci. USA 86:8447–8451). This substrate gives a blue precipitate at the site of GUS enzyme activity. There are numerous variables that affect the quality of the histochemical localization, including all aspects of tissue preparation and fixation as well as the reaction itself.

It is worthwhile understanding the nature of the reaction to better control the variables. The product of glucuronidase action on X-Gluc is not colored. Instead, the indoyl derivative produced must undergo an oxidative dimerization to form the very insoluble and highly colored indigo dye, 5,5'-dibromo 4,4'-dichloro indigo. This dimerization is stimulated by atmosheric oxygen, and may be enhanced by using an oxidation catalyst such as a $K^+$ ferricyanide/ferrocyanide mixture (Holt and Withers, 1958, supra; Lojda, 1970, Histochemie 23:266–288; reviewed in Pearse, 1976). Without such a catalyst, the localized peroxidases may enhance the apparent localization of glucuronidase. One should not get false positives, but the relative degree of staining may not necessarily reflect the concentrations of glucuronidase.

An alternative histochemical assay for GUS uses naphthol ASBI-glucuronide, cleaved to liberate the free naphthol ASBI, then coupled to a diazo dye.

Incubate the formaldehyde or glutaraldehyde fixed tissue or whole mounts in 0.1M NaPO4 pH 7.0 with 1 mM Napthol ASBI glucuronide in a moist chamber at 37° C. For very low amounts of enzyme lengthy incubation of activity due to diffusion of the primary reaction product. The specimen may then be washed in phosphate buffer and coupled using a fresh solution of diazotized dye in phosphate buffer. Postcoupling with a 1–5 mg/ml solution of Fast Garnet GBC in phosphate buffer, pH 7, produces a result after as little as thirty second coupling, but many different coupling agents may be used. There is a voluminous literature about these histochemical methods as applied to mammalian glucuronidases (reviewed in Pearse, 1976, supra).

The GUS substrates and assays described herein are only a few of the examples of substrates and assays useful in conjunction with the GUS gene fusion system, and are not limiting of the scope of the invention.

6. EXAMPLE: CLONING OF THE *ESCHERICHIA COLI* GENE FOR BETA-GLUCURONIDASE

6.1. MATERIALS AND METHODS

6.1.1. DNA MANIPULATION

Restriction enzymes and DNA Modifying enzymes were obtained from New England Biolabs whenever possible and used as per the instructions of the manufacturer. Plasmid DNA preparations were done by the method of Birnboim and Doly (Birnboim, et al., 1979, Mucleic Acids Res. 7:1513) as described in Maniatis et al. (Maniatis, et al. 1982, *Molecular Cloning: A Laboratory Manual* (Cold Spring Harbor Laboratory, Cold Spring Harbor, N.Y.)). Routine cloning procedures, including ligations and transformation of *E. coli* cells, were performed essentially as described in Maniatis, et al. 1982, *Molecular Cloning: A Laboratory Manual* (Cold Spring Harbor Laboratory, Cold Spring Harbor, N.Y.). DNA fragments were purified from agarose gels by electrophoresis onto Schleicher & Schuell NA 45 DEAE membrane (Dretzen, et al., 1981, Anal. Biochem. 112: 295–298) as recommended by the manufacturer. DNA sequences were determined by the dideoxy chain terminator method of Sanger and Coulson (Sanger et al., 1975, J. Mol. Biol. 95:441) as modified by Biggin et al. (Biggin, et al., 1983, Proc. Natl. Acad. Sci. USA 80: 3963–3965). Oligonucleotide primers for sequencing and site-directed mutagenesis were synthesized using an Applied Biosystems DNA synthesizer, and purified by preparative polyacrylamide gel electrophoresis. Site directed mutagenesis was performed on sDNA obtained from pEMBl derived plasmids, essentially as described in Zollen et al. (1982), Nucl. Acids Res..1.0:6487–6500). The strain used for routine manipulation of the uidA gene was RJ21, a recA derivative of JM83 (Viera, et al., 1982, Gene 19:259–268) generated by P1 transduction. Strain PK803 was obtained from P. Keumpel of the University of Colorado at Boulder, and contains a deletion of the manA–uidA region. Plasmid vectors pUC7, 8 and 9 (Herrera-Estrella, et al., 1983, EMBO J. 2:987–995) and pEMBL (Dente, et al., 1983, Nucleic Acids Res. 11:1645) have been described.

6.1.2. PROTEIN SEQUENCING AND AMINO ACID ANALYSIS

Sequence analysis was performed by Dr. A. Smith of the Protein Structure Laboratory, University of California, Davis, using a Beckman 890M spinning-cup sequenator. Amino acid composition was determined by analysis of acid hydrolysates and purified beta-glucaronidase on a Beckman 6300 amino acid analyser.

6.1.3. PROTEIN ANALYSIS

Protein concentrations were determined by the dye-binding method of Bradford (Bradford, 1976, Anal. Biochem. 72:248) using a kit supplied by BIO-RAD Laboratories. Sodium dodecyl sulphate-polyacrylamide gel electrophoresis (SDS-PAGE) was performed using the Laemmli system (Laemmli, 1970, Nature 227:680).

6.1.4. BETA-GLUCURONIDASE ASSAYS

Glucuronidase was assayed in a buffer consisting of 50 mM $NAPO_4$, pH 7.0, 10 mM R-ME, 0.1% Triton X-10, 1 mM p-nitrophenyl beta-D-glucuronide. Reactions were performed in one ml volumes at 37° C., and terminated by the addition of 0.4 ml 2.5M 2-amino-2-methyl propanediol. p-Nitrophenol absorbance was measured at 415 nm. Routine testing of bacterial colonies for beta-glucuronidase activity was done by transferring bacteria with a toothpick into microtiter wells containing the assay buffer. The histochemical substrate 5-bromo, 4-chloro, 3-indolyl beta-D-glucuronide (analogous to the beta-galactosidase substrate X-gal) is commercially available (Research Organics Inc., Cleveland, Ohio), and is found to be an excellent and sensitive indicator of beta-glucuronidase activity in situ when included in agar plates at a concentration of 50 μg/ml.

6.1.5. PURIFICATION OF BETA-GLUCURONIDASE

Figure 1:
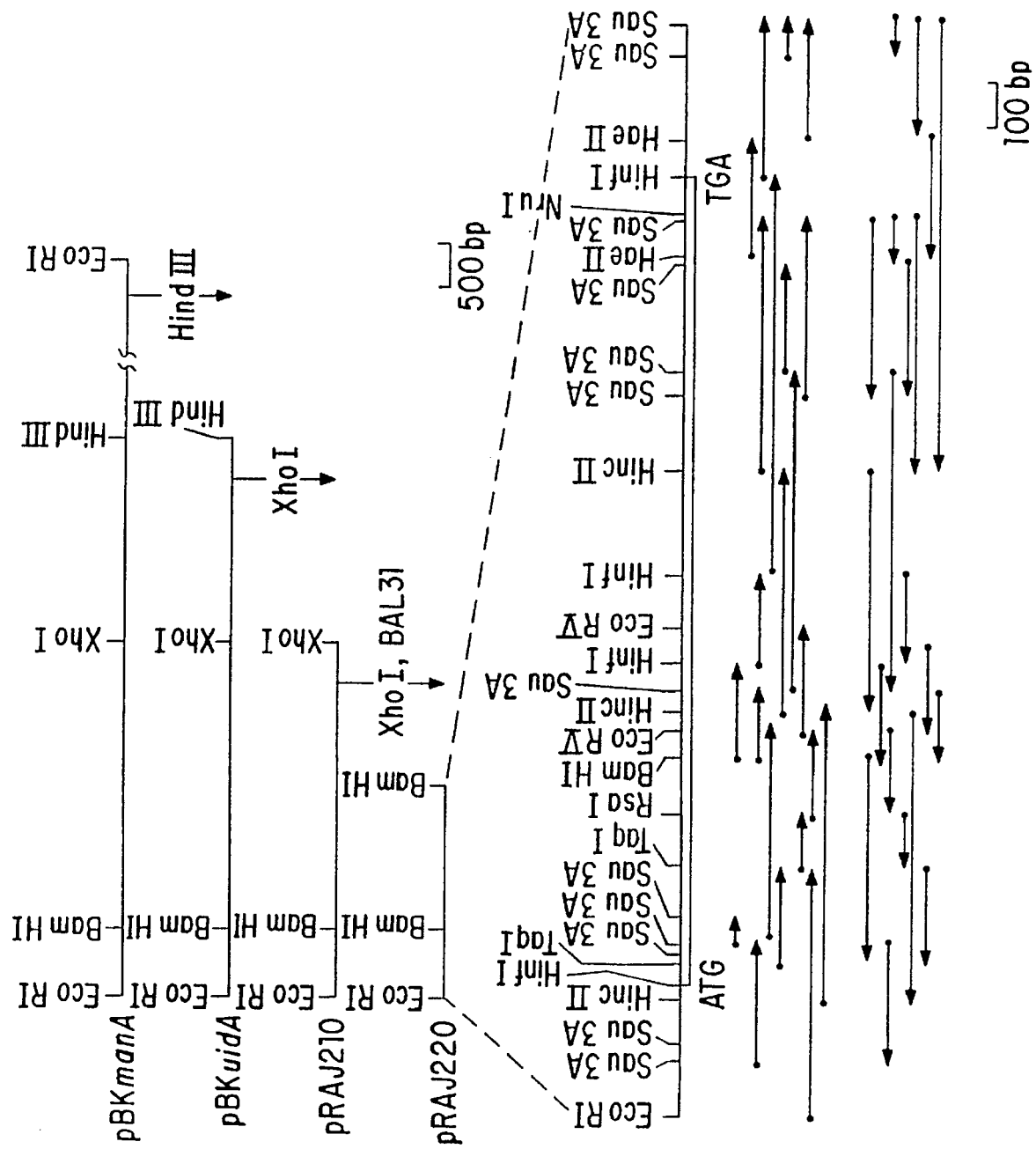
FIG. 1 illustrates subcloning and strategy for determining the nucleotide sequence of the uidA gene.

Beta-glucuronidase was purified by conventional methods from the strain RJ21 containing the plasmid pRAJ210. FIG. 1 illustrates subcloning and strategy for determining the nucleotide sequence of the uidA gene. Briefly, pBKuidA was generated by cloning into pBR325. pRAJ210 and pRAJ220 were generated in pUC9, with the orientation of the uidA gene opposite to that of the lacZ gene in the vector. The sequence was determined from both strands for all of the region indicated except from nucleotide 1 or 125. The orientation of the coding region is from left to right.

6.2. RESULTS

6.2.1. SUBCLONING AND SEQUENCING OF THE uidA GENE

The starting point for the subcloning and sequencing of the beta-glucuronidase gene was the plasmid pBKuidA shown in FIG. 1. pBK uidA has been shown to complement a deletion of the uidA–manA region of the *E. coli* K-12 chromosome restoring beta-glucuronidase activity when transformed into the deleted strain, PK803. The strategy for the localization of the gene on the insert is shown in FIG. 1.

A restriction map of the insert was obtained, and various subclones were generated in the plasmid vector pUC9, and tested for their ability to confer beta-glucuronidase activity upon transformation of PK803. The intermediate plasmid pRAJ210 conferred high levels of glucuronidase activity on the deleted strain, and was used for the purification of the enzyme. Several overlapping subclones contained within an 800 base pair (bp) Eco RI—Bam HI fragment conferred high levels of constitutive beta-glucuronidase production only when transformed into a $uidA^+$ host strain, and showed no effect when transformed into PK803.

It is surmised that the 800 bp fragment carried the operator region of the uidA locus, and was possibly titrating repressor to give a constitutively expressing chromosomal $uidA^+$ gene. With this information to indicate a probable direction of transcription, and a minimum gene size estimate obtained from characterization of the purified enzyme, a series of BAL 31 deletions were generated from the Xho I site of pRAJ210. The fragments were gel purified, ligated into pUC9 and transformed into PK803. The resulting colonies were then assayed for beta-glucuronidase activity.

The smallest clone obtained that still gave constitutive levels of beta-glucuronidase was pRAJ220, which contained a 2.4 kilobase pair (kb) insert. Subclones of this 2.4 kb fragment were generated in M13mp8 and mp9 and their DNA sequence was determined as illustrated in FIG. 2.

FIG. 2 shows the DNA sequence of the 2439 bp insert of pRAJ220, co-tailing the beta-glucuronidase gene. The arrows before the coding sequence indicate regions of dyad symmetry that could be recognition sequences for effector molecules. The overlined region is the putative Shine/Dalgarno sequence for the uidA gene, while the brackets indicate two possible Pribnow boxes. All of the palindromic regions fall within the smallest subcloned region (from the Sau 3A site at 166 to the Hind I site at 291) that gave constitutive genomic expression of uidA when present in high copy in trans, consistent with their proposed function as repressor binding sites. The terminator codon at 2106 overlaps with an ATG that may be the initiator codon of a second open reading frame, as indicated (see Discussion).

6.2.2. MANIPULATION OF THE uidA GENE FOR VECTOR CONSTRUCTION

The plasmid pRAJ220 contains the promoter and operator of the *E. coli* uidA locus, as well as additional out-of-frame ATG codons that would reduce the efficiency of proper translational initiation of eukaryotic systems (Kozak, 1983, Microbiol. Rev. 47:1–45). It was necessary to remove this DNA to facilitate using the structural gene as a reporter module in gene fusion experiments. This was done by cloning and manipulating the 5' region of the gene separately from the 3' region, then rejoining the two parts as a lac-Z:uidA fusion that showed beta-glucuronidase activity under lac control. The resulting plasmid was further modified by progressive subcloning, linker additions and site-directed mutagenesis to generate a set of useful gene module vectors. These manipulations are illustrated by reference to FIG. 3, which shows GUS gene module vectors.

Figure 3:
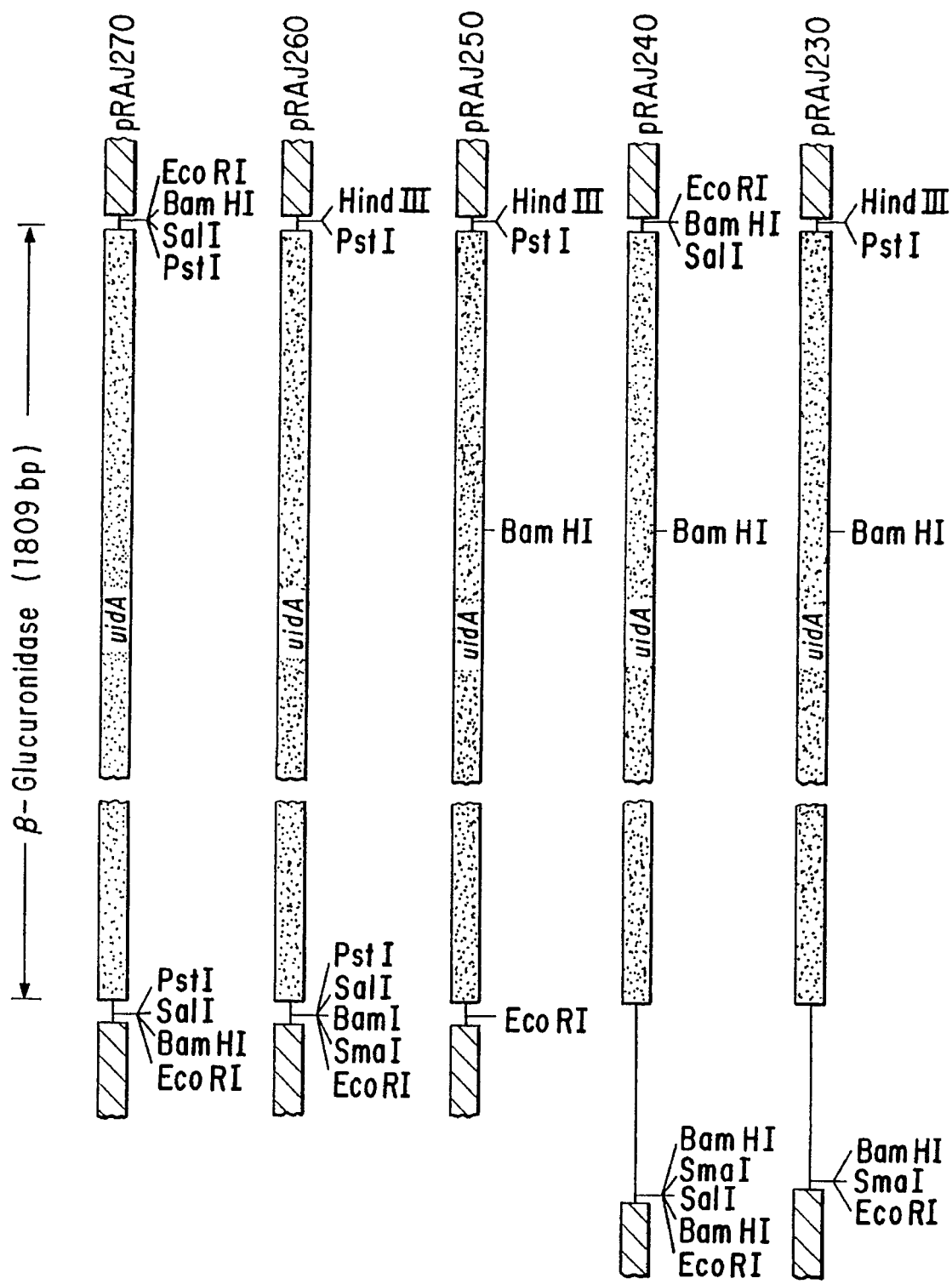
FIG. 3 illustrates GUS gene module vectors.

As illustrated in FIG. 3, pRAJ220 (see FIG. 1) was digested with Hind I, which cleaves between the Shine/Dalgarno sequence and the initiator ATG, the single-stranded tails were filled in, digested with Bam HI and the resulting 515 bp fragment was gel purified and cloned into pUC9/Hind II and Bam HI. This plasmid was digested with Bam HI and the 3' region of the uidAgene carried on a 1.6 kb Bam HI fragment from pRAJ220 was ligated into it. The resulting plasmid, pRAJ230, showed IPTG inducible GUS activity when transformed into JM103. pRAJ230 was further modified by the addition of Sal 1 linkers to generate pRAJ240, an in-frame lacZ:uidA fusion in pUC7. pRAJ230 was digested with Aat II, which cuts 45 bp 3' to the uidA translational terminator, the ends were filled, digested with Pst I, and the resulting 1860 bp fragment was gel purified, and cloned into pEMBL9/Pst I and Sma I. The resulting plasmid, pRAJ250, is an in-frame lacZ:uidA fusion. The Bam HI site that occurs within the coding region at nucleotide 807 was eliminated by oligonucleotide-directed mutagenesis of single-stranded DNA prepared from pRAJ250, changing the Bam HI site from GGATCC to GAATCC, with no change in the predicted amino acid sequence. The clone resulting from the mutagenesis, pRAJ255, shows normal GUS activity, and lacks the Bam HI site. This plasmid was further modified by the addition of a Pst I linker to the 3' end and cloned into pEMBL9/Pst I, to generate pRAJ260.

6.2.3. PURIFICATION AND PROPERTIES OF BETA-GLUCURONIDASE

Beta-glucuronidase activity in *E. coli* is induced by a variety of beta-glucuronides; methyl glucuronide is among the most effective (Stoeber, 1961, *These de Docteur es Sciences, Paris*). To determine the size and properties of the enzyme and to verify that the enzyme produced by the clone pRAJ210 was in fact the product of the uidA locus, the protein was purified from the over-producing strain, and the purified product was compared with the enzyme induced from the single genomic locus by methyl glucuronide.

Aliquots of supernatants from induced and uninduced cultures of *E. coli* C600 were analyzed by SDS-PAGE and compared with aliquots of the purified beta-glucuronidase as shown in FIG. 4. In FIG. 4 lane (a) is molecular weight standards; lane (b) is extract from uninduced C600; lane (c) is extract from C600 induced for beta-glucuronidase with MeGlcU (see reference 23); lane (d) is 0.3 μg of purified beta-glucuronidase (calculated to contain the same activity as the induced extract); lane (e) is 3.0 μg aliquot of purified beta-glucuronidase.

The induced culture of C600 shows only a single band difference relative to the uninduced culture. The new band co-migrates with the purified beta-glucuronidase, indicating that the enzyme purified from the over producing plasmid has the same subunit molecular weight as the wild-type enzyme.

The purified enzyme was analyzed for amino acid composition and subjected to eleven cycles of Edman degradation to determine the amino terminal sequence. The amino acid composition agrees with the predicted composition derived from the DNA sequence, and the determined amino acid sequence agrees with the predicted sequence, identifying the site of translational initiation and indicating that the mature enzyme is not processed at the amino terminus.

*E. coli* beta-glucuronidase is a very stable enzyme, with a broad pH optimum (from pH 5.0 to 7.5); it is half as active at pH 4.3 and pH 8.5 as at its neutral optimum, and it is resistant to thermal inactivation at 50° C.

6.3. DISCUSSION

6.3.1. MOLECULAR ANALYSIS OF THE uid LOCUS

The complete nucleotide sequence of the *E. coli* uidA gene, encoding beta-glucuronidase, has been determined. The coding region of the gene is 1809 bp long, giving a predicted subunit molecular weight for the enzyme of 68,200 daltons, in agreement with the experimentally determined value of about 73,000 daltons. The translational initiation site was verified by direct amino acid sequence analysis of the purified enzyme.

Genetic analysis of the uidA locus has shown three distinct controlling mechanisms, two repressors and a cAMP dependent factor, presumably CAP (Novel, et al., 1976, J. Bacteriol. 127:418–432). The DNA sequence determined includes three striking regions of dyad symmetry that could be the binding sites for the two repressors and the CAP protein. One of the sequences matches well with the consensus sequence for CAP binding, and is located at the same distance from the putative transcriptional initiation point as the CAP binding site of the lac promoter. It is interesting that the putative CAP Binding site overlaps one of the other palindromic sequences, suggesting a possible antagonistic effect of CAP and one or both repressors.

The sequence analysis indicates the presence of a second open reading frame of at least 340 bp, whose initiator codon overlaps the translational terminator of the uidA gene. This open reading frame is translationally active. Although a specific glucuronide permease has been described biochemically (Stoeber, 1961, *These de Docteur es Sciences*, Paris), the level of genetic analysis performed on the uid locus would not have distinguished a mutation that eliminated glucuronidase function from a mutation that eliminated transport of the substrate (Novel, et al., 1973, Mol. Gen. Genet. 120:319–335; Novel, et al., 1974, J. Bacteriol. 120:89–95). All mutations that specifically eliminated the ability to grow on a glucuronide mapped to the uidA region of the *E. coli* map, indicating that if there is a gene responsible for the transport of glucuronides, it is tightly linked to uidA. By analogy to the lac operon, it is proposed that the coupled open reading frame may encode a permease that facilitates the uptake of beta-glucuronides.

6.3.2. THE uidA GENE AS GENE FUSION MARKER

Plasmid vectors have been constructed in which the uidA structural gene has been separated from its promoter/operator and Shine/Dalgarno region, and placed within a variety of convenient restriction sites. The GUS gene on these restriction fragments contains all of the beta-glucuronidase coding information, including the initiator codon; there are no ATGs upstream of the initiator. These vectors allow the routine transfer of the beta-glucuronidase structural gene to the control of heterologous sequences, thereby facilitating the study of chimeric gene expression in other systems.

The uidA encoded beta-glucuronidase is functional with several combinations of up to 20 amino acids derived from the lacZ gene and/or polylinker sequences. Translational fusions to GUS have also been used successfully in transformation experiments in the nematode *Caenorhabditis elegans*, and in *Nicotiniana tabacum*, giving enzyme activity with many different combinations of amino terminal structures (see below).

7. EXAMPLE: EXPRESSION OF BETA-BLUCURONIDASE GENE FUSIONS IN *CAENORABDITIS ELEGANS*

Experiments have also been performed which show the expression of transformed genes in the nematode *Caenorhabditis elegans* using the gene fusion system. In particular, gene fusions between GUS and two well-characterized genes of *C. elegans*, col-1 and MSP (p3L4) have been constructed. col-1 is a collagen gene that is transcribed predominantly in embryos, and somewhat less in later developmental stages, and presumably encodes a component of the first larval stage cuticle.

The MSP gene P3L4 is a transcribed member of the major sperm protein gene family, which encodes a set of abundant, closely related 15,000M proteins that are present only in sperm. The MSP genes are transcribed only during spermatogenesis, which occurs during the fourth larval stage (L4) in hermaphrodites and in L4 and adult stages in males. Briefly, vectors consisting of the flanking regions of the collagen gene (col-1) or major sperm protein gene of *C. elegans* fused to the *Escherichia coli* uidA gene, encoding beta-glucuronidase, were microinjected into worms and found to be propagated as high-copy extrachromosomal tandem arrays. Beta-glucuronidase activity was detected in transformed lines, and the activity has been shown to be dependent upon the correct reading frame of the construction and on the presence of the worm sequences. The enzyme activity was shown to be encoded by the chimeric beta-glucuronidase gene by co-segregation analysis and by inactivation with specific antisera. Expression is at a very low level, and seems to be constitutive. Histochemical techniques have been used to visualize the enzyme activity in embryos.

7.1. MATERIALS AND METHODS

7.1.1. DNA CONSTRUCTS

The structures of the in-frame col-1:GUS fusion pRAJ321 and the in-frame MSP:GUS fusion pRAJ421 are shown in FIG. 5. In FIG. 5 both vectors are built within pUC9 (Vieira and Messing, 1982, Gene 19:259–268). The hatched region is the lac-derived sequence from pUC9. pRAJ321 is 5.8 kb and pRAJ421 is 5.5 kb. DNA manipulations were performed essentially as described in Maniatis et al. supra. pRAJ321 encodes the first 5 amino acids of the col-1 gene product plus 9 amino acids derived from linker sequences fused in-frame to the entire coding region of the *E. coli* uidA gene, and followed by the 3' intron, the translational termination codon and the polyadenylation signal from the col-1 gene. The col-1 promoter module extends from the Hinc II site 530 bp upstream from the transcription initiation site to a Bal31 generated breakpoint 14 bp into the protein coding sequence of col-1. This fragment cloned into the Hind III and Pst I sites of pUC9 is designated pRAJ301. pRAJ303 was generated by elimination of the promoter-proximal Pst site of pRAJ301, and insertion of an octameric Pst I linker. The 3' intron and the polyadenylation site from the col-1 gene are contained on a 436 bp Pvu II-Hind III fragment cloned into the Sma I site of pUC9, designated pRAJ310. The 570 bp Hind III-Sal I fragment from pRAJ301 and pRAJ303 were cloned into pRAJ310 to generate the expression vectors, pRAJ311, and pRAJ313. The MSP:GUS fusion vector pRAJ421, encodes the initiator methionine of the MSP coding sequence, 9 amino acids derived from linker sequences, and the GUS coding region, followed by the translational terminator of the MSP gene and the polyadenylation signal. The promoter module extends from a Hind III site 584 bp upstream from the initiator ATG to a Hind III site 4 bp into the coding sequence. Using a Pst I linker, this fragment was cloned into the Hind III-Pst I sites of pUC9 and is designated pRAJ401. The MSP terminator module extends from the RsaI site located 8 nucleotides upstream from the translation terminator codon, to the Hind III site, a total of about 150 bp. This fragment was shown to contain the polyadenylation site. After several manipulations, the resulting 160 bp fragment was cloned into pRAJ401 that had been digested with Bam HI and Sma I. A plasmid clone was obtained that contained the terminator in the correct orientation to the promoter, designated pRAJ411. The uidA structural gene encoding beta-glucuronidase (GUS) was transferred into the expression vectors as a 2.1 kb Sal I fragment from the plasmid pRAJ240. Clones in the correct orientation were obtained, and the nucleotide sequences at the junctions were determined using specific oligonucleotide primers complementary to the 5' coding region of the uidA gene. pRAJ421 and pRAJ321 were shown to have GUS in-frame to the MSP and col-1 initiators, respectively, while GUS in pRAJ323 was shown to be out-of-frame with respect to the col-1 initiator.

7.1.2. TRANSFORMATION WITH PLASMID DNA

Plasmid DNA was injected into the distal gonal arm of adult hermaphrodite worms at a concentration of approximately 500 μg/ml, essentially as described in Stinchomb et al., 1985, Mol. Cell. Biol. 5:3484–3496. The strain used was DH408, lacking glucuronidase activity (Horch et al., 1984, Science 223:496–498). Lines carrying the injected DNA as high-copy extrachromosomal tandem arrays were obtained from the F2 generation of the injected worms. Stability and physical properties of the tandem arrays were similar to those described in Stinchcomb et al., supra. Transformants were obtained containing either an in-frame col-1:GUS fusion (pRAJ321), an out-of-frame col-1:GUS fusion (pRAJ323), an in-frame MSP: GUS fusion (pRAJ421) or a GUS-encoding plasmid containing no worm sequences (pRAJ210).

7.1.3. FLUOROMETRIC ASSAYS

Fluorometric assays were performed in 100 µl of 50 mM-NaPO$_4$ (pH 7.0), 10 mM beta-mercaptoethanol, 0.1% (v/v) Triton X-100, 0.5 mM-4-methyl umbelliferyl beta-D-glucuronide, at 37° C., and terminated with the addition of 1 ml of 0.2M-Na$_2$CO$_3$, or 100 µl of 1M-Na$_2$CO$_3$ (for small-scale, qualitative assays). The reaction products were visualized by irradiation with 365 nm light (for qualitative assays) or by fluorescence measurements with $ex^{365nm}$ and $em^{455nm}$. Extracts were prepared from worms harvested from Petri plates, washed twice in M9 salts, resuspended in assay buffer without substrate and passed through a French pressure cell at 12,000 lb/in$^2$. Protein concentrations were adjusted to 20 mg/ml and 50 µl portions were assayed. Measurements were made on a Perkin-Elmer LS-3 spectrofluorometer. Worms from the populations harvested were shown to contain the transforming DNA at similar copy number. Extracts prepared as described above were incubated with equal volumes of either neat pre-immune serum, or affinity-purified antibody directed against purified *E. coli* beta-glucuronidase, at a concentration of 125 µg/ml for 3 hours at 4° C. Protein A-Sepharose was added, and the reactions were allowed to sit for 2 hours at 4° C. The extracts were centrifuged at 12,000 g for 5 minutes, and then assayed for beta-glucuronidase. Worms were grown for enzyme assays on the *E. coli* strain PK803 (obtained from P Kuempel) that contains a deletion of the uidA locus and has no detectable glucuronidase activity.

7.2. RESULTS AND DISCUSSION

Extracts were prepared from populations of transformed worms and assayed for the presence of beta-glucuronidase. The results are shown in FIG. 6.

Extracts from uninjected worms, worms carrying the out-of-frame col-1:GUS fusion, or pRAJ210 showed no detectable beta-glucuronidase activity, while extracts from worms carrying either the in-frame col-1:GUS fusion or the MSP:GUS fusion showed significant levels of enzyme activity. Reconstruction experiments with purified beta-glucuronidase in worm extracts indicated that the quantities of enzyme in the transformed extracts were about 1 to 2 ng beta-glucuronidase/mg soluble protein, assuming comparable turnover numbers of the native and chimeric enzymes. Consistent with the extremely low enzyme levels, no transcript was detected by Northern blot analysis, nor has an immunologically cross-reactive protein been detected in extracts, as judged by Western blots, to a sensitivity of about one part in 10$^5$.

To verify that the beta-glucuronidase activity measured in the extracts was due to the *E. coli uidA* gene product, portions of the extracts were incubated with antibody to homogeneous *E. coli* beta-glucuronidase or with pre-immune serum. Immune complexes were precipitated with Staph A-Sepharose, and the supernatant was assayed for beta-glucuronidase activity (FIG. 6). Beta-glucuronidase activity diminished only after addition of antibody directed against purified bacterial glucuronidase; preimmune serum showed no effect.

It was possible that a small number of integrated copies of the chimeric genes was responsible for the observed enzyme activity, and that the large tandem array was inactive. To test this possibility, 40 F2 worms from a transformed individual were cloned and grown to saturation on plates. Extracts were prepared and assayed for the presence of the transforming DNA by dot blot hybridization, and for beta-glucuronidase activity.

The 40 F2 worms derived from a transformant carrying the col-1:GUS fusion were cloned onto individual Petri plates, grown to saturation, harvested and washed, and the culture was split into 2 parts. Extracts were prepared for (a) fluorogenic beta-glucuronidase assays or (b) DNA dot bots. Glucuronidase assays were performed essentially as described in Connection with FIG. 6, in the wells of a Gilson tube rack at 37° C. for 4 hours, and visualized by addition of Na$_2$CO$_3$ and placing the rack on a long-wavelength ultraviolet light box. DNA dot blots were probed with $^{32}$P-labelled pRAJ210. All worm cultures that gave rise to a positive signal by DNA dot blot analysis also gave rise to glucuronidase activity, and vice versa. In several repeats of this experiment no case was observed in which strict co-segregation of the high-copy DNA and beta-glucuronidase activity was not maintained. The results are shown in FIG. 7.

The high-copy transforming DNA and the enzyme activity always co-segregated, indicating that the extra chromosomal tandem array was responsible for the beta-glucuronidase activity. Identical results were obtained from transformed populations carrying either the MSP:GUS or the col-1:GUS fusions.

To determine whether temporal regulation of the transforming DNA was occurring, extracts from staged populations of transformed worms were assayed for beta-glucuronidase activity. For both the col-1:GUS fusion and the MSP:GUS fusion, specific activity of β-glucuronidase was highest in embryos, and decreased with developmental time. The temporal pattern of expression of the col-1:GUS fusion is consistent with the available data on col-1 expression as determined by DNA dot blots in Northern blots (Kramer et al., 1985, J. Biol. Chem. 260:1945–1951). However, the pattern is also consistent with a low level constitutive expression of the chimeric gene when accounting for the near 100-fold increase in the protein content of the worm during development. In the case of the major sperm protein gene fusion, this temporal pattern of expression is inconsistent with the normal expression of MSP genes only during the L4 stage, but is consistent with constitutive expression of the chimeric gene.

In order to visualize beta-glucuronidase activity in situ, embryos were prepared from a population of worms containing the in-frame col-1:GUS fusion and an untransformed control population, fixed and assayed histochemically for beta-glucuronidase activity.

Freeze-cracked, formaldehyde-fixed (3% (w/v) paraformaldehyde in phosphate buffer (pH 7) for 3 minutes on ice) embryos from DH408 (a) or DH408 containing pRAJ321 (b) were assayed for glucuronidase activity using naphthol-ASB1 glucuronide for 6 hours at 37° C., and post-coupled with freshly prepared hexazonium pararosanalin (Fishman et al., 1965, J. Histochem. Cytochemo 13:441–447). The results are shown in FIG. 8.

In the transformed population (a), many embryos show the red precipitate characteristic of beta-glucuronidase activity, while the untransformed population (b) never shows staining. The number of positives in a given transformed population, and the intensity of staining within a population, varies considerably. Larvae and adults from a transformed population assayed under similar conditions did not show detectable staining. Perhaps because the low levels of beta-glucuronidase in the transformed populations it has not been possible to localize the activity spatially within the embryo, either histochemically or by indirect immunofluorescence or immunocytochemistry. Under the fixation conditions and lengthy assay times used to obtain histochemical staining of the transformed embryos (due to the low levels of beta-glucuronidase), the diffusion of the product may be preventing discrete localization, if indeed it is occurring.

In summary, the GUS fusion system has been used to measure chimeric enzyme levels in transformed worms. The expression of GUS in the transformed lines is dependent upon the presence of worm promoters, and on the correct reading frame of the translational fusions used. The levels of expression in these transformants are very low, but easily measured using a fluorometric enzyme assay for beta-glucuronidase, corresponding to about one part in a million of the soluble protein in a worm extract. The transforming DNA is in the form of long extra chromosomal tandem arrays, a situation that certainly does not mimic the normal in vivo condition of the genes under study. Possibly the structure of the arrays imposes characteristic restrains on the expression of genes within them, perhaps due to chromatin structure or a peculiarity of conformation. It is possible that integration of the transforming DNA will allow higher levels of expression. Methods have recently been developed to allow integration of exogenous DNA in *C. elegans*. Integration of the vectors described here into the germline of the worm may allow resolution of whether the low level, and inappropriate developmental expression of chimeric genes, is due to their extra chromosomal tandem-array structure or to some other feature of the constructions.

8. EXAMPLE: EXPRESSION OF BETA-GLUCURONIDASE GENE FUSIONS IN HIGHER PLANTS

8.1. MATERIALS AND METHODS

8.1.1. NUCLEIC ACID MANIPULATION

DNA manipulations were performed essentially as described in Maniatis et al., (1982, in "Molecular Cloning: A Laboratory Manual, Cold Spring Harbor Laboratory, Cold Spring Harbor, N.Y.). Enzymes were obtained from New England Biolabs, Boehringer-Mannheim or BRL.

8.1.2. PLANT TRANSFORMATION AND REGENERATION

Binary vectors containing CaMV-GUS fusions and rbcS-GUS fusions in *E. coli* MC1022 were mobilized into *Agrobacterium tumefaciens* LBA4404 as described in Bevan, 1984, Nucl. Acids Res. 12: 8711–8721. The integrity of the vector in *Agrobacterium* was verified by preparing DNA from *Agrobacterium* immediately before plant transformation using the boiling method (Mones and Quigley, 1981, Anal. Biochem. 114:193–201). Leaf discs of *Nicotiana tabacum*, var. Samsun were transformed using the leaf disc method (Horsch et al., 1984, Science 223:496–498), and transformed plants were selected on MS medium (Marashige and Skoos, 1962, Physiol. Plant 15:473) containing 100 μg/ml kanamycin. Plants were maintained in axenic culture on MS basal medium, 3% sucrose, 200 μg/ml carbenicillin and 100 μg/ml kanamycin, at approximately 2000 lux, 18 hour day, 26° C.

8.1.3. SOUTHERN BLOT ANALYSIS

DNA was prepared from plants by phenol extraction and ethanol precipitation of plant homogenates, followed by RNAse digestion, phenol extraction and isopropanol precipitation. Extracts were prepared from axenic tobacco plants using approximately 100 mg fresh weight of tissue ground in 500 μl extraction buffer. Ten μl of extract was incubated at 37° C. in 4 ml assay buffer and 1.0 ml aliquots were withdrawn at 0, 5, 10 and 15 minutes intervals and stopped by addition to 1 ml 0.2M $Na_2CO_3$. The fluorescence of liberated 4-MU was determined as described. Old leaves were lower, full-expanded leaves approximately 5 cm long, while young leaves were approximately 5 mm long, and were dissected from the shoot apex. All samples were taken from the same plant (either CaMV-GUS 21, SSU GUS 2 or non-transformed ) at the same time. DNA samples (10 μg were digested with restriction endonucleases, electrophoresed in an 0.8% agarose gel and blotted onto nitrocellulose (Maniatis et al., supra). Filters were hybridized with oligomer-primed, $^{32}p$ labelled GUS gene fragment (Feinberg and Vogelstein, 1984, Anal. Biochem. 137:266–269) and then washed with 0.2% SSC at 65° C.

8.1.4. SUBSTRATES

Substrates included: 4-methyl umbelliferyl glucuronide (MUG) (Sigma M-9130), 5-bromo-4-chloro-3-indolyl beta-D-glucuronide (X-GLUC) (Research Organics Inc., 4353 E. 49th St., Cleveland, Ohio, USA), resorufin glucuronide (ReG) (Molecular Probes Inc., 4849 Pitchford Ave., Eugene, Oreg., USA).

8.1.5. LYSIS CONDITIONS

Tissues were lysed for assays into 50 mM $NaH_2PO_4$ pH 7.0. 10 mM EDTA, 0.1% Triton X-100, 0.1% sodium lauryl sarcosine, 10 mM beta-mercaptoethanol (extraction buffer) by freezing with liquid nitrogen and grinding with mortar and pestle with sand or glass beads. Disposable pestles that fit into Eppendorf tubes (Kontes Glass) proved useful for homogenizing small bits of tissue (e.g. leaf). Extracts can be stored at −70° C. with no loss of activity for at least two months. Storage of extracts in this buffer at −20° C. should be avoided, as it seems to inactivate the enzyme.

8.1.6. SPECTROPHOTOMETRIC ASSAY

Reaction buffer was 50 mM $NaPO_4$ pH 7.0, 10 mM beta-mercaptoethanol, 1 mM EDTA, 1 mM p-nitrophenyl glucuronide, 0.1% Triton X-100 in 1 ml. reaction volumes, and incubated at 37° C. The reactions were terminated by the addition of 0.4 ml of 2-amino, 2-methyl propanediol (Sigma A-9754). Absorbance was measured at 415 nm against a substrate blank. Under these conditions the molar extinction coefficient of p-nitrophenol is assumed to be 14,000, thus in the 1.4 ml final volume, an absorbance of 0.010 represented about one nanomole of product produced. One unit is defined as the amount of enzyme that produces one manomole of product/minute at 37° C. This would represent about 5 ng of pure beta-glucuronidase.

8.1.7. FLUOROMETRIC ASSAY

The fluorogenic reactions were carried out in 1 mM 4-methyl umbelliferyl glucuronide in extraction buffer with a reaction volume of 1 ml. The reactions were incubated at 37° C., and 200 µl aliquots were removed at zero time and at subsequent times and the reaction terminated with the addition of 0.8 ml 0.2M $Na_2CO_3$. The addition of $Na_2CO_3$ served the dual purposes of stopping the enzyme reaction and developing the fluorescence of MU, which is about seven times as intense at alkaline pH. Fluorescence was then measured with excitation at 365 nm, emission at 455 nm on a Kontron SFM 25 Spectrofluorimeter, with slit widths set at 10 nm. The resulting slope at MU fluorescence versus time could therefore be measured independently of the intrinsic fluorescence of the extract. The fluorometer was calibrated with freshly prepared 4-methyl umbelliferone (MU) standards of 100 nanomolar and 1 micromolar MU in the same buffers. Fluorescence was linear from nearly as low as the machine can measure (usually 1 nanomolar or less) up to 5–10 micromolar 4-methyl umbelliferone.

Protein concentrations of plant extracts and a purified beta-glucuronidase were determined by the dye-binding method of Bradford (Bradford,,1976, Anal. Biochem. 72:248), with a kit supplied by BIO-RAD Laboratories.

DNA concentrations in extracts were determined by measuring the fluorescence enhancement of Hoechst 33258 dye (Laborca and Paigen, 1980, Anal. Biochem. 102:3434-352), with the calibrations performed by addition of lambda DNA standards to the extract to eliminate quenching artifacts.

8.1.8. IN SITU LOCALIZATION OF GUS ACTIVITY IN SDS POLYACRYLAMIDE GELS

Plant extracts ( 1–50 µl) were incubated with 2 volumes of SDS Sample buffer at room temperature for approximately 10–15 minutes and then electrophoresed on a 7.5% acrylamide SDS gel (Laemmli, 1970, Nature 227:680) overnight at 50 mA, or in a mini-gel apparatus (BIO-RAD) for 45 minutes. The gel was then rinsed 4 times with gentle agitation, in 100 ml extraction buffer for a total of 2 hours, incubated on ice in assay buffer (containing MUG) for 30 minutes, then transferred to a glass plate at 37° C. After approximately 10–30 minutes at 37° C., depending on the sensitivity required, the gel was sprayed lightly with 0.2M $Na_2CO_3$' and observed under long wavelength UV transillumination. Gels were photographed using a Kodak 2E Wratten filter.

8.1.9. HISTOCHEMICAL ASSAY

Sections were cut by hand from unfixed stems of plants grown in vitro essentially as described in O'Brien et al. (1981, in "The Study of Plant Structure: Principles and Selected Methods," Termarcarphi Ptx. Ltd. Melbourne, Australia) and fixed in 0.3% formaldehyde in 10 mM pH 5.6, 0.3M mannitol for 45 minutes at room temperature, followed by several washes in 50mM $NaH_2PO_4$, pH 7.0. All fixatives and substrate solutions were introduced into interstices of sections with a brief (about 1 minute) vacuum infiltration. A good review of histochemical techniques and the caveats to their utilization and interpretation can be found in Pearse (1972, in "Histochemistry: Theoretical and Applied, Third Edition, Vol. II, Churchill Livingstone, Edinburgh, pp. 808–840). Substrates for histochemical localization include indigogenic dye 5-bromo-4-chloro-3-indolyl glucuronide (X-Gluc), and napthol ASBI glucuronide.

Histochemical reactions with the indigogenic substrate, 5-bromo-4-chloro-3-glucuronide (X-gluc) were performed with 1 mM substrate in 50mM $NaH_2PO_4$ pH 7.0 at 37° C. for times ranging from 20 minutes to several hours. After staining, sections were rinsed in 70% ethanol for 5 minutes, then mounted for microscopy.

Cleavage of napthol ASBI glucuronide releases the very insoluble free napthol ASBI which is either simultaneously coupled, or post-coupled with a diazo dye to give a colored product at the site of enzyme activity. Post-coupling is preferred, as it seems to give a much lower background. Sections were incubated in 0.1M $NaH_2PO_4$ pH 7.0 with 1 mM Napthol ASBI glucuronide in a moist chamber at 37° C. for 15 minutes to 3 hours. The specimen was then washed in phosphate buffer and coupled using a fresh solution of diazotized dye in phosphate buffer. Post-coupling was performed with a 1–3 mg/ml solution of Fast Garnet GBC in phosphate buffer, pH 7, after which the sections were washed and mounted for light microscopy.

Fixation was accomplished with 2.5% glutaraldehyde in 0.1M $NaH_2PO_4$ pH 7.0 for 2–3 minutes on ice.

8.1.10. PURIFICATION OF BETA-GLUCURONIDASE

Beta-glucuronidase was purified essentially as described from *E. coli* cells containing the plasmid pRAJ210. Eight liters of cells were grown in L broth with 50 ug/ml ampicillin at 37° C. with vigorous agitation. The cells were harvested as they approached saturation, washed in M9 salts, and resuspended in about 100 ml of 100 mM $NaH_2PO_4$ pH 7.0 10 mM beta-mercaptoethanol, 50 mM NaCl, 0.2% Triton X-100 and 25 ug/ml phenylmethyl sulphonyl fluoride. The slurry was passed through a French pressure cell at 12,000 psi, and the resultant lysate was stirred on ice for 30 minutes. The lysate was spun at 10,000 × g for 30 minutes at 4° C., and the turbid supernatant was dialysed overnight against several changes of 50 mM Tris pH 7.6, 10 mM B-ME (buffer A). The dialysate was loaded onto a column of DEAE Sephacelo (2.5×40 cm) equilibrated in the same buffer, at 4° C. The column was washed with loading buffer and eluted with a 500 ml linear gradient of NaCl (0–0.4M). The combined peak fractions were concentrated in an Amicon ultrafiltration apparatus with a PM 30 membrane to a final volume of 27 ml. This volume was loaded onto a 500 ml (2.5×100 cm) Sephacryl S-200 gel filtration column, and eluted with buffer A plus 100 mM NaCl. Peak fractions were pooled and dialysed overnight against 20 mM NaOAc pH 5.0, at 4° C. The resulting pellet was dissolved in buffer A, and both pellet and supernatant were assayed for beta-glucuronidase activity and analyzed by SDS-PAGE. The supernatant contained the majority of the activity, and by gel analysis had lost nearly all of the contaminating protein (greater than 95% purity as judged by Coomassie staining) obviating further chromatography. The purified enzyme was stored in GUS extraction buffer at 4° C. The final yield was about 350 mg.

8.2. RESULTS

8.2.1. HIGHER PLANTS CONTAIN NO DETECTABLE BETA-GLUCURONIDASE ACTIVITY

Roots, stems and leaves were taken from wheat, tobacco, tomato, potato, *Brassica napus* and *Arabidopsis thaliana*. Potato tubers and seeds from wheat and tobacco were homogenized with GUS extraction buffer containing a variety of protease inhibitors such as PMSF and leupeptin. The plant extracts were incubated in a standard assay at 37° C. for 4 to 16 hours, and the fluorescence of MU was measured. Endogenous activity was below the limits of detection. Extremely lengthy assays occasionally gave low levels MU fluorescence, but the kinetics of MU accumulation were consistent with a slow conversion of the glucuronide into another form, possibly a glucoside, that was subsequently cleaved by intrinsic glycosidases. Beta-galactosidase assays performed under similar conditions on tobacco and potato extracts were off-scale (at least 10,000 times higher than the minimal detectable signal) within 30 minutes. Reconstruction experiments were performed with purified GUS added to tobacco and potato extracts to demonstrate the ability of these extracts to support beta-glucuronidase activity.

8.2.2. CONSTRUCTION OF PLASMIDS FOR TRANSFORMATION OF PLANTS WITH GUS FUSIONS

A general purpose vector for constructing gene fusions was made by ligating the coding region of GUS 5' of the nopaline synthase polyadenylation site (Bevan et al., 1983, Nat ure 304:184–187) in the polylinker of pBIN 19. This vector, pBI101 (see FIG. 9) contains unique restriction sides for Hind III, Sal I, Xba I, BamH I, and Sma I upstream of the AUG initiator codon of GUS, to which promoter DNA fragments can be conveniently ligated. The cauliflower mosaic virus 35S promoter (O'Dell et al., 1985, Nature 313:810–812) in the expression vector pROK1 (Baulcombe et al., 1986, Nature 321:446–449) was ligated into the Hind III and BamH I sites to create pBI121. Similarly the promoter from a tobacco gene encoding the small subunit of ribulosebisphosphate carboxylase small, Ntss23 (Mazur and Chui, 1985, Nucl. Acids Res. 13:2373–2386) deleted of rbcS coding sequences was fused to pBI101 to make pBI131.

FIG. 9 illustrates the structure of the expression vectors.

The lower portion of FIG. 9 shows the T-DNA region of pBI101, containing polylinker cloning sites upstream of the beta-glucuronidase gene, followed by the nopaline synthase polyadenylation site (NOS-ter). Pst I and Sph I are not unique to the polylinker. The expression cassette is within pBIN 19, giving pBI101 a total length of approximately 12 kb.

The middle portion of FIG. 9 shows chimeric CaMV 35S-GUS gene in pBI121. An 800 bp Hind III–BamH I CaMV 35S promoter fragment (Guilley et al., 1982, Cell 30:763–773) was ligated into the corresponding sites of pBI101. The mRNA initiation site is approximately 20 bp 5' of the GUS initiator codon.

The top portion of FIG. 9 shows chimeric rbcS-GUS gene in pBI101. A 1020 bp Hind III–Sma 1 fragment containing the promoter of a tobacco ribulose bisphosphate caraboxylase small subunit gene. (rbcS) was ligated into the corresponding sites of pBI101. The mRNA initiation site is approximately 55 bp 5' of the GUS initiator codon, and contains nearly the entire untranslated leader of the rbcS gene.

FIG. 9 also illustrates the differences between the three pBI101 plasmids.

8.2.3. CHIMERIC GUS GENES ARE EXPRESSED IN TRANSFORMED PLANTS

*Nicotiana tabacum* var. Samsun plants were transformed with *Agrobacterium* binary vectors (Bevan, 1984, Nucl. Acids Res. 12:8711–8721) containing transcriptional fusions of either the CaMV 35S promoter or the tobacco rbcS promoter with the coding region of GUS as shown in FIG. 9. Several kanamycin resistant plants were regenerated from each transformation.

Two rbcS-GUS transformants and two CaMV-GUS transformants were chosen for further study. First assays were made of various organs of one plant from each transformation, axenically cultured in 300 lux white light, 18 hour day, 6 hour night. Extracts were prepared from axenic tobacco plants using about 50 mg fresh weight of tissue ground in 500 ul extraction buffer. 5 μl of extract was assayed in 500 ul extraction buffer. 5 μl of extract was assayed as described in "Materials and Methods" above. Mature leaves were lower, expanded leaves approximately 80 mm long, while young leaves were approximately 5 mm long, and were dissected from the shoot apex. All samples were taken from the same plant (either CaMV-GUS 21, rbcS GUS 2 or non-transformed) at the same time. Leaf tissue was taken from a non-transformed plant for this assay, although all organs showed no GUS activity.

The results of this analysis are shown in FIG. 10, and tabulated in Table II using either of two normalization methods (see following discussion).

TABLE II

| Gene Fusion: | GUS Specific Activity | | | | |
|---|---|---|---|---|---|
| | (pmoles 4-MU/min/mg protein) | | | (pmoles 4-MU/min/mg DNA) | |
| | CaMV 35S-GUS | rbcS-GUS | untransformed | CaMV 35S-GUS | rbcS-GUS |
| Plant organ | | | | | |
| Leaf (5 mm) | 283 | 205 | <0.1 | 2,530 | 4,400 |
| Leaf (70 mm) | 321 | 1,523 | <0.1 | 5,690 | 93,950 |
| Stem | 427 | 260 | <0.1 | 13,510 | 2,650 |
| Root | 577 | 62 | <0.1 | 12,590 | 690 |

The rate data shown in FIG. 10 were converted to specific activity by measuring the protein concentration of the extracts using the Bradford reagent. The data are also presented as GUS activity per unit weight of DNA in the extract to better account for the differences in cell number between different tissues.

The plant containing a rbcS-GUS fusion (rbcS-GUS 2) exhibited a pattern of gene expression consistent with earlier studies using heterologous rbcS gene fusions (Simpson et al., 1986, Nature 323:551–554). The highest specific activity, using either protein or DNA as a denominator, was found in older leaves (about 8 cm long), with progressively less activity in very young leaves (less than 5 mm), stems and roots. The other rbcS-GUS fusion plant showed a similar pattern.

The two plants transformed with the CaMV 35S-GUS fusion displayed a pattern of gene expression distinct from that of the rbcS-GUS fusion plants. The highest levels of activity were found in roots, with similar levels in stems. GUS activity was also high in leaves, consistent with previous observations that the CaMV 35S promoter is expressed in all plant organs (O'Dell et al., 1985, Nature 313:810–812).

To verify that no significant rearrangements of the transforming DNA had occurred, a Southern blot analysis was conducted as shown in FIG. 11, which is an autoradiograph of a Southern blot of DNA extracted from transformed plants and digested with restriction endonucleases. The filter was hybridized with a $^{32}p$ labelled restriction fragment containing the coding region of the beta-glucuronidase gene. In this Figure
Lane 1. CaMV-GUS 21 EcoR I
Lane 2. CaMV-GUS 21 EcoR I & Hind III
Lane 3. CaMV-GUS 29 EcoR I
Lane 4. CaMV-GUS 29 EcoR I & Hind III
Lane 5. rbcS-GUS 2 EcoR I
Lane 6. rbcS-GUS 2 EcoR I & Hind III
Lane 7. rbcS-GUS 5 EcoR I
Lane 8. rbcS-GUS 5 EcoR I & Hind III
Lane 9. Non-transformed EcoR I
Lane 10. Non-transformed EcoR I & Hind III
Lane 11. Single copy reconstruction of GUS coding region
Lane 12. Five copy reconstruction.

Digestion of DNA extracted from all of the transformants with Hind III and EcoR I released a single internal fragment of T-DNA consisting of the nopaline synthase polyadenylation site, the GUS coding region and the promoter (CaMV35S or rbcS). RbcS-GUS transformants contained 3 copies (rbcS-GUS 2, FIG. 11, lane 6) and about 7 copies (rbcS-GUS 5, lane 8) of the predicted 3.1 kb Hind III- ECoR I fragment. Digestion with EcoR I revealed multiple border fragments (FIG. 11, lanes 5 and 7) confirming the copy number estimates deduced from the double digestions. Similarly CaMV 35S-GUS plants had multiple insertions as shown in FIG. 11 lanes 1 to 4. CaMV-GUS 21 had 3 copies of the predicted 2.9 kb fragment, while CaMV-GUS 29 had 2 copies. No hybridization of the labelled GUS coding region to untransformed plant tissue was observed (lanes 9 and 10).

8.2.4. VISUALIZATION OF GUS ACTIVITY ON SDS-POLYACRYLAMIDE GELS

Extracts of transformed plants were prepared and electrophoresed, together with negative controls and varying amounts of purified beta-glucuronidase, on an SDS-polyacrylamide gel. The gel was rinsed to reduce the SDS concentration, and then treated with the fluorogenic substrate, MUG. After the reaction had progressed sufficiently, the gel was made alkaline to enhance fluorescence, placed on a long wave UV box and photographed (FIG. 12). The gel was trans-illuminated with 365 nm light and photographed using a Kodak Wratten 2E filter. In FIG. 12,
Lane 1. Transformed plant extract—CAB-GUS fusion
Lane 2. Transformed plant extract—SSU-GUS 2
Lane 3. Transformed plant extract—CaMV-GUS 21
Lane 4. Non-transformed plant extract
Lane 5. Non-transformed plant extract plus 1 ng GUS
Lane 6. Non-transformed plant extract plus 10 ng GUS
Lane 7. Non-transformed plant extract plus 50 ng GUS GUS activity could be seen in all lanes containing purified enzyme, with a limit of sensitivity in this experiment of one nanogram. In other experiments, we have observed activity with as little as 0.2 ng. The lanes containing the SSU-GUS and CaMV-GUS fusion extracts show GUS activity that migrates with the same mobility as the purified enzyme, indicating that translation is initiating and terminating at the correct locations in the GUS sequence and that no significant post-translational processing is occurring. An additional lane was included that contained a protein fusion between part of the tobacco chlorophyll a/b binding protein and GUS that shows decreased mobility relative to purified beta-glucuronidase, as predicted. Staining of gels using the histochemical methods described below proved to be effective, but not as sensitive as the fluorogenic stain.

8.2.5. GUS ACTIVITY IN PLANTS CAN BE VISUALIZED USING HISTOCHEMICAL METHODS

Although there are very few organs in plants, each organ is composed of many cell types, often associated in the form of distinct tissues. Since different organs consist of unequal combinations of these cell types intermingled in a highly complex fashion, the meaningful interpretation of "organic-specific" gene expression becomes a difficult exercise. One approach to characterizing cell-type specific expression of chimeric genes in plants has utilized microdissection (Simpson et al., 1986, Nature 323:551–554). These methods are, however, extremely laborious, prone to varying degrees of contamination, and many cell-types within plants are inaccessible to the techniques. Alternatively, localization of chimeric gene activity by histochemical methods has been successful in other systems (Lis et al. 1984, Cell 35:403–410).

To determine whether it would be possible to use histochemistry to investigate single-cell or tissue-specific expression of GUS gene fusions in plants, preliminary experiments were carried out on sections of stems of several independently transformed rbcS-GUS and CaMV-GUS plants. Stem sections were chosen both for their ease of manipulation and because most of the cell types of a mature plant are represented in stem. To illustrate the light-regulated nature of the rbcS-GUS fusion, the plants were illuminated from one side only for one week before suctioning. Sections from both plants stained intensely with the substrate while non-transformed tissue did not stain. Sections of CaMV-GUS plants always show highest levels of activity in phloem tissues along the inside and outside of the vascular ring, most prominently in a punctate pattern that overlies the internal phloem and in the rays of the phloem parenchyma which join the internal and external phloem (Esau, 19787, The Anatomy of Seed Plants). There is also variable lighter staining throughout the parenchymal cells in the cortex and in the pith, and also in the epidermal cells, including the trichomes.

RbcS-GUS stem sections rarely, if ever, show intense staining in the trichomes, epidermis, vascular cells or pith, but tend to stain most intensely over the cortical parenchyma cells containing chloroplasts (chlorenchyma), with faint and variable staining in the pith. Although the strongest staining is most often seen in a symmetrical ring around the vascular tissue just inside the epidermis, an asymmetric distribution of staining in the cortical stem cells is sometimes observed. Suspecting that this pattern was due to uneven lighting, a plant was illuminated from one side for one week before sectioning, and it was found that the staining was asymmetric, with intense staining in the chloroplast-containing cells proximal to the light source. The staining patterns observed for both the CaMB 35S-GUS and the rbcS-GUS transformants are consistent between several independent transformants. Untransformed plants never show staining with X-Gluc, even after extending assays of several days.

8.3. DISCUSSION

New methods are provided for analyzing gene expression in transformed plants that are potentially of general utility. The beta-glucuronidase gene from *E. coli* has been expressed at high levels in transformed tobacco plants with no obvious ill effects on plant growth or reproduction. It should be emphasized that the determination of rates of enzyme activity allows accurate determination of quantity of chimeric gene production, even over an intrinsically fluorescent background. The fluorometric assay is very specific, extremely sensitive, inexpensive and rapid. Minute quantities of tissue can be assayed with confidence; recently GUS levels have been measured in isolated single cells of transformed plants.

Beta-glucuronidase is very stable in extracts and in cells, with a half-life in living mesophyll protoplasts of about 50 hours. Because of this, it is felt reasonable to interpret GUS levels as indicative of the integral of transcription and translation, rather than the rate. In addition, GUS is not completely inactivated by SDS-PAGE, can tolerate large amino-terminal fusions without loss of enzyme activity and can be transported across chloroplast membranes with high efficiency. It is believed, therefore, that the system will also be very useful in studying the transport and targeting of proteins, not only in plants, but in other systems that lack intrinsic beta-glucuronidase activity, such as *Saccharomyces cerevisiae* and *Drosophila melanogaster*.

A commercially available histochemical substrate has been used to demonstrate GUS activity in transformed plant tissue. Other substrates are available and give excellent results. It is emphasized that meaningful interpretation of results of histological analysis in terms of extent of chimeric gene activity, whether by in situ hybridization methods or by histochemistry, as presented here, is not a trivial or straightforward matter. However, with these cautions, histochemical methods can be very powerful for resolving differences in gene expression between individual cells and cell-types within tissue.

A distinctly non-uniform distribution of GUS activity in stem sections of several CaM-GUS transformed plants has been observed. Different cell-types within plants are expected to have differing metabolic activity with corresponding differences in rates of transcription and translation, and our results may reflect such a difference. Alternatively, since many of the cells of the phloem have very small cross-sectional areas, the intense dye deposition seen in these regions may simply reflect the greater cell number per unit area. The localization that is observed may also be due to a real difference in the level of expression of the CaMV 35S promoter between cell types. Recently, it has been argued that the CaMV 35S promoter is preferentially active in cells during the S phase of the cell cycle. If this is true, then the pattern of GUS staining observed may reflect cell division activity in these cells. This observation is consistent with the proposed role of the 35S transcript of CaMV in viral replication (Pfeiffer and Hohn, 1983, Cell 33:781–790). It is also interesting that the other class of plant DNA viruses, the geminiviruses, replicates in the phloem parenchyma (Kim et al., 1978, Virology 89:22–23). It is concluded therefore that it is no longer adequate to describe the 35S promoter as "constitutive" solely by the criteria of expression in all plant organs, when there may be a strong dependence of transcription on cell-type or cell cycle.

The distribution of GUS activity in the stem sections of plants transformed with rbcS-GUS genes is consistent with data that indicate a requirement for mature chloroplasts for maximal transcription of chimeric rbcS genes (simpson et al., 1986, Nature 323:551–554). Cortical parenchymal cells in the stem contain varying numbers of chloroplasts, while those in the pith and epidermis of the stem rarely contain chloroplasts.

Different cell-types present in each organ contribute differently to the patterns of gene expression, and each organ consists of different proportions of these cell-types. It has been undertaken to minimize this effect on quantitative analysis of extracts by suitable choice of a denominator. The parameter that needs to be studied with gene fusions is most often the expression of the gene fusion in each cell. When preparing homogenates from plant organs, the number of cells that contribute to the extract will vary, as will the protein content of each cell and cell-type. The DNA content of the extract will reflect the number of cells that were lysed (Labarca et al., 1980, Anal. Biochem. 102:344–352) whereas the traditional denominator, protein concentration, will not. For example, a single leaf mesophyll cell contains much more protein than a single epidermal cell or root cortical cell. However, each will have the same nucleus with the same potential to express the integrated gene fusion.

Using this approach, it is found that the differential expression of the rbcS-GUS fusion is much more pronounced between immature and mature leaf when GUS activity is expressed, per mg of DNA (see Table II). When protein concentration is used as a denominator, the massive induction of GUS activity during leaf maturation is masked by the concomitant induction of proteins involved in photosynthesis.

The observation that the specific activity of GUS produced by CaMV-GUS fusions is the same in immature and mature leaves when expressed using a protein denominator indicates that the rate of GUS accumulation closely follows the rate of net protein accumulation. The two-fold difference in GUS specific activity using a DNA denominator illustrates the accumulation of GUS per cell over time. This quantitative analysis, together with histochemical data, may indicate that the differences between GUS activity in the leaf, stem and root of CaMV-GUS fusion plants could reflect the larger proportion of phloem-associated cells in roots and stems compared to leaves. It is felt that the choice of a DNA denominator best reflects the expression per cell, and hence is a more accurate reflection of the true regulation of the gene.

9. EXAMPLE: CLONING AND EXPRESSION OF THE *ESCHERICHIA COLI* GLUCURONIDE PERMEASE GENE

Upon sequencing the gene for β-glucuronidase sequence, analysis indicated the presence of a second open reading frame of at least 340 bp, whose initiator codon overlapped the translational terminator of the β-glucuronidase gene. This open reading frame was found to be translationally active (Jefferson, R. A., 1985, Dissertation, University of Colorado, Boulder).

9.1. MATERIALS AND METHODS

9.1.1. PLASMIDS AND DNA

FIG. 14 illustrates the clones used to analyze the uid A locus of *E. coli*. pRAJ220 plasmid was used to deduce the sequence of β-glucuronidase; pRAJ210 was subcloned and the fragments 3' to the β-glucuronidase gene, encoding the open reading frame, were sequenced. The resulting DNA sequence and predicted protein are shown in FIG. 15.

9.2. RESULTS AND DISCUSSION

9.2.1. LOCATING THE GLUCURONIDE PERMEASE CODING REGION

By analogy with existing operons of *E. coli*, it appeared that the open reading frame encoded a permease protein that could facilitate the uptake of β-glucuronides. The lactose and melibiose operons (for example) consist of a gene encoding a hydrolytic enzyme followed by a cocistronic gene for the corresponding transport protein, or permease. This format, of genes with interdependent functions being located on the same mRNA and subject to the same controlling mechanisms, is ubiquitous in bacteria. Because the substrates for glucuronidase are very polar, it is certain that they require active transport across the bacterial membrane. The level of genetic analysis performed on the uid locus would not have distinguished a mutation that eliminated β-glucuronidase function from a mutation that eliminated transport of a substrate, consistent with tight linkage between β-glucuronidase and glucuronide permease. These facts led to the hypothesis that the open reading frame encoded the glucuronide permease. Further analysis has also indicated that the range of substrates for β-glucuronidase that can be transported by the glucuronide permease is much wider than that of any previously described glycoside permease.

9.2.2. ANALYSIS OF AMINO ACID SEQUENCE AND THE GLUCURONIDE PERMEASE PROTEIN

The predicted amino acid sequence of the putative glucuronide permease was subjected to computer analysis to determine the existing sequences to which it had closest homology. The only two sequences that had significant homology to the glucuronide permease were the melB gene product, the melibiose permease, and the lacy gene product, the lactose permease. Of these, the homology with the melibiose permease is the strongest, and is shown in FIG. 16. Interestingly, both the melibiose and lactose permeases are members of a class of sugar transporters that use the proton gradient of the cell membrane to drive the transport of the sugar against a concentration gradient. These permeases are also in the unusual class that have been purified and shown to be active as single proteins, and whose activity can readily be reconstituted in vitro by addition of the pure permease to membrane vesicles.

The deduced amino acid sequence for glucuronide permease was subjected to a computer analysis to predict the structure of the protein. Such results are shown in FIG. 17. The salient feature of the analysis is the extremely hydrophobic nature of the protein, and the long stretches of hydrophobic amino acids that could easily span a membrane. The Kyte-Doolittle predictions of hydropathy (shown in the bottom frame) reveal hydrophobic regions that are located at almost identical positions to those of the melibiose permease, and at very similar positions to those of the lactose permease.

9.2.3. MOLECULAR GENETIC DEMONSTRATION OF GLUCURONIDASE PERMEASE

The proof of the glucuronide permease function was obtained by cloning the putative permease gene under the control of a heterologous promoter, in this case the promoter of the lactose operon of *E. coli*. When wild-type *E. coli* cells are planted on LB agar petri plates containing the chromogenic substrate for GUS, 5-bromo-4-chloro-3-indolyl-beta-D-glucuronide (called X-Gluc), the colonies remain white. When excess glucuronidase is present in the cells, for instance when encoded by a plasmid, the colony turns blue, due to deposition of the indigo dye. The blue color in this case is caused by (GUS) enzyme that is released from the many broken cells in the colony. This tends to give a relatively diffuse blue colony, with dye being deposited on the agar around the colony as well as on the colony itself. If however, a plasmid containing, not GUS, but rather the permease gene linked to the lac promoter, is introduced into the wild-type cells, the colonies on X-gluc become deep blue. The phenotype is even more striking because the blue color is very discrete, and is strictly localized to the colony. These colonies do not produce any detectable GUS in the absence of X-gluc, but rather are induced by produce it when X-gluc is present. This is due to the X-gluc being transported into the cell, binding to the uidR gene product (the repressor of the uid operon) and allowing expression of GUS. This phenomenon requires the glucuronide permease action. This can best be seen in the series of cloning experiments summarized in Table III.

TABLE III

BEHAVIOR OF *E. COLI* STRAIN DH5-CONTAINING VARIOUS lacZ-GLUCURONIDE PERMEASE FUSIONS IN pUC19

| Plasmid | Color on X-Gluc plates |
| --- | --- |
| pRAJ 280 (lacZ/permease fusion) | Blue |
| pRAJ 281 (Sst I lacZ frameshift) | Blue |
| pRAJ 282 (Nsi I frameshift) | White |
| pRAJ 283 (Acc I frameshift) | White (trace of blue at 2 days) |
| pRAJ 284 (Sst I & Ban II frameshift) | Whiteish (very pale blue) |
| pRAJ 285 (Nco I- Pst I 3' deletion) | Blue |
| pRAJ 286 (5' end, Bam HI linker) | Dark Blue (small) |
| pRAJ 287 (3' end Bam HI linker) | Dark Blue (small) |

The glucuronide permease gene was subcloned into pUC19 to give a gene fusion with lac that caused *E. coli* to give discrete blue colonies on X-gluc. This was then subjected to various changes to alter the reading frame of the predicted permease to determine whether the reading frame was required for the blue colony phenotype. Restriction endonuclease sites were chosen that were distributed throughout the gene. Some of these are indicated in FIG. 15. The restriction sites were cleaved and filled in to mutate the area around the site by shifting the putative reading frame. Such a shift occurring upstream of the glucuronide permease initiator codon (pRAJ218) showed no change in the color of the resulting colony. However, frame shifts within the coding sequence eliminated or severely reduced the capacity of the gene to give rise to colored colonies. In particular the Nsi I site mutant (PRAJ282) was completely colorless and the Acc I site mutant (pRAJ283) was almost completely colorless, with just a trace of blue after two days. The Ban II site frame-shift showed a faint trace of blue overnight with an obvious, but still quite pale, blue after two days on plates.

The elimination of all blue color by the Nsi I mutant is expected, as the amount of permease made before the frame shift is very small—on the order of 100 amino acids. The next frame shift, the Acc I mutant, showed a trace of permease action. This may be because the amount of permease made (more like half of the permease) could have residual activity. The Ban II mutant (in which more than 80% of the permease is made) shows a definite but severely reduced activity. This is also as would be predicted, and demonstrates conclusively the role of the open reading frame in the development of the blue colony.

The deletion mutant that extended 3' from the Nco site at bp 1510 (pRAJ285) caused no obvious change, leaving dark blue colonies. This verified the 3' extent of the gene as predicted by DNA sequencing. The context of the start site of the gene was altered by oligonucleotide mutagenesis in order to verify its location. This resulted in a permease gene deleted of sequences up to −12 from the initiator codon. This mutant showed an even darker blue colony (and smaller—presumably due to the over-expression of the membrane protein). The higher level of permease in these cells may be due to better translation on the new mRNA, perhaps because of loss of attenuating sequences. This clone, pRAJ286, contains a Bam HI linker immediately 5' of the Shine/Delgarno sequence and ensures that the initiator codon is the first one presented on any hybrid mRNA produced from this cloned fragment. To make a more useful cassette, pRAJ286 was modified by the addition of another Bam HI linker at the 3' end. This vector, pRAJ287, contains the entire glucuronide permease gene as a Bam HI fragment within the polylinker sites of the plasmid pUC19.

Next, the ability of the glucuronide permease to transport substrates other than X-gluc was tested. If the permease could transport such a large heterocyclic molecule as X-gluc, it was reasonable that it could transport other complex glucuronides, and hence offer a general route to transporting GUS substrates. Two bacterial cultures, one containing the plasmid pRAJ230 and the other pRAJ210 (Jeffeson et al. 1986) were grown to similar densities in L broth. Both these cultures produce GUS within the cells. pRAJ210 also includes the DNA encoding the permease—pRAJ230 is deleted of most of the permease gene. The cultures were washed extensively to eliminate GUS from the medium, and incubated with a solution of 4-methyl-umbelliferyl glucuronide, a fluorogenic substrate for GUS. The culture containing PRAJ210 immediately began to fluoresce intensely, while the culture containing pRAJ210 did not. When the cultures were lysed with a sonicator in the presence of fluorogenic substrate, both extracts showed intense fluorescence indicative of intact β-glucuronidase activity.

10. EXAMPLE: TRANSGENIC PLANTS EXPRESSING A BETA-GLUCURONIDASE GENE FUSION AND ALTERATION OF GROWTH PATTERNS BY AUXIN-GLUCURONIDE

10.1. MATERIALS AND METHODS

Tryptophyl glucuronide was synthesized from indole-3-ethanol by conventional Koenigs-Knorr condensation. Leaf discs were prepared from untransformed plants or plants transformed with a highly expressed CaMV 35S/GUS gene fusion as described in section 8, supra. Leaf discs from nontransformed and CaMV 35S/GUS transformed plants were exposed to media containing cytokinin and (i) no auxin, (ii) µM tryptophyl-glucuronide, or (iv) 10 µM tryptophyl glucuronide.

10.2. RESULTS AND DISCUSSION

Indole-3-ethanol (tryptophol) has been shown to be an auxin in several systems. It has been proposed that indole ethanol represents a buffered storage form of auxin, in a branch point leading from indole-3-acetaldehyde (the immediate precursor of the known auxin indole-3-acetic acid (IAA). In the absence of auxin, leaf discs from control plants and CaMV 35S/GUS-transformed "GUS-plants" became chlorotic and died over a 7 week period (FIG. 18). In both GUS-expressing and control plants, the effect of 1 µM IAA was similar, resulting in the persistance of chlorophyll and the maintenance of living healthy cells. On media in which tryptophyl glucuronide was the sole auxin source, only those leaves which expressed GUS remained green and healthy, presumably because they were able to cleave active auxin from tryptophyl glucuronide.

11. EXAMPLE: THE USE OF GUS FUSIONS IN TRANSGENIC PLANTS: REGULATION OF CHIMERIC PATATIN GENES IN TRANSGENIC POTATO PLANTS

While the potato is perhaps the most important non-cereal stable crop in the world, at least in terms of acreage under cultivation and tonnage, it is one of the most poorly understood. The potato is a relatively new crop, with only a modest history of genetic improvement when compared to cereals such as wheat and maize. Potatoes are propagated vegetatively, and most commercial cultivars are poorly characterized tetraploids of limited fertility, hence conventional breeding is not simple or straightforward. These factors strengthen the argument that potatoes will be one of the first crops to specifically benefit from improvement by non-traditional means, and in particular by genetic engineering. As a solanaceous plant, *Solanum ruberosum* is highly susceptible to infection by *Agrobacterium tumefaciens*, and genetic transformation by this route has become routine. However, the ability to introduce new genes into a crop only makes more urgent our need to Understand how these genes function, so that sensible strategies for copy improvement by these powerful new tools can be developed.

The goal of the experiments described below was to develop an understanding of the behaviour and regulation of a gene encoding patatin—a major protein of the potato tuber—in laboratory, glasshouse and field grown potato plants. Towards this end, transgenic approaches using GUS fusions were used to increase the resolution of the analysis and to facilitate the experiments.

Patatin is a 40 kDa glycoprotein that accumulates in tubers to up to 40% of the total soluble protein (reviewed by Park, 1986 Potato Physiology, Li. ed., Academic Press). The function of patatin is still obscure, but it is clearly associated with storage tissue. Induction of patatin mRNA transcription can also be observed in vitro when single node cuttings are subjected to tuberization conditions, even when tuberization itself does not occur (Paiva et al., 1983, Plant Physiol. 71:616–618). It is encoded by a gene family with more than a dozen members, meaning that in the normally tetraploid cultivated potato there are upwards of fifty possible genes bearing patatin coding sequences in many allelic and nonallelic loci (Mignery et al., 1988 Gene 62:27–44; Twell and Ooms, 1988 Mol. Gen. Genet. 212:325–326). Each of these genes may behave differently, some regulated to express at high levels, others at very low or even inactive levels—and, perhaps, with different spatial and temporal control regimes. How then can one distinguish between the contribution of one gene from that of another, or even its allele? The easiest way, and the way that allows experimental manipulation of the DNA, is to mark one isolated gene in vitro such that it can be readily studied distinct from others, and re-introduce it into the host genome; that is, to construct a transgenic plant using a chimeric gene, or gene fusion.

11.1. MATERIALS AND METHODS

To investigate the transcriptional regulation of the patatin gene in transgenic potato, simple gene fusions were generated between a promoter from a patatin gene and GUS. The patatin gene that was used was cloned and sequenced by Mike Bevan and his colleagues at the Plant Breeding Institute using a cDNA probe obtained from Bill Park at Texas A&M. The initial DNA constructions were simple transcriptional fusions in which varying lengths of the 5' upstream regions of the patatin gene were fused to the coding sequence of GUS contained on a plasmid called pRAJ260. Some of these fusions are outlined in FIG. 16. These constructions were subcloned within a binary Agrobacterium vector, pBIN19 (Bevan, 1984, nucl. Acids Res. 12:8711–8721) and transformed into a commercial potato cultivar by a tuber-disc method (Sheerman and Bevan, 1987 Plant Cell Reports 7:13–16), selecting for resistance to the antibiotic kanamycin. Many independent transformants were obtained for each of the promoter lengths, and subjected to further analysis.

11.2. RESULTS AND DISCUSSION

11.2.1. IN VITRO INDUCTION EXPERIMENTS

The first experiments carried out on the transformants were in vitro inductions of patatin-GUS activity. It had previously been shown by Paiva et al., (1983, Plant Physiol. 71:616–618) that accumulation of patatin protein could be induced in cuttings. To determine whether our patatin-GUS fusions were transcriptionally regulated accordingly, small single-node cuttings of the primary transformants (approximately 100) were placed on media containing either 3% sucrose without cytokinin or 7% sucrose with 2 mg/l enzyladenine, under either normal lighting regime or in the dark. Under these conditions, about 30–60% of the cuttings in the dark gave small microtubers within 2 weeks, while in the light the induced cuttings accumulated high levels of starch but showed no signs of tuberization. After two weeks incubation on either of the two media, the cuttings were homogenized using mortar and pestle, and GUS levels were determined with a fluorogenic assay. Most transformants from each of the promoter classes showed strong induction of GUS activity under conditions of high sucrose and cytokinin. Interestingly, GUS levels were highly elevated in the induced cuttings irrespective of whether they were grown in the light, or in the dark with concomitant tuberization. This observation is consistent with the experiments of Paiva et al. (1983, Supra) and Bourque et al., (1987, In Vitro Cell, Devel. Biol. 23:381–386) who showed that patatin synthesis could be uncoupled from tuberization. These experiments demonstrated clearly that our patatin promoter would respond to induction phenomena that were in some sense distinct from those for tuberization—representing a subset of the tuberization induction conditions. An alternative way to interpret this is that patatin-GUS fusions are induced by all the same conditions as those for tuberizations, but do not respond to a "normal" light-inhibition of tuberization.

To better define the nature of the induction signal, different sugars and osmotica were used, including fructose, glucose, and mannitol, but none showed a significant induction; sucrose alone gave high GUS activity. In subsequent experiments we observed no reproducible stimulation of patatin-GUS induction by cytokinin so it was omitted.

An example of the induction data obtained is shown in Table IV. This table shows the GUS levels accumulated in a cutting grown in vitro for two weeks under non-induced conditions, or under conditions that induced patatin with or without concomitant tuberization (dark and light induced, respectively). The data shown are for a single patatin-GUS deletion derivative consisting of a 2164 bp promoter fragment directing GUS expression.

TABLE IV

| Transformant | Induction Conditions | | | Fold Induction | |
|---|---|---|---|---|---|
| | Uninduced | Dark | Light | Dark | Light |
| pBI141.3 | 1 | 15 | 40 | 160 | 3 | 10 |
| | #2 | 6 | 170 | 650 | 28 | 108 |
| | 3 | 12 | 85 | 135 | 7 | 11 |
| | 4 | 10 | 25 | 250 | 3 | 25 |
| | 5 | 1 | 75 | 60 | 75 | 60 |
| | 6 | 7 | 35 | 250 | 5 | 35 |
| | 7 | 6 | 9 | 300 | 2 | 50 |
| | 8 | 1 | 10 | 70 | 10 | 70 |
| | 9 | 60 | 12 | 250 | 0.2 | 4 |
| | 10 | 7 | 70 | 150 | 10 | 21 |
| | 11 | 40 | 900 | 1700 | 22 | 42 |
| | #12 | 15 | 150 | 3000 | 10 | 200 |
| | 13 | 4 | 60 | 700 | 15 | 175 |
| | 14 | 9 | 6 | 700 | 0.7 | 78 |
| | 15 | 10 | 350 | 2300 | 35 | 230 |
| | 16 | 40 | 320 | 1900 | 8 | 47 |
| | #17 | 20 | 6700 | 7300 | 335 | 365 |
| Average n = 17 | 15 | 530 | 1169 | 33 | 90 |
| Minimum | 1 | 6 | 60 | 0.2 | 4 |
| Maximum | 60 | 6700 | 7300 | 335 | 365 |

Analysis of Patatin-GUS Induction of Cuttings In Vitro for 17 Independent Transformants With pBI141.4, Consisting of a 2164 bp Promoter Fusion to GUS. Cuttings were all approximately 1 cm long, with a single leaf node with no obvious auxiliary bud growth at time zero. Cuttings were placed in petri plates containing MS media plus 3% sucrose (c.), 7% sucrose & 2 mg/l BAP (d. and e.) in the light (c. and e.) or dark (d.) for 14 days. The cuttings were removed and ground in a mortar and pestle and assayed for GUS fluorometrically. Values are expressed as nM MU/hr at 37° C. All values are per cutting, and not normalized. # denotes those plants chosen for statistical study and field trial.

While it is clear that this patatin promoter is fully capable of inducing GUS under these conditions, it is also clear that there is variation between individual transformants. Some of this variation may be due to physiological differences in the cuttings and some must be due to "position-effect" influences on the gene fusions. "Position-effect" is a very important but poorly defined issue in transgenic science that refers to variation in gene expression that can be ascribed to the influence of differing sites of integration of the foreign DNA. All currently available methods for transformation of plants result in apparently random integration of the foreign DNA into the genome of the host plant. This inability to target DNA to its homologous site or at the very least reproducible site, and the resulting uncertainties caused by neighboring sequences, local structure constraints or even three dimensional positioning in the genome can result in a confusing and frustrating variation in gene expression. The nature and mechanism(s) of this influence is not at all clear, nor is the extent of the influence.

To investigate the extent of variation that was not due to "position effect" but rather to other factors 72 clonal single node cuttings were taken from a single set of identically maintained and aged in vitro grown plantlets that were in turn all derived from a single transformant. This transformanant, 141.4-17 had been propagated for at least two years by nodal cuttings prior to analysis, and so was certainly not chimeric. The cuttings were divided into two sets of 36 cuttings, and placed on media containing either 3% sucrose or 8% sucrose in the light, noting from which region of the parental plant they were derived. After two weeks, they were homogenized and assayed for GUS activity by fluorometric measurements. The results indicated that the variation from one cutting to another was as high as one thousand-fold, although the means of the uninduced and induced cuttings were different by a factor of ten. Moreover, the distribution of GUS activity among the cuttings was so broad that a third of the highest expressing uninduced cuttings overlapped a third of the lowest expressing induced cuttings. In addition, there was absolutely no correlation between the position of the cutting on the plant and the response of the cutting to induction. The scatter was such that it would easily be possible, by inadverteantly selecting a small number of plants, to deduce that the patatin promoter was repressed under conditions that clearly give rise, on the whole, to a high induction of transcription. When a particular transformant was analyzed at several different times—as close as a month apart or as long as two years apart—the reproducibility of induction was very poor. While a highly active transformant (4–17 was our highest expressing transformant) was usually very high, the actual extent of induction varied tremendously.

These observations suggested the possibility that the influence of the physiological state of the plant or cutting was contributing perhaps as much or more to the variation in patatin-GUS expression as the genetic component of "position-effect". It is possible that the variation among clonally propagated plants is either a characteristic of patatin gene regulation, a general feature of gene regulation in sporophytic development, or indeed even a feature of our tissue culture conditions. It is easy to invoke models in which random, but stable methylation occurs to promoter sequences during the propagation in tissue culture that alters the ability of the gene fusion to express.

11.2.2. PATATIN-GUS EXPRESSION IN PLANTA

The next set of experiments was designed to investigate the temporal patterns and spatial localization of patatin transcription—as measured by GUS fusion activity—during the growth and development of the plant. A representative set of transformants—three from each promoter class, from 360 bp of 5' sequence to 3500 bp—were moved to glasshouse conditions in soil. The plants matured indistinguishably from untransformed control plants. Tubers, roots and aerial tissues were assayed for GUS activity quantitatively with fluorogenic assays and histochemically using the indigogenic substrate X-Glue (5-bromo-4-chloro-3-indolyl-$\beta$-D-glucuronide).

As with the cuttings induced in vitro, there was a very wide range of variation in GUS activity observed in planta, when assayed quantitatively. In spite of this, there was a very strong trend for GUS levels to be consistently much greater in tubers than in other organs. The answers to all of these questions will, of course, vary from system to system, but will be important for providing a solid understanding of the behaviour of genes in individuals and in populations. It is also important to acquire this information for the more pragmatic purposes of designing agronomically useful programs that involve gene transfer.

11.2.3. DESIGN OF THE FIELD TRIAL

The Patatin-GUS field trial can be considered as three separate trials, designed to address different aspects of the questions outlined above. The first trial, called GUS I was designed to measure the degree of variation in gene expression observed between independent transformants-that is, the "genetic" component of variation in chimeric gene expression. GUS II is designed to ask how much variation is not genetic, but is due to other factors, such as environmental, physiological or stochastic influences. GUS III is designed to ask how patatin-GUS expression-both quantitatively and qualitatively—changes during the course of the growing season.

11.2.3.1. GUS I

To investigate the extent of variation in patatin gene expression that could be ascribed to "position-effect" or otherwise characteristic genetic variation, a large collection of independent transformants was used. These transformants contained one of four different patatin-GUS gene fusions and were not preselected other than for the expression of detectable levels of GUS. Each transformant ws propagated vegetatively in vitro by nodal cuttings to generate 6 clonal replicates. A total of 71 independent transformants was used, giving a total of 426 transgenic plants. Control plants that were not transgenic, but that had been regenerated from shoot cultures or tuber disc, were also used. The trial was replicated in six block, each self-containing but internally randomized.

11.2.3.2. GUS II

To determine the distribution of patatin-GUS gene expression and measure the extent of variation within a particular transformant, i.e. that which is not caused by genetic differences between individuals, but rather by environmental, physiological or stochastic differences, we selected 12 independent transformed plants, three from each of the four promoter deletion classes. The plants were preselected based on easily measurable GUS activity and strong induction of patatin-GUS under tuberization conditions in vitro. These twelve transformants were propagated and multiplied vegetatiely to give 36 clonal replicas of each plant. The trial was replicated in 36 internally randomized blocks and included shoot culture and tuber-disc regenerant controls. Since six additional replicates of each of these plants was represented in GUS I, the total available replication was up to 42.

11.2.3.3. GUS III

To investigate the changes in patatin-GUS expression during the growing season, and to determine whether differences in organ-specificity occured during growth, the same twelve pre-selected transformants as in GUS II were propagated in vitro to give eighteen replicate plants for each. These eighteen replicates of twelve transformants plus controls were distributed in six blocks, each containing three replicates randomized internally. Every two weeks during the growing season, one of these blocks was randomly selected and harvested for analysis of GUS activity.

11.2.3.4. CONTAINMENT CONSIDERATION

In the design of the field trial, and during its execution, attention was given to minimizing the possibility of movement of the transgenic plant material off-site according to the recommendations of the Advisory Council on Genetic Manipulation, and by Plant Breeding Institute Safety Committee. This entailed placing the test plot well away from any other potato plot, planting guard rows of untransformed plants, containing material during harvest and processing, removal of flower buds to prevent pollen formation and potential spread, and destruction of transgenic plant material after completion of the field trial. In addition, the trial plot was sterilized and allowed to lie fallow for an extended time after harvest. The trial was performed under MAFF license no. PHF 48A/114(57).

11.2.3.5. PLANTING, GROWTH AND HARVEST PROCEDURE

Young potato plantlets derived from tissue culture were grown in peat pots in a glasshouse to a height of approximately 5–10 cm. and planted in the test plot on June 1, 1987. The planting date was chosen to minimize the possibility of a late frost, which would have deleterious consequences on young plantlets. The usual agricultural practice of planting seed tubers was not employed due to logistical constraints of producing the seed material, and time constraints. The validity of the outcome was not compromised by this planting regime, as the purpose of the trial was not to compare yield or agronomic performance with potatoes grown under normal practice, but to investigate variation within and between similarly propagated populations.

During growth of the potato plants, manual weeding and spraying with commercial fungicides and aphidicides was undertaken at regular intervals, and the plants were regularly irrigated. Immediately before harvesting, vigour was scored for all plants.

Harvesting of GUS III plants was performed every two weeks during the growing season beginning with an initial harvest of July 28. GUS I & II were harvested over the period from October 14–23. Harvesting was carried out using manual fork lifting. For GUS III, the entire plant, including aerial structures, root and tubers was harvested at the same time to ensure that the relative GUS levels in each tissue were directly comparable. For GUS I & II, aerial structures were harvested first, followed about one week later with the tuber and root samples. This protocol was followed to minimize the possibility that the tuber population would be contaminated by fungal spores or other disease agents that would decrease their suitability for storage and replanting in a subsequent trial. In addition, this method most closely approximates agricultural practice in which the aerial structures are removed well before harvest.

11.2.3.6. SAMPLING AND ASSAY OF GUS ACTIVITY

The logistics of sampling and analysis were greatly enhanced by the use of microtiter plates, and apparatus designed to use the characteristic 8×12 array. These included 1 ml polypropylene tubes in racks with the microtiter array (Micronic), microtiter plate carriers for the centrifuge, multiwell pipettors and microtiter plate absorption and fluorescence spectrometers (Titertek Multiskan Plus and Fluoroskan II). Software for direct reading of the microtiter plates, correction of mis-labelled or incorrectly specified wells, data analysis and manipulation was developed expressly for this study ("Plates" Micro-Manipulator) by David Wolfe.

11.2.3.7. RESULTS FROM THE FIELD ANALYSIS

Results from the field trial showed that even when grown in the field under conditions that approximate agricultural practice, the net expression of the patatin promoter is highly variable. It must be remembered that the GUS protein being reasonably stable, reflects an integral of gene expression over the lifetime of the reporter enzyme, not the instantaneous levels of transcription at the moment of harvest. This property is quite useful to minimize the variation that must occur daily if not hourly. The trend is still maintained that expression is by far the highest in the tubers, relative to other organis, but the extreme quantitive variation (more than one hundred fold) can be mirrored by qualitative variation. The plants that are highest in the tuber are rarely those that are highest in aerial tissues. Hence, not only is absolute expresson level modulated among clones, but relative expression in different organs as well. A possible model to explain a component of this variation emerges in considering some of the results from GUS III together with the laboratory analyses.

Studies of the mean GUS specific activity in five organ samples (tuber, root, node, stem and leaf from up to nine plants carrying the same gene fusion) showed that "organ-specificity" is completely dependent on when the plants are harvested. Early harvests show a high degree of tuber specificity, while lifts in the middle of the growing season show an increasing degeneracy in expression. The third, fourth and fifth harvest dates show very high level expression in all aerial tissues-in a large number of plants the stem and node levels are higher than tuber levels—while at the final harvest the tuber levels are prominant. It is interesting to note that the specific activity of GUS in the tubers remains roughly constant during the growing season. This implies that the accumulation of GUS protein closely follows the net accumulation of total protein in the tuber—thereby maintaining a constant ratio. This indicates that the stability of GUS during growth is very similar to the overall stability of patatin, since patatin accounts for the highest proportion of soluble proteins in the tuber. GUS activity is therefore, a measure, or "reporter," of protein content in tubers. Therefore, GUS activity in these transgenic plants may be used to serve as a general indicator of patatin promoter activity.

12. EXAMPLE: THE ENZYMATIC ACTIVITY ASSAY OF THE β-GLUCURONIDASE INDUCED BY VARIOUS GLUCURIONIDES

Bacterial WLJ1 and Sφ200 (A gus operon), were cultured in LB liquid medium until the cell absorbence reached 0.5 at 600 nm. 100 μl of the cell suspension was inoculated into 1 ml of LB liquid medium in a large test tube. 100 μl of 50° μg/ml of each glucuronide (0.5 mg in 1 ml $NaPO_4$, pH 7.0) was then added (200 μg/ml for pregnane dial glucuronide). The culture was then incubated at 37° C. with agitation (Rolling plate incubator) for 2 hours. The cell was sedimented in an Eppendorf tube by centrifugating at 13 krpm for 1 minute. The cell was then washed thoroughly with M9 salt (twice) and resuspended in 0.5 ml of glucuronidase extraction buffer containing 50 μg/ml of chloramphenicol to stop the further glucuronidase synthesis. The enzymatic activity of β-glucuronidase encoded by the gusA in each induction was then assayed based on the cleavage of its substrate, p-nitrophenyl—glucuronide (pNPG). Being cleaved by the β-glucuronidase, the aglycone released from the substrate has an absorbance peak at 405 nm. At zero time, 10 µl glucuronidase extraction of each induction was then spontaneously transferred into five of the 100 µl the enzyme assay buffer (glucuronidase extraction buffer containing 1 mM pNPG). The five enzymatic reaction for each induction were then stopped by adding 100 µl 0.4M $Na_2CO_3$ respectively at five minutes intervals. The enzymatic activity of glucuronidase was represented by the aglycone absorbance at 405 nm for each induction is shown in Table V. Equal amounts of cells were initially used for each induction. The strain Sφ200 (Δ gus operon) was used as a negative control.

13. DEPOSIT OF MICROORGANISMS

The following microorganisms containing the indicated recombinant plasmids were deposited with the National Collection of Industrial and Murine Bacteria, Torrey Research Station, Aberdeen.

| Plasmid | Host | NCIB Accession No. |
| --- | --- | --- |
| pBI 101.1 | E. coli | 12353 |
| pBI 101.2 | E. coli | 12354 |
| pBI 101.3 | E. coli | 12355 |

The present invention is not to be limited in scope by the genes and proteins exemplified or deposited microorganisms which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

conditions to the complement of nucleotides 300 to 2105 as depicted in FIG. 2 and which encodes a functional beta-glucuronidase.

2. The method according to claim 1, wherein the host cell is a plant cell.

3. The method according to claim 1, wherein the host cell is an animal cell.

4. The method according to claim 1, wherein the host cell is a fungal cell.

5. The method according to claim 1, wherein the host cell is a bacterial cell.

6. The method according to claim 1, wherein the DNA construct is a plasmid vector.

7. The method according to claim 6, wherein the plasmid vector is a binary Agrobacterium vector.

8. The method according to claim 1, wherein the DNA construct further comprises a selectable marker.

9. The method according to claim 8, wherein the selectable marker confers resistance to kanamycin.

10. The method according to claim 1, wherein the product is a protein.

11. A method of introducing a controller element into a host cell, comprising introducing into the host cell a DNA construct, the DNA construct comprising DNA encoding beta-glucuronidase and a DNA sequence of the controller element, wherein the DNA encoding beta-glucuronidase (a) encodes a protein comprising the amino acid sequence as depicted in FIG. 2 or (b) hybridizes under stringent conditions to the complement of nucleotides 300 to 2105 as depicted in FIG. 2 and which encodes a functional beta-glucuronidase, and wherein the DNA encoding beta-glucuronidase is under direction of controller element.

TABLE V

| | THE EXPRESSION OF THE GUS OPERON INDUCED BY GLUCURONIDES | | | | | | | | | |
| --- | --- | --- | --- | --- | --- | --- | --- | --- | --- | --- |
| | WJL1 Duration (minutes) | | | | | Sφ200 (gus) Duration (minutes) | | | | |
| Glucuronide (Mwt) | 5 | 10 | 15 | 20 | 25 | 5 | 10 | 15 | 20 | 25 |
| No inducer | −0.070 | 0.029 | −0.002 | 0.011 | 0.037 | −0.122 | −0.115 | −0.103 | −0.121 | −0.115 |
| Phenyl glucuronide (270.2) | 0.349 | 0.746 | 0.988 | 1.377 | 1.258 | −0.068 | −0.071 | −0.062 | −0.072 | −0.054 |
| P-Nitrophenyl-glucuronide (315.2) | 0.177 | 0.403 | 0.621 | 0.782 | 0.782 | −0.086 | −0.068 | −0.079 | −0.068 | −0.098 |
| 4-Methulumbelliferyl-glucuronide (352.3) | 0.447 | 0.776 | 1.054 | 1.310 | 1.262 | 0.013 | 0.008 | 0.018 | 0.018 | 0.020 |
| X-Gluc (521.8) | 0.398 | 0.649 | 0.870 | 1.363 | 1.169 | −0.046 | −0.042 | −0.017 | −0.060 | −0.041 |
| Tryptophol glucuronide (380.3) | 0.715 | 0.995 | 1.209 | 2.115 | 1.169 | 0.019 | −0.045 | −0.033 | −0.041 | −0.029 |
| O-aminophenyl glucuronide (285.3) | 0.596 | 0.951 | 1.144 | 1.861 | 1.471 | −0.020 | −0.017 | −0.024 | −0.024 | −0.005 |
| CN-umbelliferone-glucuronide (338.28) | 0.416 | 0.712 | 0.977 | 1.155 | 1.389 | −0.006 | −0.010 | −0.026 | −0.016 | −0.030 |
| Hydroxyquinoline glucuronide (321.3) | 0.064 | 0.111 | 0.174 | 0.251 | 0.288 | −0.055 | −0.066 | −0.048 | −0.054 | −0.076 |
| Naphthol ASBI glucuronide (548.4) | −0.053 | −0.020 | 0.014 | 0.054 | 0.091 | −0.127 | −0.116 | −0.110 | −0.107 | −0.101 |
| Phenolphthalein glucuronide (493.4) | 0.023 | 0.066 | 0.081 | 0.147 | 0.183 | −0.075 | −0.064 | −0.062 | −0.057 | −0.057 |
| Estriol-3-glucuronide (463.5) | −0.003 | 0.061 | 0.082 | 0.117 | 0.166 | −0.090 | −0.076 | −0.070 | −0.083 | −0.082 |
| Estriol-17-glucuronide (463.5) | 0.110 | 0.151 | 0.172 | 0.211 | 0.257 | 0.017 | 0.013 | 0.015 | 0.016 | 0.013 |
| Estrone-17-glucuronide (463.5) | 0.030 | 0.079 | 0.105 | 0.146 | 0.205 | −0.050 | −0.046 | −0.046 | −0.045 | −0.045 |
| Testorterone-glucuronide (463.5) | 0.031 | 0.105 | 0.095 | 0.153 | 0.200 | −0.045 | −0.020 | −0.042 | −0.027 | −0.034 |
| Pregnane diol glucuronide (496.6) | 0.035 | 0.066 | 0.100 | 0.134 | 0.165 | −0.059 | −0.063 | −0.048 | −0.060 | −0.075 |

What is claimed is:

1. A method of introducing a gene of interest or portion thereof into a host cell, comprising introducing into the host cell a DNA construct, the DNA construct comprising DNA encoding beta-glucuronidase and DNA encoding a product of the gene of interest or portion thereof, wherein the DNA encoding beta-glucuronidase (a) encodes a protein comprising the amino acid sequence as depicted in FIG. 2 or (b) hybridizes under stringent 12. The method according to claim 11, wherein the host cell is a plant cell.

13. The method according to claim 11, wherein the host cell is an animal cell.

14. The method according to claim 11, wherein the host cell is a fungal cell.

15. The method according to claim 11, wherein the host cell is a bacterial cell.

16. The method according to claim 11, wherein the DNA construct is a plasmid vector.

17. The method according to claim 16, wherein the plasmid vector is a binary Agrobacterium vector.

18. The method according to claim 11, wherein the DNA construct further comprises a selectable marker.

19. The method according to claim 18, wherein the selectable marker confers resistance to kanamycin.

20. The method according to claim 11, wherein the controller element is selected from the group consisting of a promoter, an enhancer, an operator, a ribosome binding site, a signal peptide sequence, a chloroplast targeting sequence, a mitochondrial localization sequence, a nucleus targeting sequence and an intron.

21. The method according to claim 11, wherein the controller element is a plant promoter.

22. The method according to claim 11, wherein the controller element is a promoter selected from the group consisting of a developmental type-specific promoter, a tissue type-specific promoter, a cell type-specific promoter and an inducible promoter.

23. A method of monitoring expression of a gene of interest or a portion thereof in a host cell, comprising:

(a) introducing into the host cell a DNA construct, the DNA construct comprising DNA encoding beta-glucuronidase and DNA encoding a product of the gene of interest or a portion thereof;

wherein the DNA encoding beta-glucuronidase (a) encodes a protein comprising the amino acid sequence as depicted in FIG. 2 or (b) hybridizes under stringent conditions to the complement of nucleotides 300 to 2105 as depicted in FIG. 2 and which encodes a functional beta-glucuronidase, and (b) detecting the presence of beta-glucuronidase activity, thereby monitoring expression of the gene of interest.

24. The method according to claim 23, wherein the host cell is a plant cell.

25. The method according to claim 23, wherein the host cell is an animal cell.

26. The method according to claim 23, wherein the host cell is a fungal cell.

27. The method according to claim 23, wherein the host cell is a bacterial cell.

28. The method according to claim 23, wherein the DNA construct is a plasmid vector.

29. The method according to claim 28, wherein the plasmid vector is a binary Agrobacterium vector.

30. The method according to claim 23, wherein the DNA construct further comprises a selectable marker.

31. The method according to claim 30, wherein the selectable marker confers resistance to kanamycin.

32. The method according to claim 23, wherein the product is a protein.

33. The method according to claim 23, wherein the DNA construct further comprises a promoter.

34. The method according to claim 33, wherein the DNA encoding the product and the DNA encoding beta-glucuronidase are under control of the same promoter.

35. The method according to claim 34, wherein the DNA encoding the product and the DNA encoding beta-glucuronidase are transcribed on a same RNA molecule.

36. The method according to claim 33, wherein the order of the DNA construct is promoter sequence, gene of interest, and beta-glucuronidase.

37. A method of monitoring activity of a controller element in a host cell, comprising:

(a) introducing into the host cell a DNA construct, the DNA construct comprising DNA encoding beta-glucuronidase and a DNA sequence of the controller element;

wherein the DNA encoding beta-glucuronidase (a) encodes a protein comprising the amino acid sequence as depicted in FIG. 2 or (b) hybridizes under stringent conditions to the complement of nucleotides 300 to 2105 as depicted in FIG. 2 and which encodes a functional beta-glucuronidase, and wherein the DNA encoding beta-glucuronidase is under direction of the controller element; and (b) detecting the presence of beta-glucuronidase activity, thereby monitoring activity of the controller element.

38. The method according to claim 37, wherein the host cell is a plant cell.

39. The method according to claim 37, wherein the host cell is an animal cell.

40. The method according to claim 37, wherein the host cell is a fungal cell.

41. The method according to claim 37, wherein the host cell is a bacterial cell.

42. The method according to claim 37, wherein the DNA construct is a plasmid vector.

43. The method according to claim 42, wherein the plasmid vector is a binary Agrobacterium vector.

44. The method according to claim 37, wherein the DNA construct further comprises a selectable marker.

45. The method according to claim 44, wherein the selectable marker confers resistance to kanamycin.

46. The method according to claim 37, wherein the controller element is selected from the group consisting of a promoter, an enhancer, an operator, a ribosome binding site, a signal peptide sequence, a chloroplast targeting sequence, a mitochondrial localization sequence, a nucleus targeting sequence and an intron.

47. The method according to claim 37, wherein the controller element is a plant promoter.

48. The method according to claim 37, wherein the controller element is a promoter selected from the group consisting of a developmental type-specific promoter, a tissue type-specific promoter, a cell type-specific promoter and an inducible promoter.

49. A method for transforming a host cell with a gene of interest or portion thereof, comprising:

(a) introducing into the host cell a DNA construct, file DNA construct comprising DNA encoding beta-glucuronidase mad DNA encoding a product of the gene of interest or a portion thereof, such that the DNA construct integrates into the genome of the host cell;

wherein the DNA encoding beta-glucuronidase (i) encodes a protein comprising the amino acid sequence as depicted in FIG. 2 or (ii) hybridizes under stringent conditions to the complement of nucleotides 300 to 2105 as depicted in FIG. 2 and which encodes a functional beta-glucuronidase; and (b) detecting the presence of beta-glucuronidase activity, thereby establishing that the host cell is transformed.

50. The method according to claim 49, wherein the host cell is a plant cell.

51. The method according to claim 49, wherein the host cell is an animal cell.

52. The method according to claim 49, wherein the host cell is a fungal cell.

53. The method according to claim 49, wherein the host cell is a bacterial cell.

54. The method according to claim 49, wherein the DNA construct is a plasmid vector.

55. The method according to claim 49, wherein the plasmid vector is a binary Agrobacterium vector.

56. The method according to claim 49, wherein the DNA construct further comprises a selectable marker.

57. The method according to claim 56, wherein the selectable marker confers resistance to kanamycin.

58. The method according to claim 49, wherein the product is a protein.

59. The method according to claim 49, wherein the DNA construct further comprises a promoter.

60. The method according to claim 59, wherein the gene of interest and beta-glucuronidase are under control of the same promoter.

61. The method according to claim 60, wherein the gene of interest and beta-glucuronidase are transcribed on a same RNA molecule.

62. A recombinant DNA molecule comprising DNA encoding a glucuronide permease,
   wherein the DNA encoding the glucuronide permease comprises the amino acid sequence as depicted in FIG. 15, or hybridizes under stringent conditions to the complement of the sequence comprising nucleotides 94–1464 as depicted in FIG. 15 and which encodes a functional glucuronide permease.

63. The recombinant DNA molecule according to claim 62, wherein the DNA encoding glucuronide permease comprises the nucleotide sequence as depicted in FIG. 15 from about nucleotide number 94 to about nucleotide number 1464.

64. The recombinant DNA molecule according to claim 62, wherein the DNA encoding glucuronide permease comprises the nucleotide sequence as depicted in FIG. 15 from about nucleotide number 106 to about nucleotide number 1464.

65. A vector, comprising a recombinant DNA molecule according to any one of claims 62, 63, or 64, wherein the glucuronide permease is under direction of a controller element.

66. The vector according to claim 65, wherein the controller element is a plant promoter.

67. The vector according to claim 65, wherein the controller element is a promoter selected from the group consisting of a developmental type-specific promoter, a tissue type-specific promoter, a cell type-specific promoter and an inducible promoter.

68. A host cell comprising the vector according to claim 65.

69. The host cell according to claim 68, wherein the host cell is a plant cell.

70. The host cell according to claim 68, wherein the host cell is an animal cell.

71. The host cell according to claim 68, wherein the host cell is a fungal cell.

72. The host cell according to claim 68, wherein the host cell is a bacterial cell.

73. A method of releasing a compound from a glucuronide in a host cell, comprising:

(a) introducing into the host cell a DNA construct, the DNA construct comprising DNA encoding beta-glucuronidase;
   wherein the DNA encoding beta-glucuronidase (a) encodes a protein comprising the amino acid sequence as depicted in FIG. 2 or (b) hybridizes under stringent conditions to the complement of nucleotides 300 to 2105 as depicted in FIG. 2 and which encodes a functional beta-glucuronidase; and
(b) exposing the host cell to the glucuronide, wherein the glucuronide is cleaved by the beta-glucuronidase, such that the compound is released.

74. The method according to claim 73, wherein the compound is an auxin.

75. The method according to claim 74, wherein the auxin is indole-3-ethanol.

76. The method according to claim 73, wherein the compound is a hormone.

77. The method according to claim 73, wherein the compound is a toxin.

78. The method according to claim 73, wherein the host cell is a plant cell.

79. The method according to claim 73, wherein the host cell is an animal cell.

80. The method according to claim 73, wherein the host cell is a fungal cell.

81. The method according to claim 73, wherein the host cell is a bacterial cell.

82. The method according to claim 73, wherein the compound is a herbicide.

83. A method of releasing a compound from a glucuronide in a host cell expressing endogenous beta-glucuronidase, comprising:

(a) introducing into the host cell expressing endogenous beta-glucuronidase a DNA construct, the DNA construct comprising DNA encoding glucuronide permease,
   wherein the DNA encoding the glucuronide permease comprises the amino acid sequence as depicted in FIG. 15, or hybridizes trader stringent conditions to the complement of the sequence comprising nucleotides 94–1464 as depicted in FIG. 15 and which encodes a functional glucuronide permease; and
(b) exposing the cell to a glucuronide, wherein the glucuronide is cleaved by the beta-glucuronidase, such that the compound is released.

84. The method according to claim 83, wherein the compound is a hormone.

85. The method according to claim 83, wherein the compound is a toxin.

86. The method according to claim 83, wherein the compound is an antibiotic.

87. The method according to claim 83, wherein the compound is a drug.

* * * * *